(12) United States Patent
Feldstein et al.

(10) Patent No.: US 10,738,302 B2
(45) Date of Patent: Aug. 11, 2020

(54) COMPOSITIONS AND METHODS FOR IDENTIFYING POLYNUCLEOTIDES OF INTEREST

(71) Applicant: The Regents of the University of California, Oakland, CA (US)

(72) Inventors: Paul A. Feldstein, San Francisco, CA (US); James E. Lincoln, Woodland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/737,297

(22) PCT Filed: Jun. 24, 2016

(86) PCT No.: PCT/US2016/039348
§ 371 (c)(1),
(2) Date: Dec. 17, 2017

(87) PCT Pub. No.: WO2016/210321
PCT Pub. Date: Dec. 29, 2016

(65) Prior Publication Data
US 2018/0155712 A1 Jun. 7, 2018

Related U.S. Application Data

(60) Provisional application No. 62/184,868, filed on Jun. 26, 2015.

(51) Int. Cl.
| C12N 15/10 | (2006.01) |
| C12Q 1/6869 | (2018.01) |
| C12Q 1/6874 | (2018.01) |
| C12N 5/00 | (2006.01) |

(52) U.S. Cl.
CPC ..... *C12N 15/1093* (2013.01); *C12N 15/1051* (2013.01); *C12N 15/1096* (2013.01); *C12Q 1/6869* (2013.01); *C12Q 1/6874* (2013.01)

(58) Field of Classification Search
None
See application file for complete search history.

(56) References Cited

U.S. PATENT DOCUMENTS

| 8,158,595 B2 | 4/2012 | Galloway |
| 2004/0259079 A1 | 12/2004 | Barber |
| 2006/0029958 A1 | 2/2006 | Sakanyan |
| 2006/0074041 A1 | 4/2006 | Johnston |
| 2008/0207539 A1 | 8/2008 | Arbuthnot |
| 2014/0206546 A1 | 7/2014 | Chenchik |
| 2018/0155713 A1* | 6/2018 | Feldstein .............. C12N 15/111 |

FOREIGN PATENT DOCUMENTS

| WO | 2005021751 A | 3/2005 |
| WO | 2008058291 A2 | 5/2008 |
| WO | 2014022702 A2 | 2/2014 |
| WO | 2016210321 A2 | 12/2016 |

OTHER PUBLICATIONS

ISA/US, United States Patent and Trademark Office (USPTO), International Search Report and Written Opinion dated Jan. 10, 2017, related PCT international application No. PCT/US2016/039348, pp. 1-14, claims searched, pp. 15-29/.
European Patent Office (EPO), extended European search report dated Dec. 12, 2018, related European patent application No. 16815419.3, pp. 1-9, claims searched, pp. 10-12.
Liang, Joe C., "A high-throughput, quantitative cell-based screen for efficient tailoring of RNA device activity", Nucleic Acids Research, 2012, vol. 40, No. 20, published online Jul. 18, 2012, pp. 1-14, supplementary data, 19 pages (33 pages total).
Shen, Shensi et al., "Dynamic signal processing by ribozyme-mediated RNA circuits to control gene expression", Nucleic Acids Research, 2015, vol. 43, No. 10, pubished online Apr. 27, 2015, pp. 5158-5170, Supplementary Information, 61 pages (74 pages total).

* cited by examiner

*Primary Examiner* — Sean McGarry
(74) *Attorney, Agent, or Firm* — O'Banion & Ritchey LLP; John P. O'Banion

(57) ABSTRACT

Provided are constructs and methods useful for the screening and identification of polynucleotide sequences of interest, in particular promoters, RNA stability modifying sequences and transcriptional modifying sequences.

11 Claims, 36 Drawing Sheets

Specification includes a Sequence Listing.

```
    10         20         30         40         50         60         70         80         90        100
     *          *          *          *          *          *          *          *          *          *
1 AGATCTGACCGTCCTGTCCGTATGACAGAGAAGTCAACCAGAGAAACACGTTGTGTATATTACCTGGTGGCGCGCCGAATTCTGGGTG 100
  >>>>>               >>>>>>>>>>>>>>>>>>>>>>>>>>>>>>>>>>>>>>>>>>>>>>>>>>>>>>>>>>>>>>>>>>>>
   P5                  E48                                                Reverse transcriptase primer 1
          >>>>>>>>                                                        >>>>>>>>>>>>>>>>>>>>>>
           D8                                                              Multiple cloning site (MCS)

110        120        130        140        150        160        170        180        190       200
     *          *          *          *          *          *          *          *          *          *
101 CCAAGGGTTCAGAGAGTTCTACAGAGTTCGAGAGTTCCTGCGGGCCGCGTCGACGATCGGGCCGCGTCCTGCAGGTGACCGTCCTGTCTCTAGAGCGCGTTGCTGGCGTT 200
                                                                                                   <<<<<<<<<<<<<<
                                                                                                    rep (pMB1)
                                                           >>>>>>>>
                                                            second D8
                                              >>>>>>>>>>>>>>>>>>>>>>
                                                 >>>>>
                                                  second P5
     >>>>>
      Reverse transcriptase primer 1
                          Multiple cloning site (MCS)

210        220        230        240        250        260        270        280        290       300
     *          *          *          *          *          *          *          *          *          *
201 TTTCCATAGGCTCCGCCCCCCTGACGAGCATCACAAAAATCGACGCTCAAGTCAGAGAGTGGCGAAACCCGACAGGACTATAAAGATACCAGGCGTTTCCC 300
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     rep (pMB1)
                                      <<<<<<<<<<<<<<<<<<<<
                                       seq2
```

*Fig. 2A*

```
       310        320        330        340        350        360        370        380        390        400
301 CCTGGAAGCTCCCTGCGTCGCGCTCTCCGTGTTCCGAACCCTGTCCGCGCTTACCGGATACCTGTCCGCCGCTTTCTCCCTTCGGGAAGCGTGGCGCTTTCTCATAGCT 400
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

410        420        430        440        450        460        470        480        490        500
401 CACGCTGTAGGTATCTCAGTTCGGTGTAGGTCGTTCGCTCCAAGCTGGGCTGTGTGCACGAACCCCCGTTCAGCCCGACCGCTGCGCCTTATCCGGTAA 500
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

510        520        530        540        550        560        570        580        590        600
501 CTATCGTCTTGAGTCCAACCCGGTAAGACACGACTTATCGCCACTGGCAGCAGCCACTGGTAACAGGATTAGCAGAGCGAGGTATGTAGGCGGTGCTACA 600
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

610        620        630        640        650        660        670        680        690        700
601 GAGTTCTTGAAGTGGTGGCCTAACTACGGCTACACTAGAAGAACAGTATTTGGTATCTGCGCTCTGCTGAAGCCAGTTACCTTCGGAAAAAGAGTTGGTA 700
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

710        720        730        740        750        760        770        780        790        800
701 GCTCTTGATCCGGCAAACAAACCACCGCTGGTAGCGGTGGTTTTTTTGTTTGCAAGCAGCAGATTACGCGCAGAAAAAAAGGATCTCAAGAAGATCCTTT 800
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)
```

Fig. 2B

```
            810        820        830        840        850        860        870        880        890        900
             *          *          *          *          *          *          *          *          *          *
801 GATCTTTTCTACGGGGTCTGACGCTCAGTGGAACGAAAACTCACGTTAAGGGATTTTGGTCATGAGATTATCAAAAAGGATCTTCACCTAGATCCTTTTA 900
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<

910        920        930        940        950        960        970        980        990       1000
             *          *          *          *          *          *          *          *          *          *
901 AATTAAAAATGAAGTTTTAAATCAATCTAAAGTATATATGAGTAAACTGGTCTGACAGTTACCAATGCTTAATCAGTGAGGCACCTATCTCAGCGATCT 1000
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
                                                                                           ampR 1010       1020       1030       1040       1050       1060       1070       1080       1090       1100
             *          *          *          *          *          *          *          *          *          *
1001 GTCTATTTCGTTCATCCATAGTTGCCTGACTCCCCGTCGTGTAGATAAACTACGATACGGGAGGGCTTACCATCTGGCCCCAGTGCTGCAATGATACCGCG 1100
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1110       1120       1130       1140       1150       1160       1170       1180       1190       1200
             *          *          *          *          *          *          *          *          *          *
1101 AGACCCACGCTCACCGGCTCCAGATTTATCAGCAATAAACCAGCCAGCCGGAAGGGCCGAGAAGTGGTCCTGCAACTTTATCCGCCTCCATCCAG 1200
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1210       1220       1230       1240       1250       1260       1270       1280       1290       1300
             *          *          *          *          *          *          *          *          *          *
1201 TCTTATTAATTGTTGCCGGGAAGCTAGAGTAAGTAGTTCGCCAGTTAATAGTTTGCGCAACGTTGTTGCCATTGCTACAGGCATCGTGGTGTCACGCTCGT 1300
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR
```

Fig. 2C

```
      1310      1320      1330      1340      1350      1360      1370      1380      1390      1400
        *         *         *         *         *         *         *         *         *         *
1301 CGTTTGGTATGGCTTCTTCAGTCTCCGGTTCCCAACGATCAAGGCGAGTTACATGATCCCCCATGTTGTGCAAAAAAGCGGGTTAGCTCCTTCGGTCCTCC 1400
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1410      1420      1430      1440      1450      1460      1470      1480      1490      1500
        *         *         *         *         *         *         *         *         *         *
1401 GATCGTTGTCAGAAGTAAGTTGGCCGCAGTGTTATCACTCATGGTTATGGCAGCACTGCATAATTCTCTTACTGTCATGCCATCCGTAAGATGCTTTTCT 1500
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1510      1520      1530      1540      1550      1560      1570      1580      1590      1600
        *         *         *         *         *         *         *         *         *         *
1501 GTGACTGGTGAGTACTCAACCAAGTCATTCTGAGAATAGTGTATGCGGCGACCGAGTTGCTCTTGCCCGGCGTCAATACGGGATAATACCGCGCCACATA 1600
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1610      1620      1630      1640      1650      1660      1670      1680      1690      1700
        *         *         *         *         *         *         *         *         *         *
1601 GCAGAACTTTAAAAGTGCTCATCATTGGAAAACGTTCTTCGGGGCGAAAACTCTCAAGGATCTTACCGCTGTTGAGATCCAGTTCGATGTAACCCACTCG 1700
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR
```

*Fig. 2D*

```
         1710      1720      1730      1740      1750      1760      1770      1780      1790      1800
           *         *         *         *         *         *         *         *         *         *
1701 TGCACCCAACTGATCTTTCAGCATCTTTTACTTTTCACCAGCCGTTTCTGGGTGAGCAAATGCCGCAAAAAAGAGGAATAAGGGCGACA 1800
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1810      1820      1830      1840      1850      1860      1870      1880      1890      1900
           *         *         *         *         *         *         *         *         *         *
1801 CGGAAATGTTGAATACTCATACTCTTCCTTTTTCAATATTATTGAAGCATTTATCAGGGTTATTGTCTCATGAGCGGATACATATTTGAATGTATTTAGA 1900
     <<<<<<<<<<<<<<<<<<<<<<<<<<<<<<<<<<<<<<<<<<<<<<<<<<<<<<>>>>>>>>>>>>>>>>>>>>>>>>>>>>>>>>>>>>>>>>>>>>>>>
     ampR                                                    seq1
                                                                                      <<<<<<<<<<<<<<<<
                                                                                      ampr promoter 1910      1920
           *         *
1901 AAAATAAACAAATAGGGGTTCCGCG 1925
     <<<<<<<<<<<<<<<<<<<<<<<<<
1901 AAAATAAACAAATAGGGGTTCCGCG 1925
     <<<<<<<<<<<<<<<<<<<<<<<<<
     ampr promoter
```

*Fig. 2E*

```
         10        20        30        40        50        60        70        80        90       100
          *         *         *         *         *         *         *         *         *         *
  1 AGATCTGACAGTACTGTCCGTATGACAGCGAAGTCAAACGGCGAAACACACCTTGTGTGGTATATTACCCGTTCCTAGGTCTCGTGGGCTCGTCGTCG 100
    >>>>>                            >>>>>>>>>>>>>>>>>>>>>>>>>>>>>>>>>>>>>>>>>>>>>>  >>>>>>>>>>>>>>>>>>
    P5              sArMV E50                                       Reverse transcriptase primer 3
         >>>>>>>>                                                                        >>>>>>
         D8                                                                              Primer 4

110       120       130       140       150       160       170       180       190       200
          *         *         *         *         *         *         *         *         *         *
101 GCAGCGGTCGGTACCACTAGTAGTTGACCGTCCTGTCCGTATGACAGAGAAGTCAACCAGAGAGAAACACGTTGTGTGGTATATTACCTGTGGCGGCCGAATTC 200
    >>>>>>                      >>>>>                                                     >>>>>>>>>>>>>>
         second P5                         sTRSV E48                                      Multiple cloning site (MCS)
                >>>>>>
                second D8
    >>>>>>>    >>>>>>
    Primer 4   Barcode insertion site 210       220       230       240       250       260       270       280       290       300
          *         *         *         *         *         *         *         *         *         *
201 TGGAATTCGGGTGCCAAGGGTTCAGAGTTCTACAGTCCGACGTTCCTGCAGTGACCTTCGACGATCGGCCGCCGGTCGACGTTGAGCTTCCTGTCTCTAGA 300
    >>>>>>>>>>>>>>>>>>>>>>>>>>>>>>>>>>>>>>>>>>>>>>>>>>>>>>>>>>>>>>>>                           >>>>>
                                                                                               third D8
    >>>>>>>>>>>>>>>>>                                                                      >>>>>
    Reverse transcriptase primer 1                                                         third P5
    >>>>>>>>>>>>>>>>>
    Primer 2
    >>>>>>>>>>>>>>>>>>>>>>>>>>>>>>>>>>>>>>>>>>>>>>>>>>>>>>>>>>>>>>>>
    Multiple cloning site (MCS)
```

*Fig. 4A*

```
      310        320        330        340        350        360        370        380        390        400
       *          *          *          *          *          *          *          *          *          *
301 CGCCTTGCTGGCCGTTTTCCATAGGCTCCGCCCCCTGACGAGCATCACAAAAATCGACGCTCAAGTCAGAGAGGTGGCGAAACCCGACAGGACTATAAAGA 400
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)
                                                                   <<<<<<<<<<<<<<<<
                                                                        seq2

410        420        430        440        450        460        470        480        490        500
       *          *          *          *          *          *          *          *          *          *
401 TACCAGGCGTTTCCCCCTGGAAGCTCCCTCGTGCGCTCTCCTGTTCCGACCCTGCCGCTTACCGGATACCTGTCCGCCTTTCTCCCTTCGGGAAGCGTGG 500
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

510        520        530        540        550        560        570        580        590        600
       *          *          *          *          *          *          *          *          *          *
501 CGCTTTCTCATAGCTCACGCTGTAGGTATCTCAGTTCGGTGTAGGTCGTTCGCTCCAAGCTGGGCTGTGTGCACGAACCCCCGTTCAGCCCGACCGCTG 600
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

610        620        630        640        650        660        670        680        690        700
       *          *          *          *          *          *          *          *          *          *
601 CGCCTTATCCGGTAACTATCGTCTTGAGTCCAACCCGGTAAGACACGACTTATCGCCACTGGCAGCAGCCACTGGTAACAGGATTAGCAGAGCGAGGTAT 700
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

710        720        730        740        750        760        770        780        790        800
       *          *          *          *          *          *          *          *          *          *
701 GTAGGCGGTGCTACAGAGTTCTTGAAGTGGTGGCCTAACTACGGCTACACTAGAAGAACAGTATTTGGTATCTGCGCTCTGCTGAAGCCAGTTACCTTCG 800
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)
```

*Fig. 4B*

```
       610        620        630        640        650        660        670        680        690        700
        *          *          *          *          *          *          *          *          *          *
601 CGCCTTATCCGGTAACTATCGTCTTGAGTCCAACCCGGTCAAGACACGACTTATCGCCACTGGCAGCAGCCACTGGTAACAGGATTAGCAGAGCGAGGTAT
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

710        720        730        740        750        760        770        780        790        800
        *          *          *          *          *          *          *          *          *          *
701 GTAGGCGGTGCTACAGAGTTCTTGAAGTGGTGGCCTAACTACGGCTACACTAGAAGAACAGTATTTGGTATCTGCGCTCTGCTGAAGCCAGTTACCTTCG
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

810        820        830        840        850        860        870        880        890        900
        *          *          *          *          *          *          *          *          *          *
801 GAAAAAGAGTTGGTAGCTCTTGATCCGGCAAACAAACCACCGCTGGTAGCGGTGGTTTTTTTGTTTGCAAGCAGCAGATTACGCGCAGAAAAAAAGGATC
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    rep (pMB1)

910        920        930        940        950        960        970        980        990       1000
        *          *          *          *          *          *          *          *          *          *
901 TCAAGAAGATCCTTTGATCTTTTCTACGGGGTCTGACGCTCAGTGGAACGAAAACTCACGTTAAGGGATTTTGGTCATGAGATTATCAAAAAGGATCTTC
    <<<<<<<<<
    rep (pMB1)

1010       1020       1030       1040       1050       1060       1070       1080       1090       1100
        *          *          *          *          *          *          *          *          *          *
1001 ACCTAGATCCTTTTAAATTAAAAATGAAGTTTTAAATCAATCTAAAGTATATATGAGTAAACTTGGTCTGACAGTTACCAATGCTTAATCAGTGAGGCAC
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR
```

*Fig. 4C*

```
1101 CTATCTCAGCGATCTGTCTATTTCGTTCATCCATAGTTGCCTGACTCCCCGTCGTGTAGATAACTACGATACGGGAGGGCTTACCATCTGGCCCCAGTGC
     ampR 1201 TGCAATGATACCGCGAGAGACCCACGCTCACCGGCTCCAGATTTATCAGCAATAAACCAGCCAGCCGGAAGGGCCGAGCGCAGAAGTGGTCCTGCAACTTTA
     ampR 1301 TCCGCCTCCATCCAGTCTATTAATTGTTGCCGGGAAGCTAGAGTAAGTAGTTCGCCAGTTAATAGTTTGCGCAACGTTGTTGCCATTGCTACAGGCATCG
     ampR 1401 TGGTGTCACGCTCGTCGTTTGGTATGGCTTCATTCAGCTCCGGTTCCCAACGATCAAGGCGAGTTACATGATCCCCCATGTTGTGCAAAAAAGCGGTTAG
     ampR 1501 CTCCTTCGGTCCTCCGATCGTTGTCAGAAGTAAGTTGGCCGCAGTGTTATCACTCATGGTTATGGCAGCACTGCATAATTCTCTTACTGTCATGCCATCC
     ampR
```

Fig. 4D

```
        1410      1420      1430      1440      1450      1460      1470      1480      1490      1500
          *         *         *         *         *         *         *         *         *         *
1401 TGGTGTCACGCTCGTCGTTTGGTATGGCTTCATTCAGCTCCGGTTCCCAACGATCAAGGCGAGTTACATGATCCCCATGTTGTGCAAAAAGCGGTTAG
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1510      1520      1530      1540      1550      1560      1570      1580      1590      1600
          *         *         *         *         *         *         *         *         *         *
1501 CTCCTTCGGTCCTCCGATCGTTGTCAGAAGTAAGTTGGCCGCAGTGTTATCACTCATGGTTATGCAGCACTGCATAATTCTCTTACTGTCATGCCATCC
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1610      1620      1630      1640      1650      1660      1670      1680      1690      1700
          *         *         *         *         *         *         *         *         *         *
1601 GTAAGATGCTTTTCTGTGACTGGTGAGTACTCAACCAAGTCATTCTGAGAATAGTGTATGCGGCGACCGAGTTGCTCTTGCCCGGCGTCAATACGGGATA
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1710      1720      1730      1740      1750      1760      1770      1780      1790      1800
          *         *         *         *         *         *         *         *         *         *
1701 ATACCGCGCCACATAGCAGAACTTTAAAAGTGCTCATCATTGGAAAACGTTCTTCGGGGCGAAAACTCTCAAGGATCTTACCGCTGTTGAGATCCAGTTC
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1810      1820      1830      1840      1850      1860      1870      1880      1890      1900
          *         *         *         *         *         *         *         *         *         *
1801 GATGTAACCCACTGCACCCAACTGATCTTCAGCATCTTTTACTTTCACCAGCGTTTCTGGGTGAGCAAAAACAGGAAGGCAAAATGCCGCAAAAAAG
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR
```

*Fig. 4E*

```
             1910       1920       1930       1940       1950       1960       1970       1980       1990       2000
               *          *          *          *          *          *          *          *          *          *
1901 GGAATAAGGGCGACACGGAAATGTTGAATACTCATACTCTTCCTTTTTCAATATTATTGAAGCATTTATCAGGGTTATTGTCTCATGAGCGGATACATAT 2000
     <<<<<<<<<<<<<<<<<<<<<<<<<<<<<<<<<<<<<<<<<<<<<<<  >>>>>>>>>>>>>>>>>>>>>>>>>>>>>>>>>>>>>>>>>>>>>>>>>>>
     ampR                                                    seq1
                                                     <<<<<<<<<<<<<<<<<<<<<<<<<<<<<<<<<<<<<<<<<<<<<<<<<<<
                                                     ampr promoter 2010       2020       2030       2040
               *          *          *          *
2001 TTGAAATGTATTTAGAAAAATAAACAAATAGGGGTTCCGCG 2040
     <<<<<<<<<<<<<<<<<<<<<<<<<<<<<<<<<<<<<<<<
     ampr promoter
```

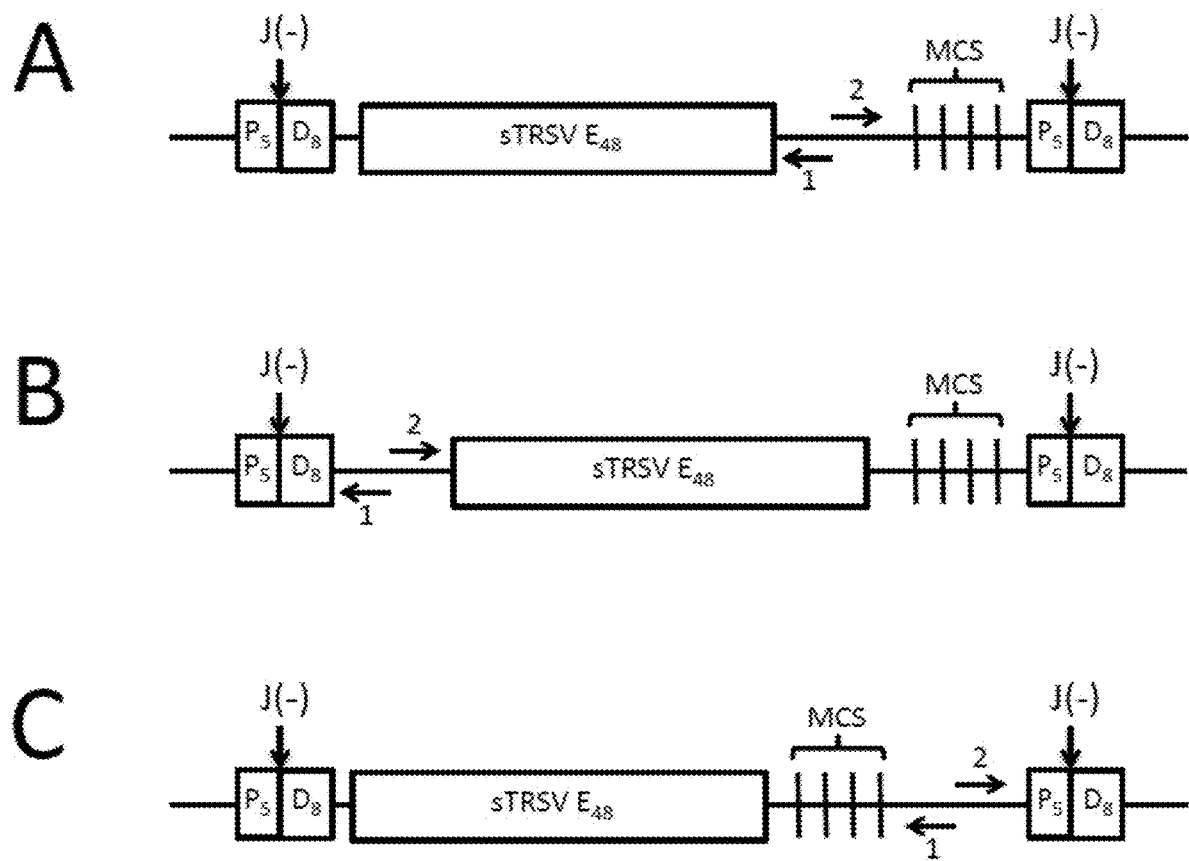
Fig. 16A-C

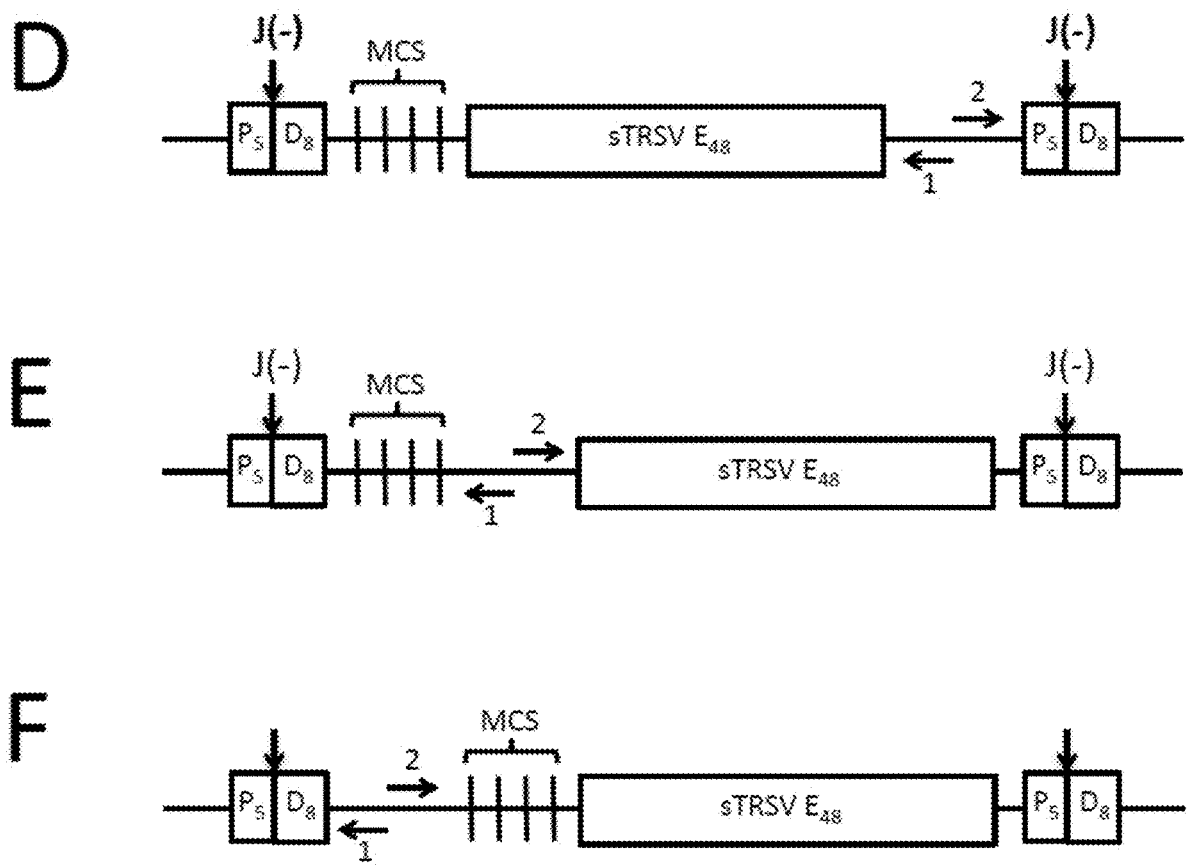
Fig. 16D-F

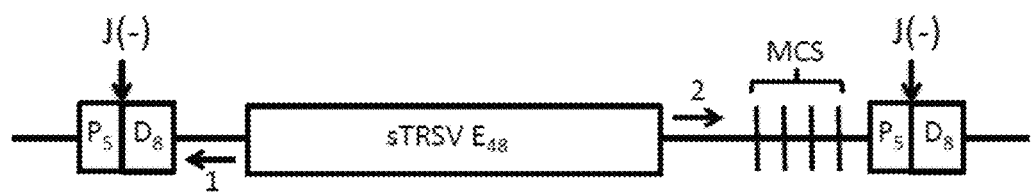
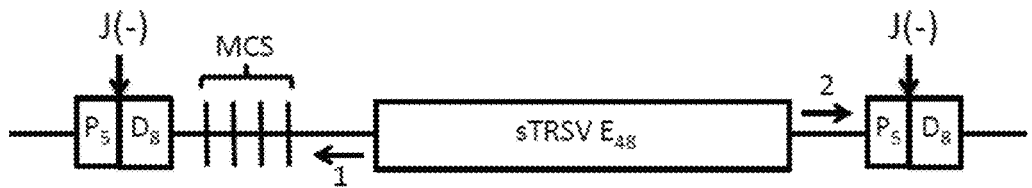
*Fig. 17A-B*

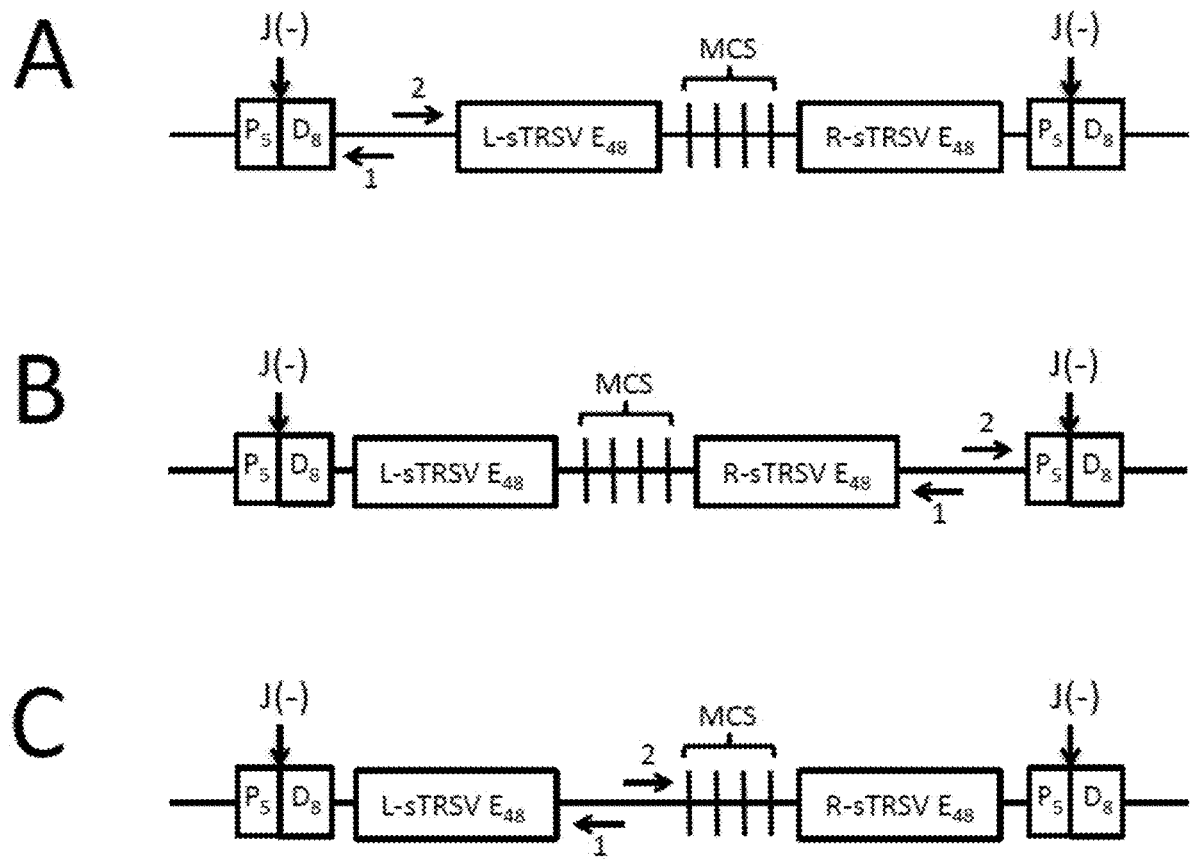
*Fig. 18A-C*

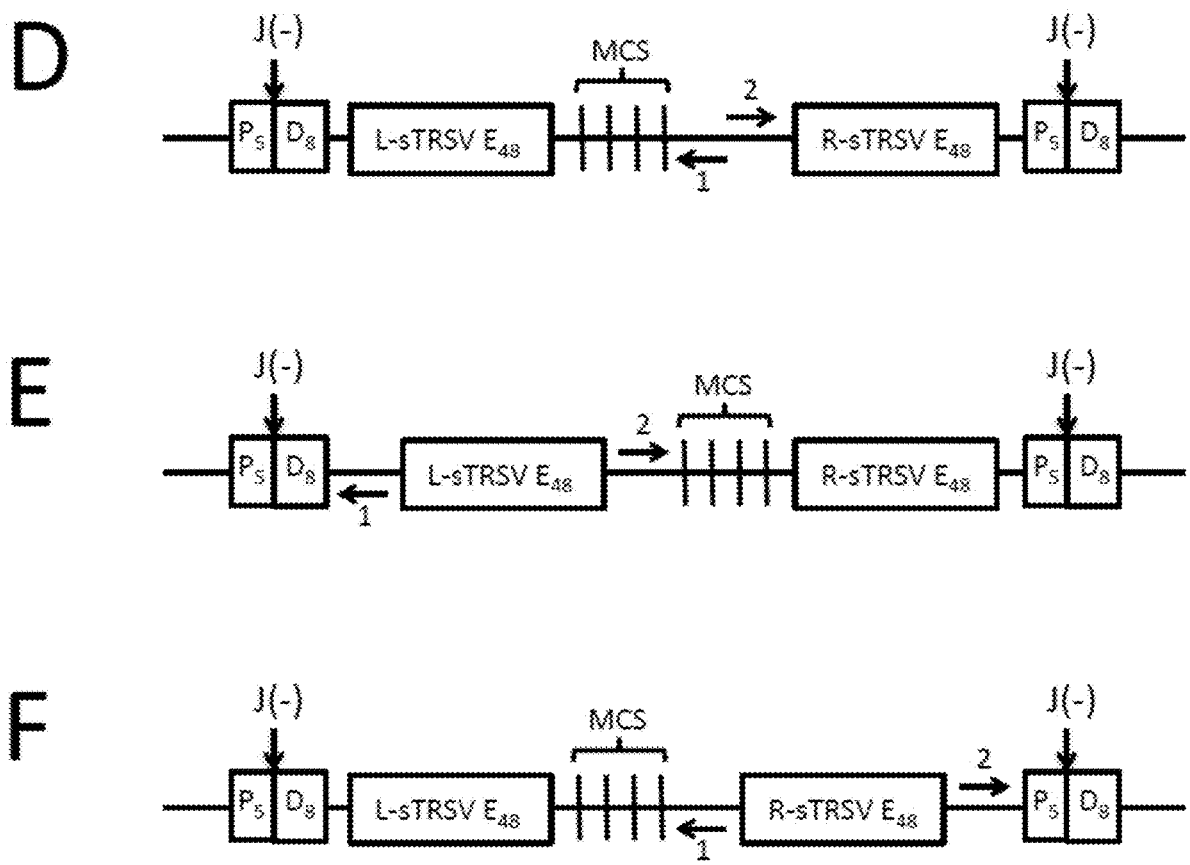
*Fig. 18D-F*

Improved T7 RNA polymerase promoters expressing the green fluorescent protein (GFP)

GFP expressed 2 hours after induction of T7 RNA polymerase

| | | | | | | |
|---|---|---|---|---|---|---|
| Predicted by transcription ratio | 1.00x | 1.51x | 1.68x | 2.40x | 2.69x | 2.81x |
| | Wildtype | Mutants (fold increase over wildtype) | | | | |
| Measured protein | 1.00x | 1.46x | 1.65x | 1.95x | 2.02x | 1.88x |

COMPOSITIONS AND METHODS FOR IDENTIFYING POLYNUCLEOTIDES OF INTEREST

CROSS-REFERENCE TO RELATED APPLICATIONS

This application is the U.S. National Phase of Intl. Appl. No. PCT/US2016/039348, filed on Jun. 24, 2016, which claims the benefit under 35 U.S.C. § 119(e) of U.S. Provisional Application No. 62/184,868, filed on Jun. 26, 2015, which are hereby incorporated herein by reference in their entireties for all purposes.

FIELD

Provided are constructs and methods useful for the screening and identification of polynucleotide sequences of interest, in particular promoters, RNA stability modifying sequences and transcriptional modifying sequences.

SEQUENCE LISTING

The instant application contains a Sequence Listing which has been submitted electronically in ASCII format and is hereby incorporated by reference in its entirety. Said ASCII copy, created on Jun. 23, 2016, is named UCDVP115WO_sequencelisting.txt and is 11,109 kilobytes in size.

BACKGROUND

Currently available technologies for identifying sequences of interest, including promoters, transcriptional modifiers and RNA stability sequences, consist of computer annotation of sequenced genomes to find expressed regions. Generally, the sequence flanking the 5'end of an expressed sequence is "identified" as the promoter. This analysis is often paired with RNA sequencing which identifies the starts of the transcription. These methods do not yield the cloned promoter or allow promoter mutations to be evaluated.

SUMMARY

In one aspect, provided is a DNA plasmid useful for identifying a promoter. In some embodiments, the DNA plasmid comprises operably linked polynucleotides encoding: (a) a mini-monomer cassette, comprising a first ribozyme cleavage site and a second ribozyme cleavage site, and comprising between the first ribozyme cleavage site and the second ribozyme cleavage site: (i) a ribozyme catalytic core; (ii) a multiple cloning site polynucleotide comprising plurality of restriction endonuclease cleavage sites; and (iii) a reverse primer annealing polynucleotide located upstream or 5' to a forward primer annealing polynucleotide; and (b) a plasmid backbone, comprising an origin of replication. In some embodiments, the DNA plasmid comprises operably linked polynucleotides encoding: (a) a mini-monomer cassette, comprising in the 5' to 3' direction: (i) a first ribozyme cleavage site; (ii) a ribozyme catalytic core; (iii) a multiple cloning site polynucleotide comprising plurality of restriction endonuclease cleavage sites, a reverse primer annealing polynucleotide and a forward primer annealing polynucleotide; and (iv) a second ribozyme cleavage site; and (b) a plasmid backbone, comprising an origin of replication.

In a further aspect, provided is a DNA plasmid useful for identifying a promoter. In some embodiments, the DNA plasmid comprises operably linked polynucleotides encoding: (a) a mini-monomer cassette, comprising a first ribozyme cleavage site and a second ribozyme cleavage site, and comprising between the first ribozyme cleavage site and the second ribozyme cleavage site: (i) a ribozyme catalytic core; (ii) a reverse primer annealing polynucleotide; (iii) a forward primer annealing polynucleotide; and (iv) an inserted polynucleotide suspected of comprising a promoter; and (b) a plasmid backbone, comprising an origin of replication. In some embodiments, the DNA plasmid comprises operably linked polynucleotides encoding: (a) a mini-monomer cassette, comprising in the 5' to 3' direction: (i) a first ribozyme cleavage site; (ii) a ribozyme catalytic core; (iii) a reverse primer annealing polynucleotide; (iv) a forward primer annealing polynucleotide; (v) an inserted polynucleotide suspected of comprising a promoter; (vi) a second ribozyme cleavage site; (b) a plasmid backbone, comprising an origin of replication. In varying embodiments of the DNA plasmid, the polynucleotide suspected of comprising a promoter has from about 50 nucleotides or base pairs (bp) to about 2000 bp, e.g., from about 100 bp to about 1000 bp. In varying embodiments, the primer annealing polynucleotides are reverse transcriptase polymerase chain reaction (RT-PCR) primer annealing polynucleotides.

In varying embodiments of the DNA plasmid useful for identifying a promoter, the second ribozyme cleavage site is capable of being transcribed into RNA by a RNA polymerase when the inserted polynucleotide comprises a functional promoter. In varying embodiments, the promoter in the inserted polynucleotide suspected of comprising a promoter is functional in a eukaryotic cell. In varying embodiments, the promoter in the inserted polynucleotide suspected of comprising a promoter is functional in a prokaryotic cell. In varying embodiments, the inserted polynucleotide suspected of comprising a promoter is from a library of randomized chemically synthesized DNA sequences. In varying embodiments, the inserted polynucleotide suspected of comprising a promoter is from a genomic DNA library. In varying embodiments, the inserted polynucleotide suspected of comprising a promoter comprises a mutagenized promoter. In varying embodiments, the plasmid has from about 1800 bp to about 3800 bp, e.g., from about 1900 bp to about 2900 bp. In varying embodiments, the plasmid backbone does not comprise a promoter functional in a eukaryotic cell. In varying embodiments, the ribozyme catalytic core is derived from a hairpin ribozyme. In varying embodiments, the ribozyme catalytic core is derived from the negative strand self-cleavage domain (e.g., a hairpin ribozyme catalytic core) of a satellite RNA of a plant virus selected from the group consisting of the satellite RNA of tobacco ringspot virus (sTRSV), the satellite RNA of arabis mosaic virus (sArMV), and the satellite RNA of chicory yellow mottle virus (sCYMV). In varying embodiments, the ribozyme catalytic core is derived from the negative strand self-cleavage domain of the satellite RNA of tobacco ringspot virus (sTRSV). In varying embodiments, the ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 8. In varying embodiments, the ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 3. In varying embodiments, the ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 4. In varying embodiments, the ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 5. In varying embodiments, the first, second and/or third ribozyme cleavage sites are hairpin ribozyme cleavage sites or sites cleavable by a hairpin ribozyme catalytic core. In varying embodiments, the first, second and/or third ribozyme cleavage sites have a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 7. In varying embodiments, the first, second and/or third ribozyme cleavage sites have a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 6. In varying embodiments, the plasmid does not comprise upstream of or 5' to the mini-monomer cassette, a promoter functional in a prokaryotic cell that promotes the transcription of the mini-monomer cassette in the sense orientation. In varying embodiments, the plasmid further comprises a control promoter. In varying embodiments, the control promoter is functional in a prokaryotic cell. In varying embodiments, the control promoter is positioned upstream of or 5' to the mini-monomer cassette. In varying embodiments, the promoter functional in a prokaryotic cell comprises a bacteriophage promoter, e.g., selected from the group consisting of T7, T3 and SP6. In varying embodiments, the plasmid or plasmid backbone comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 1. In varying embodiments, the plasmid backbone comprises an expression cassette encoding a selection marker. In varying embodiments, the expression cassette is in the antisense orientation from the ribozyme catalytic core. In varying embodiments, the expression cassette is in the sense orientation to the ribozyme catalytic core. In varying embodiments, the selection marker comprises a polynucleotide encoding a gene or protein conferring antibiotic resistance, heat tolerance, fluorescence, luminescence or rescue of auxotrophic growth for specific amino acids or nucleotides. In varying embodiments, the step of transcribing the population of plasmids into RNA is performed in the presence and absence of an adjusted external factor. In varying embodiments, the adjusted external factor is selected from the group consisting of temperature, pH, ion concentrations, ionic strength, salt concentration, calcium concentration, endoplasmic reticulum stress, hormones and ligands, heavy metals, toxins, glucose, the presence of virus, fungi, bacteria or other pathogens.

In a further aspect, provided are methods of identifying functional promoter sequences. In some embodiments, the methods comprise:

a) providing a population of plasmids as described above and herein;

b) transcribing the population of plasmids into RNA; wherein the second ribozyme cleavage site is transcribed by a RNA polymerase when the inserted polynucleotide comprises a functional promoter; wherein RNA transcripts comprising the mini-monomer cassette self-cleave from the transcript, thereby forming a population of circularized RNA transcripts of self-cleaved mini-monomer cassettes;

c) reverse transcribing into cDNA the population of circularized RNA transcripts of self-cleaved mini-monomer cassettes, thereby forming a population of cDNA reverse-transcripts of self-cleaved mini-monomer cassettes; and d) sequencing the inserted polynucleotides comprising a functional promoter in the population of cDNA reverse-transcripts of self-cleaved mini-monomer cassettes, whereby functional promoter sequences are identified. In varying embodiments, the step of transcribing the population of plasmids into RNA is performed in vitro. In varying embodiments, the step of transcribing the population of plasmids into RNA is performed in vivo. In varying embodiments, the functional promoter is functional in a eukaryotic cell. In varying embodiments, the functional promoter is functional in a prokaryotic cell. In varying embodiments, the methods further comprise, after step b), the step of purifying or isolating RNA from non-RNA. In varying embodiments, the methods further comprise, after step b), the step of purifying or isolating the population of circularized RNA transcripts of self-cleaved mini-monomer cassettes. In some embodiments, the reverse transcribing step comprises amplifying from the forward and reverse primer annealing polynucleotides. In some embodiments, the sequencing step comprises deep sequencing. In some embodiments, statistical analyses of a population of RT-PCR products are performed and the identified promoters are ordered by strength. In some embodiments, the sequencing step comprises amplifying from the forward and reverse primer annealing polynucleotides (e.g., for PCR or RT-PCR).

In a related aspect, provided is a DNA plasmid useful for identifying a RNA stability modifier or a transcription modifier. In some embodiments, the DNA plasmid comprises operably linked polynucleotides encoding in the 5' to 3' direction:

(a) a test promoter, wherein the test promoter is functional in a eukaryotic cell or in a prokaryotic cell;

(b) a mini-monomer cassette, comprising:
  (i) a first ribozyme cleavage site;
  (ii) a ribozyme catalytic core;
  (iii) a reverse primer annealing polynucleotide (e.g., for PCR or RT-PCR);
  (iv) a forward primer annealing polynucleotide (e.g., for PCR or RT-PCR);
  (v) an inserted polynucleotide suspected of comprising a RNA stability modifier or a transcription modifier;
  (vi) a second ribozyme cleavage site;

(c) a plasmid backbone comprising an origin of replication.

In another aspect, provided is a DNA plasmid useful for identifying a RNA stability modifier or a transcription modifier. In some embodiments, the DNA plasmid comprises operably linked polynucleotides encoding in the 5' to 3' direction:

(a) a test promoter, wherein the test promoter is functional in a eukaryotic cell or in a prokaryotic cell;

(b) a first mini-monomer cassette, comprising:
  (i) a first ribozyme cleavage site;
  (ii) a first ribozyme catalytic core;
  (iii) a first reverse primer annealing polynucleotide;
  (iv) a first forward primer annealing polynucleotide;
  (v) a barcode polynucleotide
  (vi) a second ribozyme cleavage site;

(c) a second mini-monomer cassette, comprising:
  (i) the second ribozyme cleavage site;
  (ii) a second ribozyme catalytic core;

(iii) a second reverse primer annealing polynucleotide;
(iv) a second forward primer annealing polynucleotide;
(v) an inserted polynucleotide suspected of comprising a RNA stability modifier or a transcription modifier;
(vi) a third ribozyme cleavage site;
(d) a plasmid backbone comprising an origin of replication. In varying embodiments, the barcode polynucleotide comprises a random DNA sequence comprising from about 10 to about 20 N residues. In varying embodiments, the primer annealing polynucleotides are reverse transcriptase polymerase chain reaction (RT-PCR) primer annealing polynucleotides.

In varying embodiments of the DNA plasmid useful for identifying a RNA stability modifier or a transcription modifier, the polynucleotide suspected of comprising a RNA stability modifier or a transcription modifier has from about 50 bp to about 1000 bp. In varying embodiments, the polynucleotide suspected of comprising a RNA stability modifier or a transcription modifier comprises an enhancer. In varying embodiments, the inserted polynucleotide suspected of comprising a RNA stability modifier or a transcription modifier is located 5' of the first ribozyme cleavage site. In varying embodiments, the promoter functional in a eukaryotic cell comprises a promoter from the same species as the inserted polynucleotide suspected of comprising a RNA stability modifier or a transcription modifier. In some embodiments, the inserted polynucleotide suspected of comprising a RNA stability modifier or a transcription modifier is from a library of randomized chemically synthesized DNA sequences. In varying embodiments, the inserted polynucleotide suspected of comprising a RNA stability modifier or a transcription modifier is from a genomic DNA library. In varying embodiments, the inserted polynucleotide suspected of comprising a RNA stability modifier or a transcription modifier comprises a mutagenized RNA stability modifier or a transcription modifier. In varying embodiments, the first and second ribozyme catalytic cores are independently derived from first and second hairpin ribozymes. In varying embodiments, the first and second ribozyme catalytic cores are independently derived from the negative strand self-cleavage domain (e.g., a hairpin ribozyme catalytic core) of a plant virus satellite RNA selected from the group consisting of the satellite RNA of tobacco ringspot virus (sTRSV), the satellite RNA of arabis mosaic virus (sArMV), and the satellite RNA of chicory yellow mottle virus (sCYMV). In some embodiments, the first and second ribozyme catalytic cores are different. In varying embodiments, the first and second ribozyme catalytic cores are the same. In varying embodiments, the first or second ribozyme catalytic core is derived from the negative strand self-cleavage domain the satellite RNA of tobacco ringspot virus (sTRSV). In varying embodiments, the first and/or second ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 8. In varying embodiments, the first and/or second ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 3. In varying embodiments, the first and/or second ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 4. In varying embodiments, the first and/or second ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 5. In varying embodiments, the first, second and/or third ribozyme cleavage sites are hairpin ribozyme cleavage sites or sites cleavable by a hairpin ribozyme catalytic core. In varying embodiments, the first, second and/or third ribozyme cleavage sites comprise a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 7. In varying embodiments, the first, second and/or third ribozyme cleavage sites have a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 6. In varying embodiments, the plasmid or plasmid backbone comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 2. In varying embodiments, the plasmid does not comprise upstream of or 5' to the mini-monomer cassette, a promoter functional in a prokaryotic cell that promotes the transcription of the mini-monomer cassette in the sense orientation. In varying embodiments, the plasmid further comprises a control promoter. In varying embodiments, the control promoter is functional in a prokaryotic cell. In varying embodiments, the control promoter is positioned upstream of or 5' to the mini-monomer cassette. In varying embodiments, the promoter functional in a prokaryotic cell comprises a bacteriophage promoter, e.g., selected from the group consisting of T7, T3 and SP6. In varying embodiments, the plasmid backbone comprises an expression cassette encoding a selection marker. In varying embodiments, the expression cassette is in the antisense orientation from the ribozyme catalytic core. In varying embodiments, the expression cassette is in the sense orientation to the ribozyme catalytic core. In varying embodiments, the selection marker comprises a polynucleotide encoding a gene or protein conferring antibiotic resistance, heat tolerance, fluorescence, luminescence or rescue of auxotrophic growth for specific amino acids or nucleotides. In varying embodiments, the promoter functional in a eukaryotic cell is located 3' of the third ribozyme cleavage site. In such embodiments, the plasmid has from about 1800 bp to about 3800 bp, e.g., from about 1900 bp to about 2900 bp. In varying embodiments, the promoter functional in a eukaryotic cell is located 5' of the first ribozyme cleavage site. In such embodiments, the construct has no upper size limit, but the plasmid optionally can have from about 2100 bp to about 3100 bp, e.g., from about 2100 bp to about 2250 bp.

In a further aspect, provided are methods of identifying RNA stability modifying and/or transcription modifying sequences. In some embodiments, the method comprises:

a) providing a population of plasmids useful for identifying a RNA stability modifier or a transcription modifier as described above and herein;

b) sequencing the first and second mini-monomer cassettes; thereby linking the barcode polynucleotide to a unique inserted polynucleotide suspected of comprising a RNA stability modifier;

c) transcribing in vitro the population of plasmids into RNA from a control promoter (e.g., a promoter functional in a prokaryotic cell), wherein RNA transcripts comprising the first and second mini-monomer cassettes self-cleave from the transcript;

d) sequencing the self-cleaved first and second mini-monomer cassettes transcribed in vitro in step c); thereby controlling for cleavage and circularization efficiency;

e) transcribing either in vitro or in a population of host cells the population of plasmids into RNA from a test promoter, wherein the test promoter is functional in a eukaryotic cell or in a prokaryotic cell, wherein RNA transcripts comprising the first and second mini-monomer cassettes self-cleave from the transcript;

f) sequencing the self-cleaved first and second mini-monomer cassettes transcribed in step e);

g) comparing the relative abundance or frequency of the self-cleaved second mini-monomer cassettes transcribed in vitro in step c) with the self-cleaved second mini-monomer cassettes transcribed in step e), wherein a higher or increased relative abundance or frequency of the self-cleaved second mini-monomer cassettes transcribed in step e) identifies RNA stabilizing sequences or transcription enhancer sequences in the second mini-monomer cassette, and wherein a lower or decreased relative abundance or frequency of the self-cleaved second mini-monomer cassettes transcribed in step e) identifies RNA destabilizing sequences or transcription reduction sequences in the second mini-monomer cassette; and h) comparing the ratios of the relative abundance or frequency of the self-cleaved first mini-monomers to their linked self-cleaved second mini-monomers produced in vitro in step c) with those produced in step e), wherein a substantially unchanged and/or a substantially 1:1 ratio, and an increased relative abundance or frequency of the self-cleaved second mini-monomer cassettes transcribed in step e) identifies a transcriptional enhancer;

wherein a ratio showing a higher relative abundance of the self-cleaved second mini-monomer, and an increased relative abundance or frequency of the self-cleaved second mini-monomer cassettes transcribed in step e) identifies a RNA stabilizing sequence;

wherein a substantially unchanged and/or a substantially 1:1 ratio, and a decreased relative abundance or frequency of the self-cleaved second mini-monomer cassettes transcribed in step e) identifies a transcriptional reducing sequence; and wherein a ratio showing a lower relative abundance of the self-cleaved second mini-monomer, and a decreased relative abundance or frequency of the self-cleaved second mini-monomer cassettes transcribed in a host cell in step g) identifies a RNA destabilizing sequence.

In a further aspect, provided are methods of identifying a polynucleotide sequence bound by a transcription factor, comprising:

a) providing a population of plasmids as described above and herein for use in identifying RNA stability/transcription modifying sequences;

b) sequencing the first and second mini-monomer cassettes; thereby linking the barcode polynucleotide to a unique inserted polynucleotide suspected of comprising a RNA stability modifier;

c) transcribing in vitro the population of plasmids into RNA from the control promoter (e.g., a promoter functional in a prokaryotic cell), wherein RNA transcripts comprising the first and second mini-monomer cassettes self-cleave from the transcript;

d) sequencing the self-cleaved first and second mini-monomer cassettes transcribed in vitro; thereby controlling for cleavage and circularization efficiency;

e) transcribing the population of plasmids into RNA from the test promoter (e.g., a promoter functional in a eukaryotic or a prokaryotic cell), wherein the transcribing is performed in a population of host cells and in the presence and absence of an inhibitory nucleic acid that inhibits or reduces the expression of the transcription factor, wherein RNA transcripts comprising the first and second mini-monomer cassettes self-cleave from the transcript;

f) sequencing the self-cleaved first and second mini-monomer cassettes transcribed in a host cell;

g) comparing the relative abundance or frequency of the self-cleaved second mini-monomer cassettes transcribed in the host cell in the presence of the inhibitory nucleic acid with the self-cleaved second mini-monomer cassettes transcribed in a host cell in the absence of the inhibitory nucleic acid, wherein a higher or increased relative abundance or frequency of the self-cleaved second mini-monomer cassettes transcribed in a host cell in the absence of the inhibitory nucleic acid identifies the polynucleotide sequence bound by the transcription factor. In varying embodiments, the inhibitory nucleic acid is an interfering RNA polynucleotide (RNAi).

In varying embodiments of the methods, the step of transcribing the population of plasmids into RNA is performed in the presence and absence of an adjusted external factor. In varying embodiments, the adjusted external factor is selected from the group consisting of temperature, pH, ion concentrations, ionic strength, salt concentration, calcium concentration, endoplasmic reticulum stress, hormones and ligands, heavy metals, toxins, glucose, the presence of virus, fungi, bacteria or other pathogens. In varying embodiments, the methods further comprise, after step c), the step of purifying or isolating RNA from non-RNA. In varying embodiments, the methods further comprise, after step c), the step of purifying or isolating the population of circularized RNA transcripts of self-cleaved mini-monomer cassettes. In varying embodiments, the reverse-transcribing step comprises amplifying from the first forward and reverse primer annealing polynucleotides (e.g., for PCR or RT-PCR) and the second forward and reverse primer annealing polynucleotides (e.g., for PCR or RT-PCR), respectively. In varying embodiments, the sequencing step comprises deep sequencing. In varying embodiments, the sequencing step comprises amplifying from the first forward and reverse primer annealing polynucleotides (e.g., for PCR or RT-PCR) and the second forward and reverse primer annealing polynucleotides (e.g., for PCR or RT-PCR), respectively. In varying embodiments, statistical analyses of a population of RT-PCR products are performed and the identified RNA stability modifying and/or transcription modifying sequences are ordered by strength.

In a further aspect, provided is a host cell or a population of host cells comprising a DNA plasmid or a population of DNA plasmids, as described above and herein. In varying embodiments, the host cell or population of host cells is a prokaryotic cell or a eukaryotic cell. In varying embodiments, the host cell or population of host cells is selected from an archael cell, a bacterial cell, an animal cell (e.g., a mammalian cell or an insect cell), a plant cell, or a fungal cell.

In a further aspect, provided are kits comprising one or more plasmids or one or more populations of plasmids, as described above and herein.

In a further aspect, provided is a polynucleotides comprising one or more promoters selected from the group consisting of SEQ ID NOs: 10-73473. Also provided is an expression cassette comprising one or more promoters selected from the group consisting of SEQ ID NOs: 10-73473. Also provided is a plasmid comprising an expression cassette comprising one or more promoters selected from the group consisting of SEQ ID NOs: 10-73473. Also provided is a host cell or a population of host cells, each comprising an expression cassette comprising one or more promoters selected from the group consisting of SEQ ID NOs: 10-73473. In some embodiments, the expression cassette is in a plasmid. In some embodiments, the expression cassette is incorporated into the genome of the host cell. In some embodiments, the host cell is selected from an archael cell, a bacterial cell, an animal cell, a plant cell, or a fungal cell.

In a further aspect, provided are methods for producing an RNA polynucleotide of interest. In some embodiments, the methods comprise expressing an RNA molecule from a polynucleotide operably linked to one or more promoters selected from the group consisting of SEQ ID NOs: 10-73473. In varying embodiments, the RNA molecule encodes a protein. In varying embodiments, the RNA molecule is non-coding RNA. In varying embodiments, the RNA molecule is selected from the group consisting of mRNA, rRNA, tRNA, guide RNA and micro RNA. In varying embodiments, the method is performed in vivo (e.g., in a cell) or in vitro.

Definitions

The term "RNA stability modifier" refers to a DNA motif that modulates (e.g., increases or decreases) the rate of degradation of the RNA and thus change the half-life of the RNA. Mechanisms include binding of proteins or polynucleotides to the "RNA stability modifier" that create this change (e.g., in iron regulation or in cells exposed to hormones). See, e.g., Addess, et al., *J. Mol. Biol.* 274 (1): 72-83. Reference to "RNA stability modifier" includes polynucleotides that bind a polynucleotide involved in decreasing RNA stability thus increasing RNA turnover, double stranded polynucleotides that are cleaved by a RNAse (e.g., Dicer) and transcriptional terminators.

The term "transcription modifier" refers to a DNA motif that modulates (e.g., increases or decreases) promoter strength.

As used herein, "promoter strength" or "promoter efficiency" interchangeably refer to the number completed transcripts per unit time which is obtained by sequencing the RT-PCR product population.

The term "enhancer" refers to a DNA motif that increases promoter strength. Enhancers recruit transcription factors to bind in the vicinity of promoters, thus increasing effectiveness of the promoter or promoter specificity to certain external factors (light, hormones, etc.).

The term "repressor" refers to a DNA motif that decreases promoter strength. Repressors recruit transcription factors to bind in the vicinity of promoters, thus decreasing effectiveness of the promoter or promoter specificity to certain external factors (light, hormones, etc.).

The term "mini-monomer cassette" refers to a polynucleotide sequence comprising a ribozyme catalytic core and upstream and downstream ribozyme cleavage sites, such that when transcribed into RNA, the ribozyme catalytic core self-cleaves the mini-monomer cassette at the upstream and downstream ribozyme cleavage sites out of the context of a longer polynucleotide. The 5' and 3' ends of the excised polynucleotide ligate to form a circularized polynucleotide.

The term "ribozyme catalytic core" refers to the subsequence of a ribozyme capable of carrying out cleavage of a RNA molecule.

The term "ribozyme cleavage site" refers to the sequences recognized and cleaved by a ribozyme catalytic core.

The terms "identical" or percent "identity," and variants thereof in the context of two or more polynucleotide or two or more amino acid sequences, refer to two or more sequences or subsequences that are the same. Sequences are "substantially identical" if they have a specified percentage of nucleic acid residues or amino acid residues that are the same (i.e., at least 60% identity, optionally at least 65%, 70%, 75%, 80%, 85%, 90%, 95%, 96%, 97%, 98%, or 99% identity to a reference sequence (e.g., SEQ ID NOs: 1-73473) over a specified region (or the whole reference sequence when not specified)), when compared and aligned for maximum correspondence over a comparison window, or designated region as measured using any sequence comparison algorithm known in the art (GAP, BESTFIT, BLAST, Align, FASTA, and TFASTA in the Wisconsin Genetics Software Package, Genetics Computer Group (GCG), 575 Science Dr., Madison, Wis.), Karlin and Altschul Proc. Natl. Acad. Sci. (U.S.A.) 87:2264-2268 (1990) set to default settings, or by manual alignment and visual inspection (see, e.g., Ausubel et al., Current Protocols in Molecular Biology (1995-2014). Optionally, the identity exists over a region that is at least about 100, 200, 300, 400, 500, 600, 800, 1000, or more, nucleic acids in length, or over the full-length of the sequence.

BRIEF DESCRIPTION OF THE DRAWINGS

FIGS. 2A-E illustrate an annotated polynucleotide sequence of a vector map for a plasmid useful for screening for promoters.

FIG. 4A-F illustrate an annotated polynucleotide sequence of a vector map for a plasmid useful for screening for RNA stability modifiers and/or transcription modifiers.

FIGS. 16A-F illustrate six functional arrangements between the ribozyme cleavage sites of the ribozyme core, MCS that will contain the test promoter sequence, and the primer 1 and 2 sequences, where the primer 1 and 2 sequences are adjacent to each other. When these illustrative mini-monomer cassettes are transcribed, ribozyme cleaved and ligated, reverse-transcribed and PCR amplified the test promoter sequence is recovered.

FIGS. 17A-B illustrate two additional functional arrangements between the ribozyme cleavage sites of the ribozyme core, MCS that will contain the test promoter sequence, and the primer 1 and 2 sequences, where the primer 1 and 2 sequences are not adjacent to each other. When these illustrative mini-monomer cassettes are transcribed, ribozyme cleaved and ligated, reverse-transcribed and PCR amplified, the test promoter sequence is recovered.

FIGS. 18A-F illustrate six functional arrangements between the ribozyme cleavage sites in which the MCS (with or without comprising an insert comprising a test promoter sequence) is inserted into loop 2 of stem 4 (see, FIG. 5) of the ribozyme core and the primer 1 and 2 sequences, where the primer 1 and 2 sequences are either adjacent to each other (FIG. 18A-D) or are not adjacent to each other (FIG. 18E-F). L-sTRSV $E_{48}$ and R-sTRSVE$_{48}$ represent the left and right halves of the ribozyme catalytic core respectively. When these illustrative mini-monomer cassettes are transcribed, ribozyme cleaved and ligated, reverse-transcribed and PCR amplified, the test promoter sequence is recovered.

Due to the number of sequences shown, the y-axis is a log axis to compress its length. Of the unique double mutants possible, an analysis of 1223 out of the possible 1224 is shown (99.9%).

Figure 21:
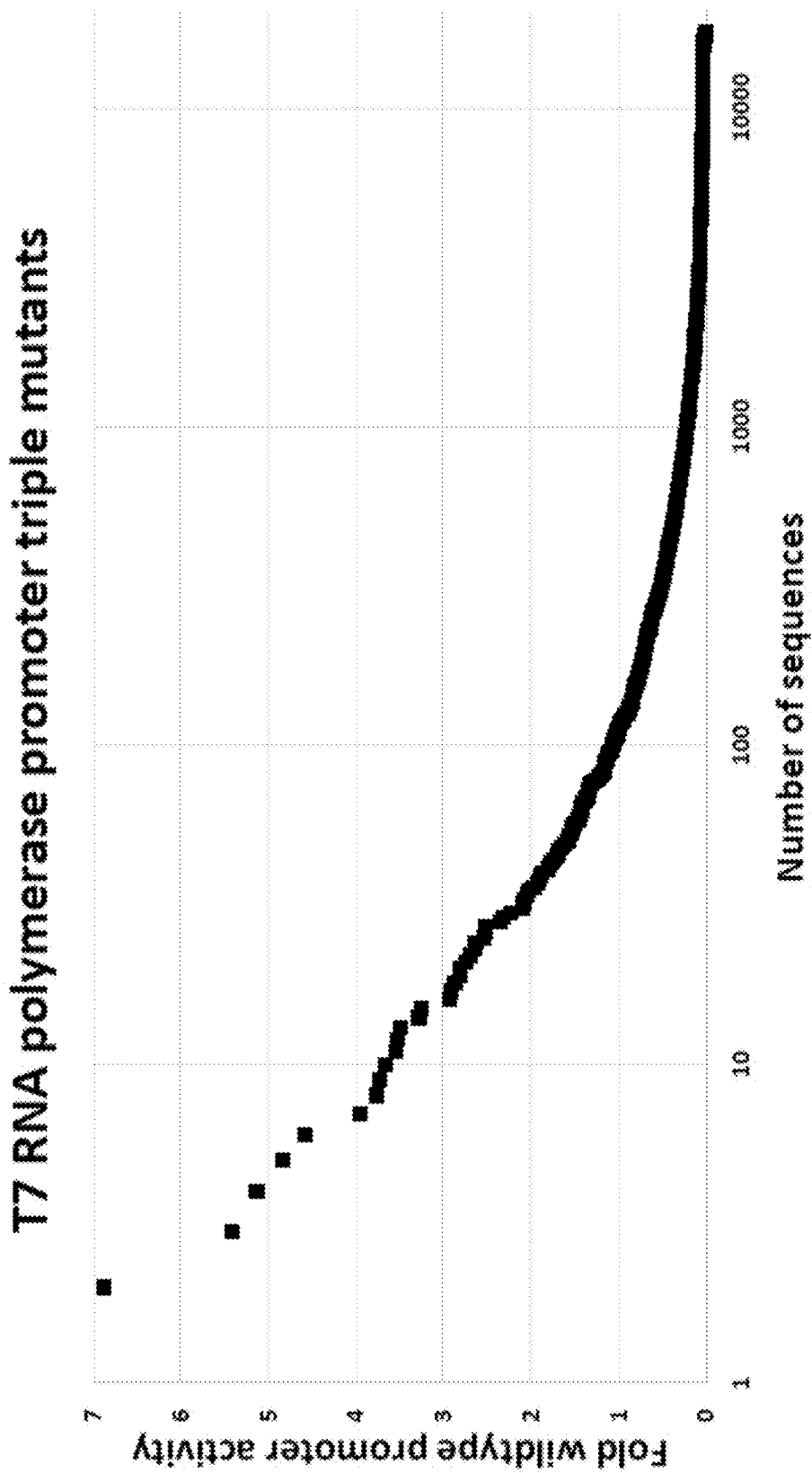

FIG. 21 illustrates the relative in vivo activity of 17281 triple mutants of the mutated T7 RNA polymerase promoter whose construction is described in Example 4. Mutant promoter activity is shown on the y-axis and is normalized to the wildtype promoter activity as described in Example 4. The triple mutants were placed in activity order from highest to lowest relative to wildtype. The number of individual triple mutants analyzed is shown on the x-axis. Due to the number of sequences shown, the y-axis is a log axis to compress its length. Of the unique triple mutants possible, an analysis of 17281 out of the possible 18340 is shown (94.1%).

FIG. 22 illustrates the measured transcription ratios and their relationship to in vivo protein expression levels for 5 selected mutant T7 RNA polymerase promoters. Constructions containing the coding sequence for the green fluorescent protein (GFP) downstream of the selected mutant T7 RNA polymerase promoters were made and inserted into T7 RNA polymerase-expressing cells. Induction of T7 RNA polymerase activity was done in vivo for 2 hours, just as was done for the expression at the time of mini-monomer RNA production as part of the mutant promoter activity assay. Protein was extracted and run on a SDS-polyacrylamide gel, transferred to a PVDF membrane, and an immunoblot was done with anti-GFP antibodies. The gel was scanned and the area under the peak of detected protein was estimated with the image analysis software package, ImageJ. See, e.g., Rasband, W. S., ImageJ, U. S. National Institutes of Health, Bethesda, Md., USA, http://imagej.nih.gov/ij/, 1997-2016. A comparison of the ratio of transcription and the amount of protein produced by the mutant and wildtype T7 RNA polymerase promoters is shown. This comparison shows good agreement for the first two selected promoters, but deviates somewhat for the last three. It is likely that this is due to the narrow linear range of immunoblots.

Figure 23:
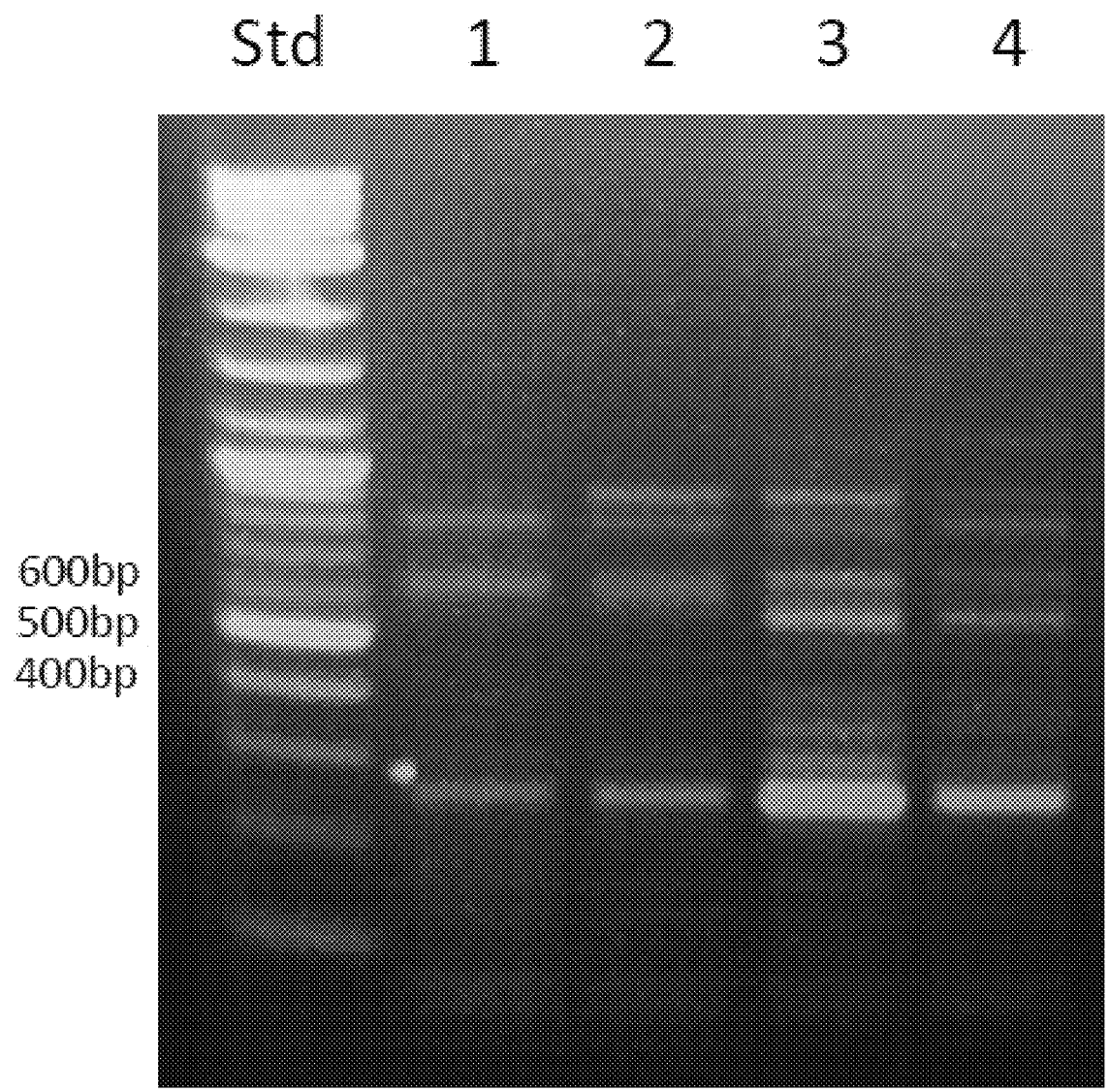

FIG. 23 illustrates RT-PCR of mini-monomer RNAs from yeast constructs containing either the known yeast (*Saccharomyces cerevisiae*) TEF promoter or a fragment of the GFP gene in a yeast 2 micron vector containing a mini-monomer cassette. Extracted yeast total RNA was extracted, reverse transcribed and subjected to 35 cycles of PCR with primers 1 and 2 (e.g., reverse and forward primer annealing polynucleotides, respectively). The appropriate sized fragment should be 595 base pairs long. This band is only seen in the RNA samples from the yeast containing the TEF promoter in the mini-monomer cassette. Lanes: (Std) 2-Log DNA ladder from New England Biolabs; (1) Total yeast RNA from mini-monomer construct containing the GFP coding sequence; (2) Duplicate total yeast RNA from mini-monomer construct containing the GFP coding sequence; (3) Total yeast RNA from mini-monomer construct containing the known yeast TEF promoter; (4) Duplicate total yeast RNA from mini-monomer construct containing the known yeast TEF promoter.

Figure 24:
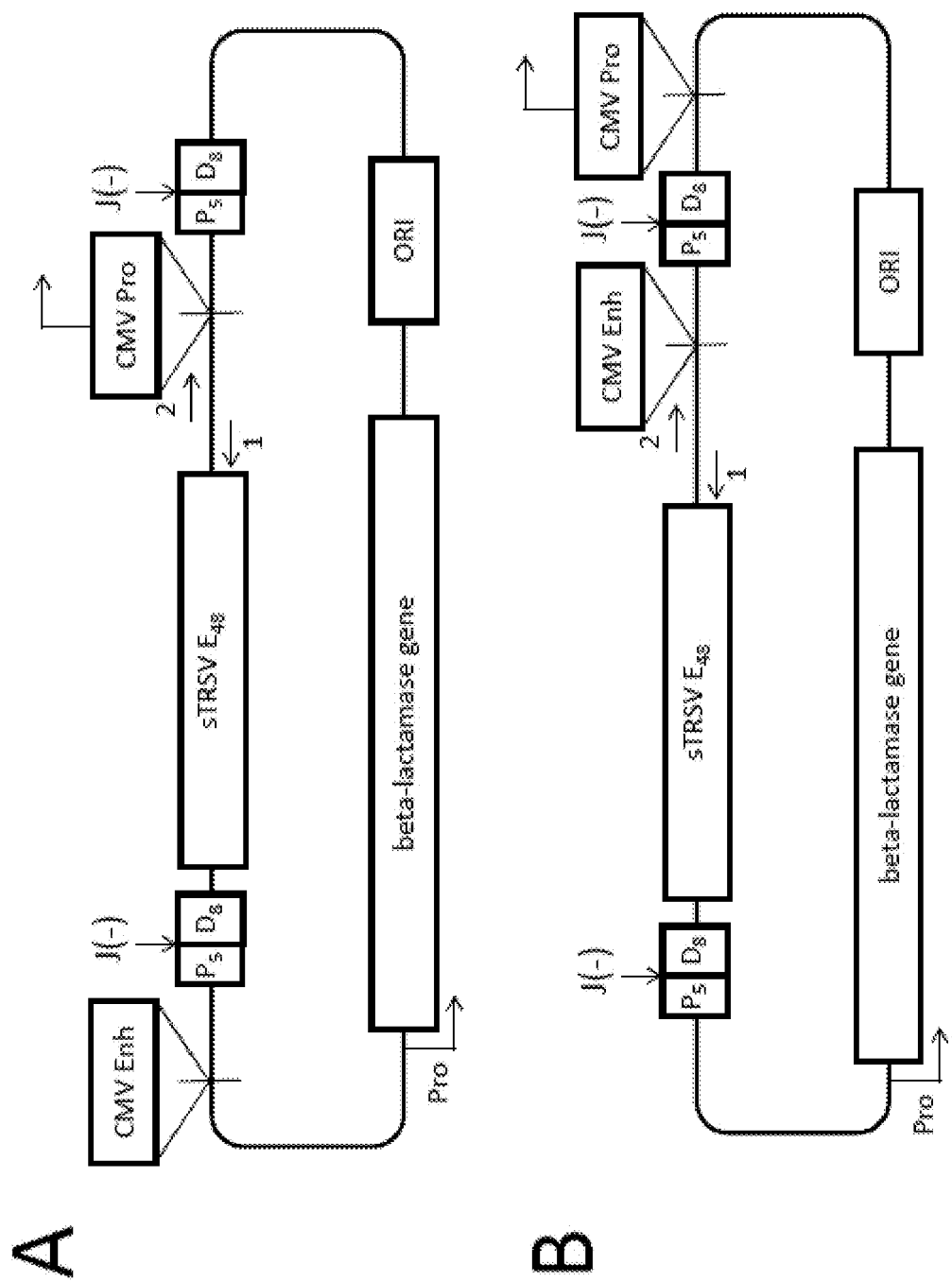

FIGS. 24A-B. (A) Construct for recovery of CMV Pro sequences after mini-monomer circularization. Enhancer function provided by upstream CMV Enh sequence. (B) Construct for recovery of CMV Enh sequences after mini-monomer circularization. Core promoter function provided by downstream CMV Pro sequence.

Figure 25:
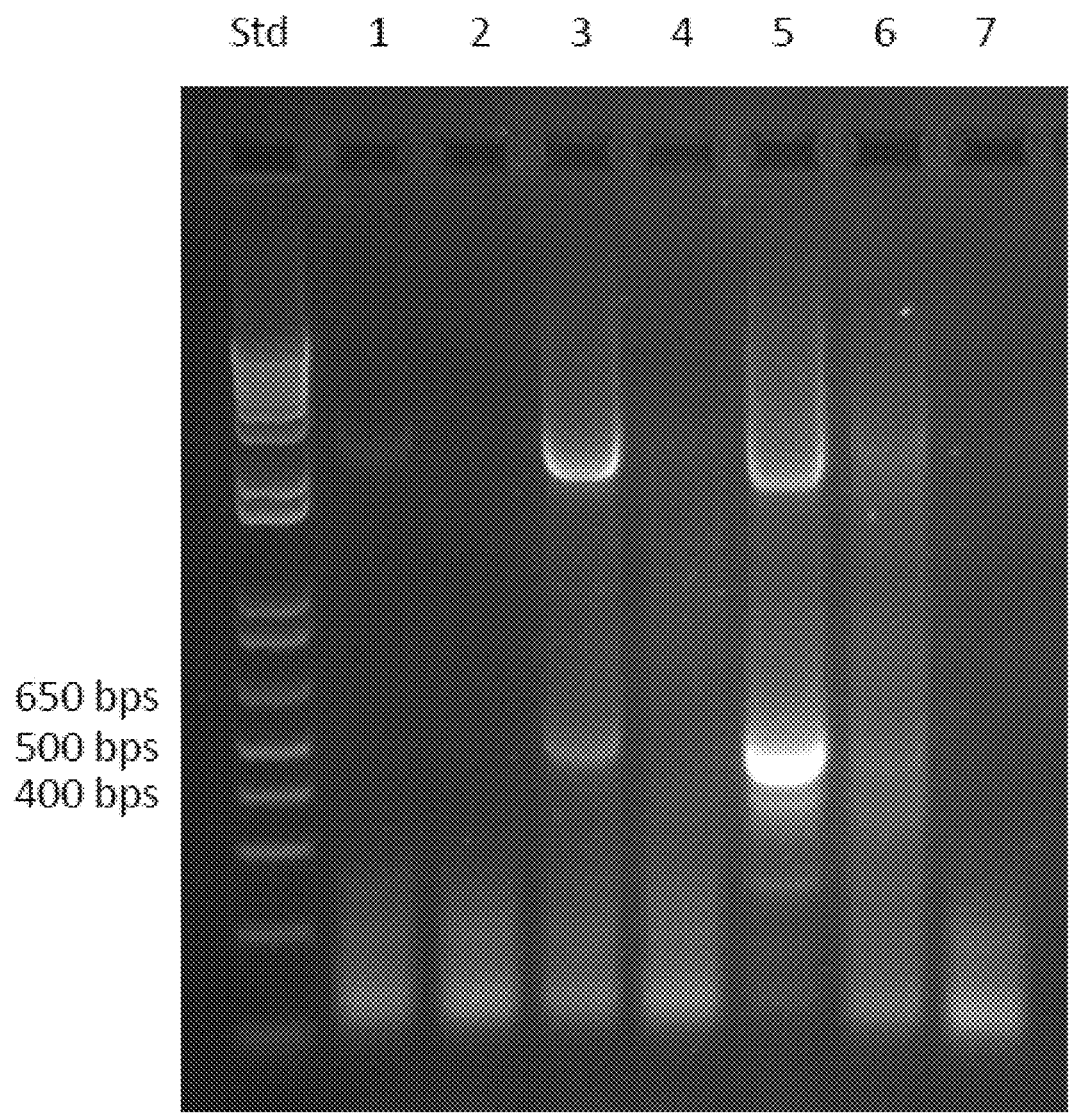

FIG. 25 illustrates RT-PCR of mini-monomer RNAs containing either the CMV core promoter or the CMV enhancer within a mini-monomer cassette transfected into Chinese Hamster Ovary (CHO) cells. Total RNA was extracted, reverse transcribed and subjected to 35 cycles of PCR with primers 1 and 2 (e.g., reverse and forward primer annealing polynucleotides, respectively). The appropriate sized fragments should be 432 and 560 base pairs long respectively. The bands are only seen in the RNA samples containing the appropriate construct Lanes: (Std) 1 Kb+DNA ladder from New England Biolabs; (1) Total CHO RNA from transfection reagent only without DNase treatment on the column; (2) Total CHO RNA from transfection reagent only with DNase treatment on the column; (3) Total CHO RNA from transfection reagent and CMV Enh mini-monomer construct without DNase treatment on the column; (4) Total CHO RNA from transfection reagent and CMV Enh mini-monomer construct with DNase treatment on the column; (5) Total CHO RNA from transfection reagent and CMV Pro mini-monomer construct without DNase treatment on the column; (6) Total CHO RNA from transfection reagent and CMV Pro mini-monomer construct with DNase treatment on the column; (7) PCR negative control (no added cDNA). Residual DNase seems to be present in treated samples as evidenced by the reduction in the expected band intensity.

DETAILED DESCRIPTION

1. Introduction

Provided are constructs designed for cloning of either prokaryotic, eukaryotic or random nucleotide DNA fragments within a self-cleaving and circularizing derivative of a ribozyme catalytic core of the (-) strand of the satellite RNA (e.g., tobacco ringspot virus (sTRSV)) in a small circular DNA plasmid that allows production of longer than unit length RNAs when the cloned fragment contains a promoter sequence. Ribozyme cleavage and circularization of said longer than unit length RNAs allows for recovery of the promoter containing sequences by reverse transcriptase-polymerase chain reaction (RT-PCR) either before or after purification of the now smaller RNA circles. The constructs facilitate the easy selection of desired polynucleotides (e.g., functional promoters, RNA stability modifiers, transcriptional modifiers) within DNA fragments with a natural selection by the amount of circular RNA produced of promoters based on their respective abilities to produce RNA.

Employing straightforward methods, desired sequences can be identified and recovered in a short time period. As desired, functional promoters, RNA stability modifying sequences and transcriptional modifying sequences can be directly recovered without the need to have or determine upstream sequences as is the case where promoters are found indirectly by cloning expressed sequence tags (ESTs). Promoters, RNA stability modifying sequences and transcriptional modifying sequences can be found in the DNA from any eukaryotic organism or can be found among random DNA sequences thus obviating the need to use promoters from heterologous organisms. Promoters, RNA stability modifying sequences and transcriptional modifying sequences can be recovered either from in vivo expression or in vitro expression systems. Randomization of identified promoters, RNA stability modifying sequences and transcriptional modifying sequences can be easily done to increase or decrease promoter/modifier strength. Using deep sequencing of recovered reverse transcriptase-polymerase chain reaction (RT-PCR) products, the relative strength of the population of promoters/modifiers recovered is naturally related to the fraction of the total each sequence represents.

2. Constructs/DNA Plasmids

The constructs described herein are generally synthetic and/or recombinant. The constructs can be comprised wholly of naturally occurring nucleic acids, or in certain embodiments can contain one or more nucleic acid analogues or derivatives. The nucleic acid analogues can include backbone analogues and/or nucleic acid base analogues and/or utilize non-naturally occurring base pairs. Illustrative artificial nucleic acids that can be used in the present constructs include, without limitation, nucleic backbone analogs peptide nucleic acids (PNA), morpholino and locked nucleic acids (LNA), bridged nucleic acids (BNA), glycol nucleic acids (GNA) and threose nucleic acids (TNA). Nucleic acid base analogues that can be used in the present constructs include, without limitation, fluorescent analogs (e.g., 2-aminopurine (2-AP), 3-Methylindole (3-MI), 6-methyl isoxanthopterin (6-MI), 6-MAP, pyrrolo-dC and derivatives thereof, furan-modified bases, 1,3-Diaza-2-oxophenothiazine (tC), 1,3-diaza-2-oxophenoxazine); non-canonical bases (e.g., : inosine, thiouridine, pseudouridine, dihydrouridine, queuosine and wyosine), 2-aminoadenine, thymine analogue 2,4-difluorotoluene (F), adenine analogue 4-methylbenzimidazole (Z), isoguanine, isocytosine; diaminopyrimidine, xanthine, isoquinoline, pyrrolo[2,3-b]pyridine; 2-amino-6-(2-thienyl)purine, pyrrole-2-carbaldehyde, and universal bases (e.g., 2' deoxyinosine (hypoxanthine deoxynucleotide) derivatives, nitroazole analogues). Non-naturally occurring base pairs that can be used in the present constructs include, without limitation, isoguanine and isocytosine; diaminopyrimidine and xanthine; 2-aminoadenine and thymine; isoquinoline and pyrrolo[2,3-b]pyridine; 2-amino-6-(2-thienyl)purine and pyrrole-2-carbaldehyde; two 2,6-bis(ethylthiomethyl)pyridine (SPy) with a silver ion; pyridine-2,6-dicarboxamide (Dipam) and a mondentate pyridine (Py) with a copper ion.

a. For Identification of Functional Promoter Sequences

Generally, constructs useful for the screening and identification of functional promoter sequences comprise a mini-monomer cassette in a minimal DNA plasmid backbone having an origin of replication and, optionally, an expression cassette for a selection gene. A specific illustration and polynucleotide sequence of a DNA plasmid useful for the screening and identification of functional promoter sequences is provided in FIGS. 1 and 2A-E.

Components of the mini-monomer cassette within the ribozyme cleavage sites—e.g., the multiple cloning site (MCS) with or without insert, the reverse and forward primer annealing sites, the ribozyme catalytic core—can be arranged in any number of several possible ways, with the following considerations:

1. The mini-monomer cassette is flanked by two ribozyme cleavage sites;
2. Primer 1 (reverse primer) is positioned upstream or 5' to primer 2 (forward primer); and
3. The RT-PCR product made by reverse transcription with primer 1 followed by PCR with primers 1 and 2 of the circular RNA made after transcription, cleavage and ligation includes the MCS with insert.

Figure 1:
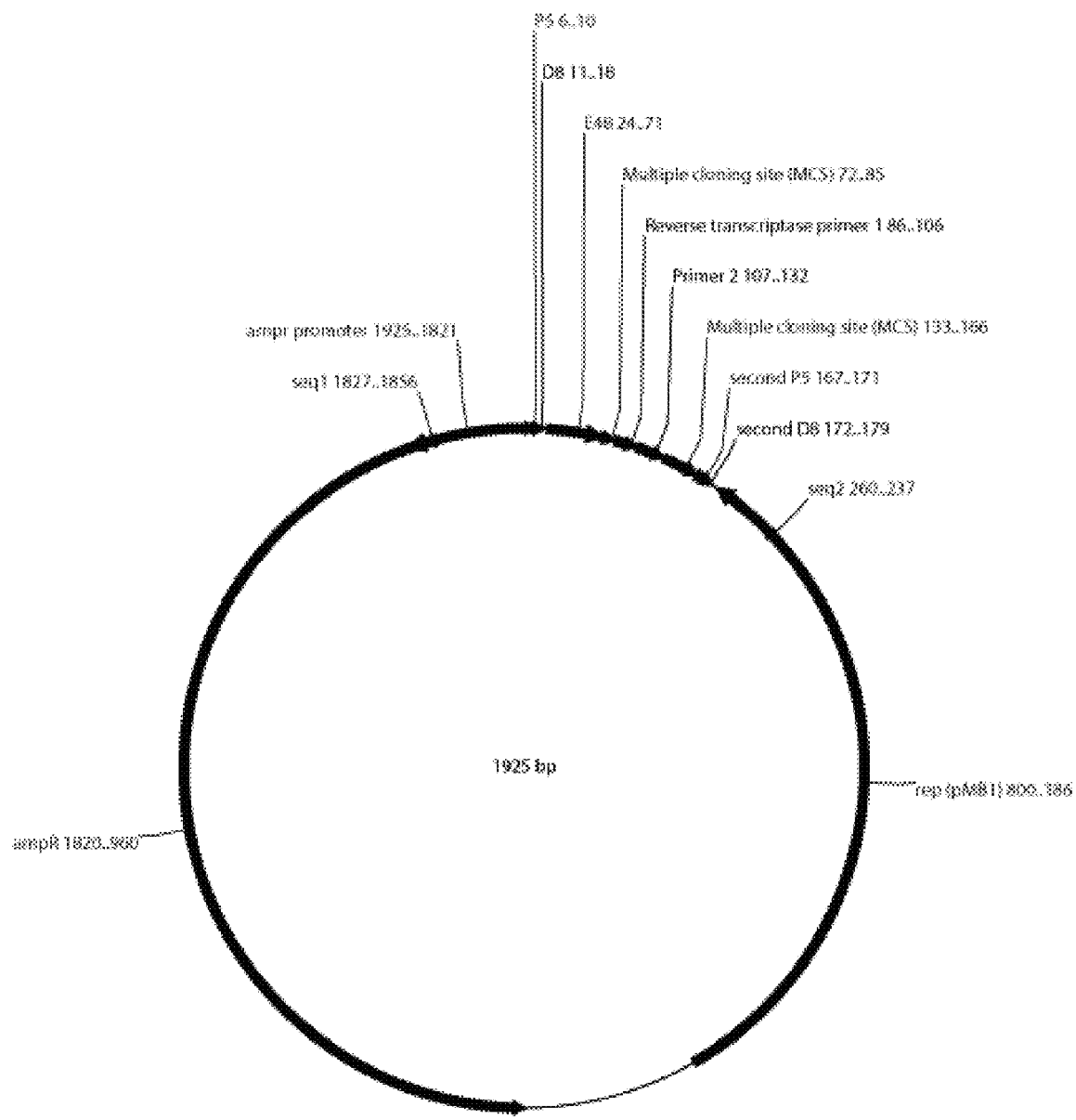
FIG. 1 illustrates a schematic of a vector map for a plasmid useful for screening for promoters.
Figure 3:
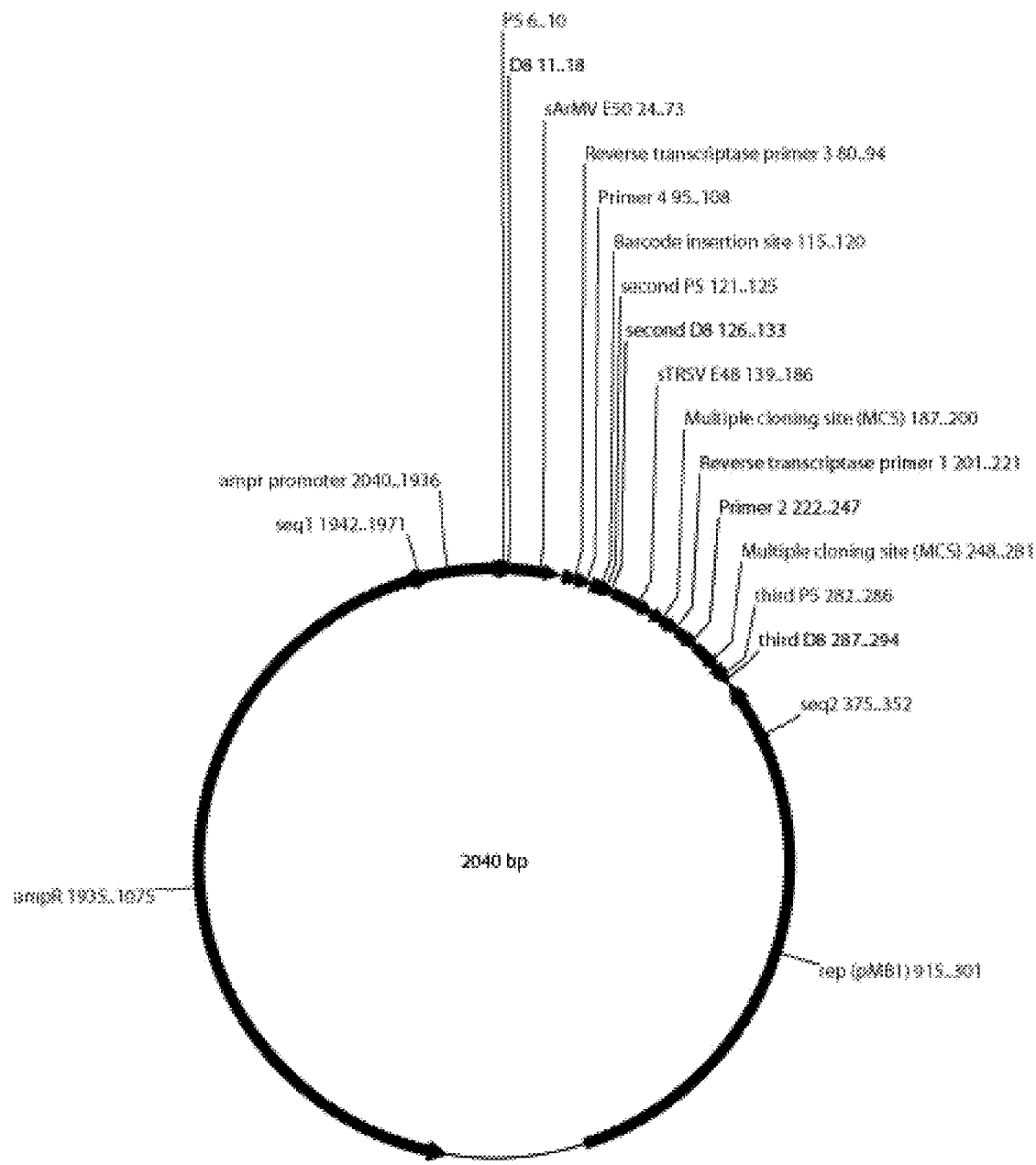
FIG. 3 illustrates a schematic of a vector map for a plasmid useful for screening for RNA stability modifiers and/or transcription modifiers.
Figure 5:
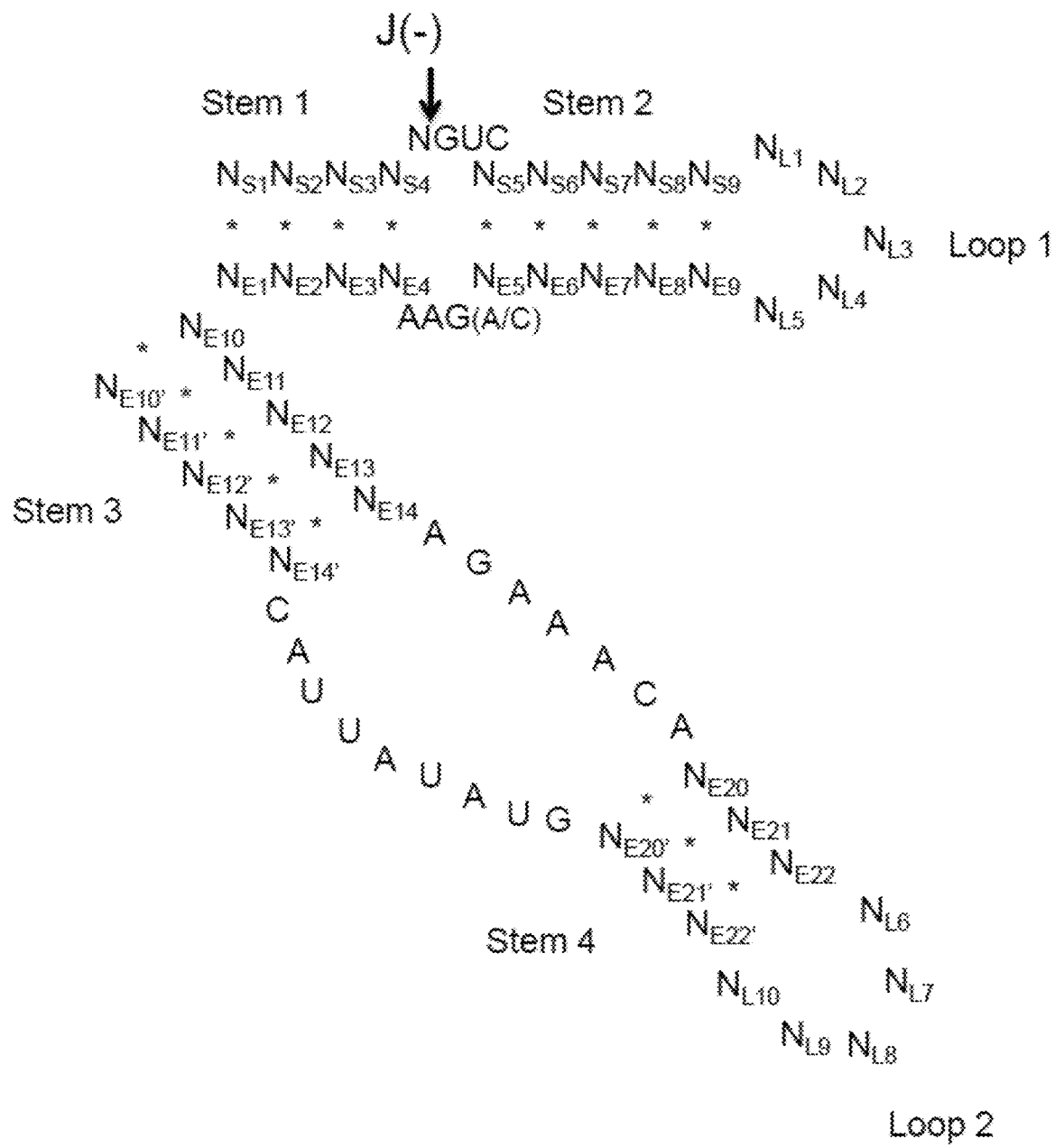
FIG. 5 illustrates a depiction of a generalized structure of the P-D regions and ribozyme core regions and their interactions.

Further, the ribozyme catalytic core can be separated at loop 2 (see, the bottom of stem 4 in FIG. 5). Several illustrative arrangements of the primers, ribozyme core and MCS with insert are depicted in FIGS. 16-18. In the arrangements depicted in FIGS. 16A-F, the reverse and forward primer annealing sites (e.g., primer 1 and primer 2) are adjacent to or abut each other. In the arrangements depicted in FIGS. 17A-B, the reverse and forward primers 1 and 2 are flanking the ribozyme core. A PCR product made with the constructs of FIGS. 17A-B would not recover or amplify the ribozyme core sequence.

Further, the MCS with or without insert and/or the forward and/or reverse primer annealing sites can be inserted into loop 2 at the bottom of stem 4 of FIG. 5. The ribozyme can be opened and/or expanded at loop 2 and still retain activity. FIGS. 18A-F illustrates arrangements wherein the ribozyme core is split or expanded at loop 2 into a left half (L-sTRSV $E_{48}$) and a right half (R-sTRSV $E_{48}$). FIGS. 18E-F depicts the reverse and forward primer annealing sites separated by either the left half of the ribozyme core or the right half of the ribozyme core, respectively. Again, a PCR product made with primer annealing sites that straddle entirely or partially the ribozyme core will not recover or amplify either the entire or partial ribozyme core polynucleotide sequence, respectively.

In an embodiment prior to the insertion of a polynucleotide suspected of containing a functional promoter, the DNA plasmid comprises operably linked polynucleotides encoding: (a) a mini-monomer cassette, comprising a first ribozyme cleavage site and a second ribozyme cleavage site, and comprising between the first ribozyme cleavage site and the second ribozyme cleavage site: (i) a ribozyme catalytic core; (ii) a multiple cloning site polynucleotide comprising plurality of restriction endonuclease cleavage sites; and (iii) a reverse primer annealing polynucleotide (e.g., for PCR or RT-PCR) located upstream or 5' to a forward primer annealing polynucleotide (e.g., for PCR or RT-PCR); and (b) a plasmid backbone, comprising an origin of replication. Illustrative ordering or relative positioning of the ribozyme catalytic core; the multiple cloning site, the reverse primer annealing polynucleotide, and the forward primer annealing polynucleotide can be as depicted in FIGS. 6, 7, 16, 17 and/or 18. In some embodiments, the DNA plasmid comprises operably linked polynucleotides encoding: (a) a mini-monomer cassette, comprising in the 5' to 3' direction: (i) a first ribozyme cleavage site; (ii) a ribozyme catalytic core; (iii) a multiple cloning site polynucleotide comprising plurality of restriction endonuclease cleavage sites, a reverse primer annealing polynucleotide and a forward primer annealing polynucleotide (e.g., for PCR or RT-PCR); and (iv) a second ribozyme cleavage site; and (b) a plasmid backbone, comprising an origin of replication. In some embodiments, the plasmid backbone further comprises an expression cassette encoding a selection marker.

In an embodiment of the construct containing a polynucleotide suspected of containing a functional promoter, the DNA plasmid comprises operably linked polynucleotides encoding: (a) a mini-monomer cassette, comprising a first ribozyme cleavage site and a second ribozyme cleavage site, and comprising between the first ribozyme cleavage site and the second ribozyme cleavage site: (i) a ribozyme catalytic core; (ii) a reverse primer annealing polynucleotide; (iii) a forward primer annealing polynucleotide; and (iv) an inserted polynucleotide suspected of comprising a promoter; and (b) a plasmid backbone, comprising an origin of replication. Illustrative ordering or relative positioning of the ribozyme catalytic core; the multiple cloning site containing the insert, the reverse primer annealing polynucleotide, and the forward primer annealing polynucleotide can be as depicted in FIGS. 6, 7, 16, 17 and/or 18. In some embodiments, the DNA plasmid comprises operably linked polynucleotides encoding: (a) a mini-monomer cassette, comprising in the 5' to 3' direction: (i) a first ribozyme cleavage site; (ii) a ribozyme catalytic core; (iii) a reverse primer annealing polynucleotide; (iv) a forward primer annealing polynucleotide; (v) an inserted polynucleotide suspected of comprising a promoter; (vi) a second ribozyme cleavage site; (b) a plasmid backbone, comprising an origin of replication. In some embodiments, the plasmid backbone further comprises an expression cassette encoding a selection marker.

i. Ribozyme Catalytic Core

The constructs or DNA plasmids described herein can comprise any functional ribozyme catalytic core capable of being circularized by ribozyme or enzymatic function. Enzymatic circularization can also work in cases where the reverse transcription reaction bypasses the ligation site. Illustrative ribozyme catalytic cores of use include, e.g., the hammerhead ribozyme, the hepatitis delta positive strand ribozyme, the hepatitis delta negative strand ribozyme, the Neurospora Varkud Satellite ribozyme, or group I or group II self-processing intron-derived ribozymes.

In varying embodiments, the ribozyme catalytic core is a hairpin ribozyme catalytic core. The hairpin ribozyme catalytic core polynucleotides of use are capable of self-cleaving itself and flanking sequences within ribozyme cleavage sites out of the context of a longer polynucleotide sequence and then ligating the excised polynucleotide into a circularized polynucleotide. In varying embodiments, the hairpin ribozyme catalytic core can be derived from a naturally occurring source. For example, Rubino, et al, *J Gen Virol* (1990) 71:1897-1903 describes examples of naturally-derived and consensus sequences of ribozyme catalytic core polynucleotides. In varying embodiments, the ribozyme catalytic core is or is derived from the negative strand self-cleavage domain (e.g., a hairpin ribozyme catalytic core) of a plant virus satellite RNA, e.g., the satellite RNA of tobacco ringspot virus (sTRSV), the satellite RNA of arabis mosaic virus (sArMV), and the satellite RNA of chicory yellow mottle virus (sCYMV). In varying embodiments, the ribozyme catalytic core is or is derived from the negative strand self-cleavage domain of a satellite RNA of the plant virus tobacco ringspot virus (sTRSV). In some embodiments, the ribozyme catalytic core polynucleotide is a synthetic sequence, e.g., based on naturally occurring or consensus ribozyme catalytic core sequences. The general structure for a hairpin ribozyme catalytic core is provided in FIG. 5. The structure of hairpin ribozyme catalytic cores are well known in the art, and described, e.g., in Müller, et al., *IUBMB Life*. (2012) 64(1):36-47; Fedor, *J Mol Biol*. (2000) 297(2):269-91; and Ferré-D'Amaré, *Biopolymers*. (2004) 73(1):71-8.

A generalized or consensus negative strand self-cleavage domain (e.g., a hairpin ribozyme catalytic core) is provided in SEQ ID NO: 8. The polynucleotide sequences of illustrative ribozyme catalytic core molecules are provided herein as SEQ ID NOs: 3, 4 and 5. In varying embodiments, the ribozyme catalytic core comprises a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to any one of SEQ ID NOs: 3, 4 or 5.

In varying embodiments, the ribozyme catalytic core can be or can be derived from a circularizing ribozyme. Examples include the Neurospora Varkud Satellite ribozyme ("VS ribozyme") and circularizing group I intron ribozyme (e.g., circularizing introns from Tetrahymena. The structure and sequence of the VS ribozyme is known in the art, and described, e.g., in Bonneau, et al., *Biochemistry* (2014) 53(39):6264-75; Bouchard, et al., *RNA*. (2014) 20(9):1451-64; and Desjardins, et al, *Nucleic Acids Res*. (2011) 39(10): 4427-37. The structure and sequence of circularizing group I intron ribozymes, including circularizing introns from Tetrahymena, are known in the art and described, e.g., in Puttaraju and Been, *Nucl. Acid Res*. (1992), 20:5357-64; Puttaraju and Been, *J Biol Chem* (1996), 271:26081-7, Ford and Ares, *Proc Natl Acad Sci USA* (1994), 91:3117-21. Ribozyme structures and mechanisms are also reviewed in Doherty, et al., *Annu Rev Biochem*. (2000) 69:597-615.

In varying embodiments, ribozyme catalytic cores other than those that naturally have substantial ligation activity could be used to identify promoter and/or transcriptional modifying sequences. In such embodiments constructs can have two functional ribozymes to produce the equivalent of a hairpin ribozyme-derived "mini-monomer" and use enzymatic ligation for formation of circles (e.g., via rolling circle replication) that can then be recovered by RT-PCR. This is shown in FIG. 15.

Figure 15:
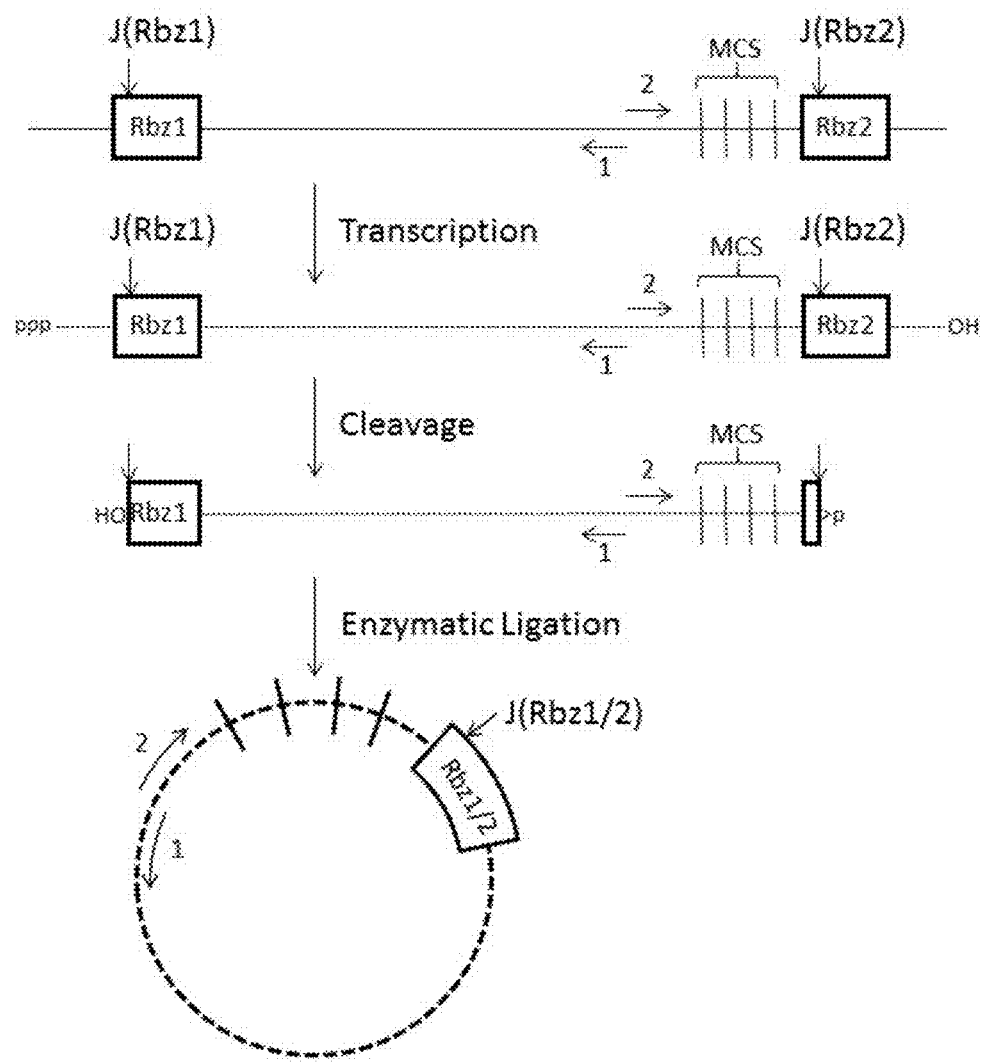
FIG. 15 illustrates an alternative scheme using generic cleaving ribozymes and enzymatic ligation to form circles containing promoter or other transcription/RNA stability modifying sequences. Note that this is just one possible form for circular RNA. The ribozyme catalytic core need not be present within the circular RNA.
Figure 19:
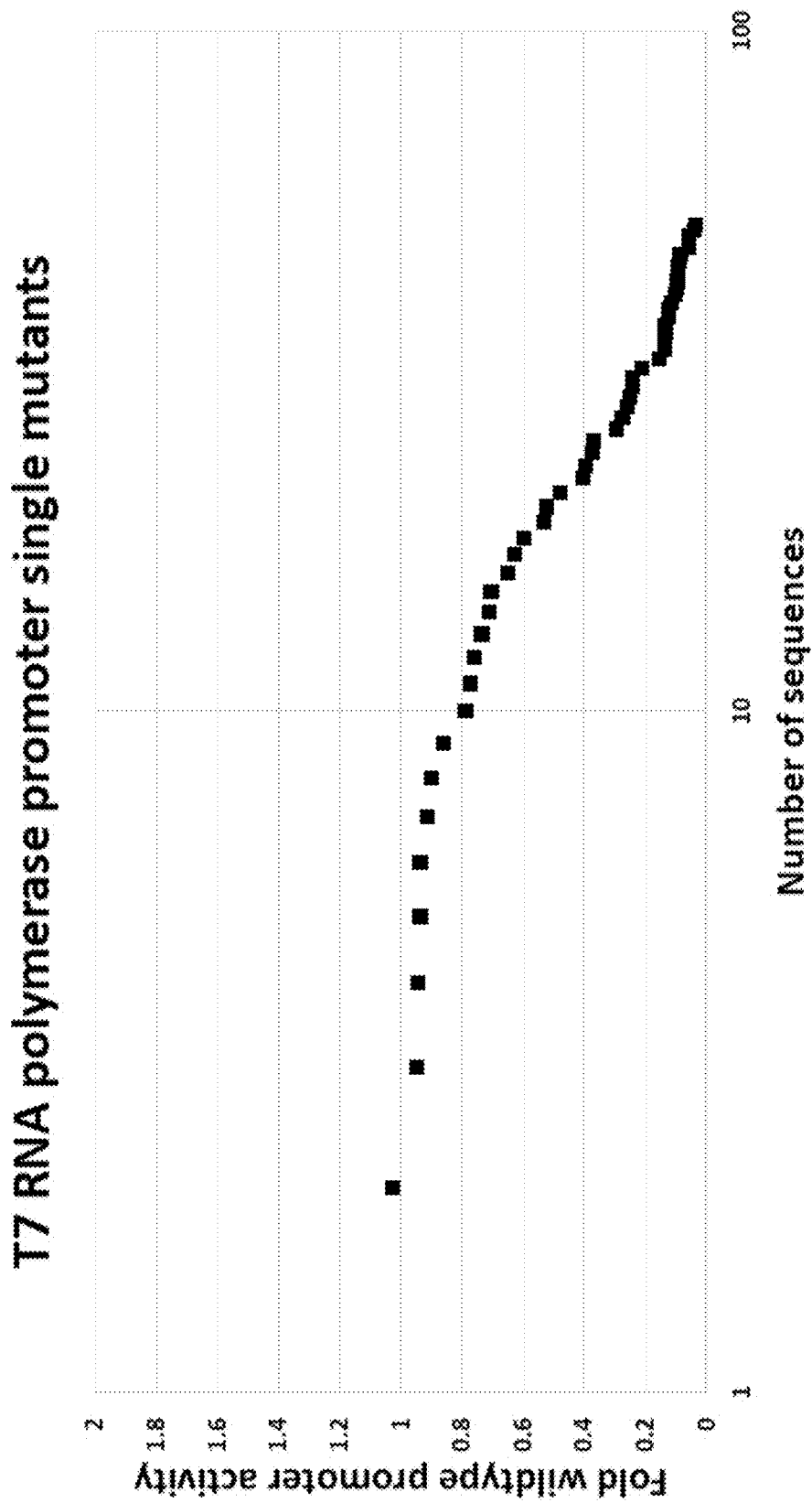
FIG. 19 illustrates the relative in vivo activity of 51 single mutants of the mutated T7 RNA polymerase promoter whose construction is described in Example 4. Mutant promoter activity is shown on the y-axis and is normalized to the wildtype promoter activity as described in Example 4. The single mutants were placed in activity order from highest to lowest relative to wildtype. The number of individual single mutants analyzed is shown on the x-axis. Due to the number of sequences shown, the y-axis is a log axis to compress its length. Of the unique single mutants possible, an analysis of 51 out of the possible 51 is shown (100%).
Figure 20:
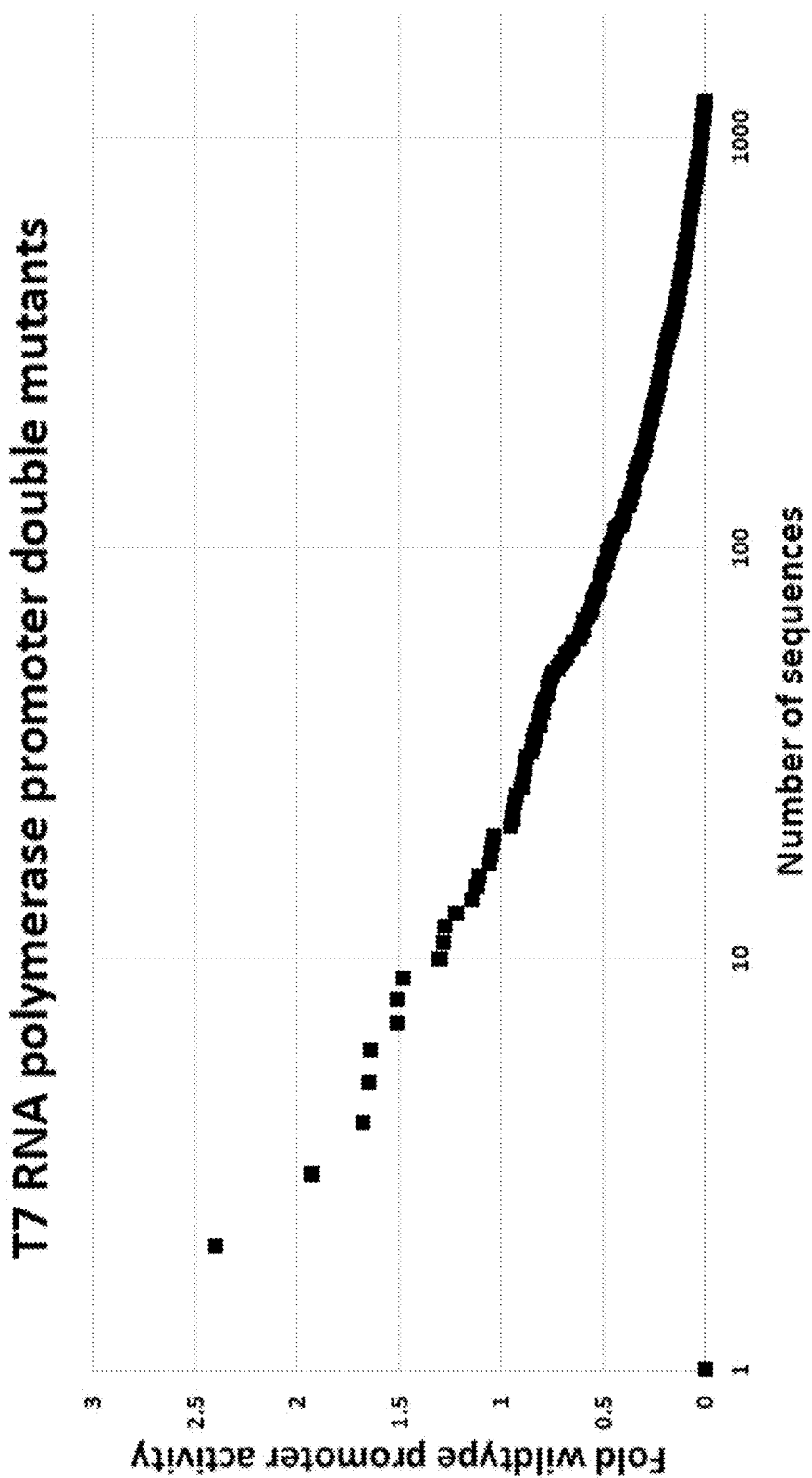
FIG. 20 illustrates the relative in vivo activity of 1223 double mutants of the mutated T7 RNA polymerase promoter whose construction is described in Example 4. Mutant promoter activity is shown on the y-axis and is normalized to the wildtype promoter activity as described in Example 4. The double mutants were placed in activity order from highest to lowest relative to wildtype. The number of individual double mutants analyzed is shown on the x-axis.

In the circular RNA-producing system shown in FIG. 15, the first or upstream ribozyme catalytic core (Rbz 1) can be from any kind of ribozyme, including, e.g., a hairpin ribozyme, a hammerhead ribozyme (e.g., a type III, or a type I hammerhead ribozyme); a hepatitis delta virus (HDV) positive strand ribozyme; or a HDV negative strand ribozyme. In various embodiments, the construct is designed with the first or upstream ribozyme catalytic core positioned or located 5' relative to the first or upstream ribozyme cleavage site (depicted as J(Rbz1)). In the circular RNA-producing system depicted in FIG. 15, the second or downstream ribozyme catalytic core (Rbz 2) also can be from any kind of ribozyme including, e.g., a hairpin ribozyme, a hammerhead ribozyme (e.g., a type III, or a type I hammerhead ribozyme); a HDV positive strand ribozyme; or a HDV negative strand ribozyme. In varying embodiments, the construct is designed with the second or downstream ribozyme catalytic core positioned or located 3' relative to the second or downstream ribozyme cleavage site (depicted as J(Rbz2)). Any ribozyme that leaves a hydroxyl group at the 5'-end and/or a 2':3' cyclic phosphodiester bond at the 3'-end can be used. The requirements for these terminal structures for enzymatic ligation would make type I or type II self-splicing intron-derived ribozyme inappropriate. The secondary structure of the cleaved RNA that forms the circular RNA is circularized most efficiently if the 5' and 3' ends are juxtaposed such that they are within a short distance—e.g., less than 5 nucleotides apart at the 3' and 5' ends of stable stems—of each other in stable secondary structures.

Accordingly, in varying embodiments, the ribozyme catalytic core can be or can be derived from a hammerhead ribozyme. The minimal hammerhead sequence required for the self-cleavage reaction includes approximately 13 conserved or invariant "core" nucleotides, most of which are not involved in forming canonical Watson-Crick base-pairs. The core region is flanked by Stems I, II and III, which are in general made of canonical Watson-Crick base-pairs but are otherwise not constrained with respect to sequence. Functionally, a hammerhead ribozyme performs a chemical reaction that results in the breakage of the substrate strand of RNA, specifically at C17, the cleavage-site nucleotide. Structurally, the hammerhead ribozyme is composed of three base paired helices, separated by short linkers of conserved sequences. These helices are called I, II and III. Hammerhead ribozymes can be classified into three types based on which helix the 5' and 3' ends are found in. If the 5' and 3' ends of the sequence contribute to stem I then it is a type I hammerhead ribozyme, to stem II is a type II and to stem III then it is a type III hammerhead ribozyme. In varying embodiments, the first and 5'-most hammerhead ribozyme catalytic core can be a Type I, Type II, Type III, HH9 and HH10 hammerhead ribozyme catalytic core. The structure and function of hammerhead ribozymes is well-characterized in the art, and has been reviewed in, e.g., Scott, et al., Prog Mol Biol Transl Sci. (2013) 120:1-23; Lee, et al., Prog Mol Biol Transl Sci. (2013) 120:25-91; and Hammann, et al., RNA. (2012) 18(5):871-85.

In varying embodiments, the second ribozyme catalytic core can be or can be derived from a positive or negative strand hepatitis delta virus (HDV) ribozyme catalytic core or a ribozyme catalytic core from a member of the HDV family. The structure of hepatitis delta virus (HDV) and HDV family members are known in the art. See, e.g., Riccitelli, et al., Prog Mol Biol Transl Sci. (2013) 120:123-71; Kapral, et al., Nucleic Acids Res. (2014) 42(20): 12833-46.

ii. Ribozyme Cleavage Sites

The ribozyme cleavage sites can be any polynucleotide sequence capable of being cleaved by a ribozyme. A generalized or consensus ribozyme is provided in SEQ ID NO: 7. As depicted in FIG. 5, the sequence and structure of the ribozyme cleavage sites are guided by the polynucleotide sequence of the ribozyme catalytic core. Interactions between the ribozyme cleavage site (as generalized in SEQ ID NO: 7) and the negative strand self-cleavage domain (as generalized in SEQ ID NO: 8) are via hydrogen bonds forming two stems—1 and 2 (as depicted in FIG. 5).

Stem 1 is formed by hydrogen bonds between NS1 and NE1, NS2 and NE2, NS3 and NE3, NS4 and NE4

Stem 2 is formed by hydrogen bonds between NS5 and NE5, NS6 and NE6, NS7 and NE7, NS8 and NE8, NS9 and NE9

Interactions within the generalized negative strand self-cleavage and ligation domain form 2 stems—3 and 4

Stem 3 is formed by hydrogen bonds between NE10 and NE10', NE11 and NE11', NE12 and NE12', NE13 and NE13', NE14 and NE14'

Stem 4 is formed by hydrogen bonds between NE20 and NE20', NE21 and NE21', and NE22 and NE22'

Stem 1 is essentially universally 4 base pairs long

Stem 2 can be as short as 4 base pairs, but can be longer

Stem 3 is essentially universally 5 base pairs long

Stem 4 is from 2 to 4 base pairs long depending on the source

Loop 1 can be as small as 4 nucleotides, if it is a special sequence called a tetra-loop, but can be longer, e.g., 100's of nucleotides up to 1000 nucleotides Loop 2 varies from 4 to 6 bases long in natural sequences The polynucleotide sequences of an illustrative ribozyme cleavage site is provided herein as SEQ ID NO: 6. In varying embodiments, the ribozyme cleavage site a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO: 6.

Generally, the polynucleotide sequences of the first and second ribozyme cleavage sites are the same.

iii. Multiple Cloning Site (MCS)

Test polynucleotides (e.g., polynucleotides suspected of encoding a functional promoter, a RNA stability modifying sequence or a transcriptional modifying sequence) are cloned into a multiple cloning site (MCS), which comprises two or more sites or sequences subject to restriction endonuclease cleavage. The positioning of the MCS and the forward and reverse primer annealing sequences (e.g., for PCR or RT-PCR) can vary in the present constructs or DNA plasmids. In varying embodiments, both the forward and reverse primer annealing sequences (e.g., for PCR or RT-PCR) are positioned 5' to the MCS. In varying embodiments, one or both of the forward and reverse primer annealing sequences (e.g., for PCR or RT-PCR) are positioned within the MCS (e.g., as depicted in FIGS. 1 and 2A-E). The MCS is located within the first and second (or upstream and downstream) ribozyme cleavage sites, but can be positioned 5' or 3' to the ribozyme catalytic core, embedded within loop 2 of the ribozyme catalytic core, and/or 5' or 3' to one or both of the reverse and forward primer annealing sites. In varying embodiments, the MCS with the insert is not positioned or located between the reverse and forward primer annealing sites. Various illustrative configurations of the components in the mini-monomer cassette are depicted in FIGS. 6, 7, 16, 17 and 18. In varying embodiments, both the forward and reverse primer annealing sequences (e.g., for PCR or RT-PCR) are positioned 3' to the MCS. In varying embodiments, both the forward and reverse primer annealing sequences (e.g., for PCR or RT-PCR) are positioned 5' to the MCS. In varying embodiments, the MCS is positioned within the mini-monomer cassette, located 3' to the ribozyme catalytic core and 5' to the second ribozyme cleavage site. In varying embodiments, the MCS is positioned within the mini-monomer cassette, located 5' to the ribozyme catalytic core and 3' to the first ribozyme cleavage site. See, e.g., FIGS. 6, 7, 16, 17 and 18.

iv. Forward and Reverse Primer Annealing Polynucleotide (e.g., for PCR or RT-PCR)

The forward and reverse primer annealing polynucleotides (e.g., for PCR or RT-PCR) are each unique sequences in the constructs or DNA plasmids and can abut each other or can be located proximally to each other (e.g., within about 500, 400, 300, 200, or 100 nucleotides from one another) with the reverse primer annealing polynucleotide (e.g., for PCR or RT-PCR) positioned 5' to the forward primer annealing polynucleotide (e.g., for PCR or RT-PCR). The forward and reverse primer annealing polynucleotides (e.g., for PCR or RT-PCR) are positioned or located such that the reverse primer annealing nucleotide (e.g., primer 1) is upstream or 5' relative to the forward primer annealing nucleotide (e.g., primer 2) and both reverse and forward primer annealing nucleotides are between the two ribozyme cleavage sites (e.g., the P-D regions) so they are excised as part of the mini-monomer cassette, and they face each other across the P-D region formed from ribozyme cleavage at the first and second P-D regions (or second and third P-D regions) followed by ribozyme ligation. The PCR product they make contains the insert region. Depending on the positioning of the reverse and forward primer annealing polynucleotides relative to the ribozyme catalytic core, the PCR product may include all of the ribozyme catalytic core, a partial polynucleotide of the ribozyme catalytic core, or exclude all of the ribozyme catalytic core. In varying embodiments, the forward and reverse primer annealing polynucleotides (e.g., for PCR or RT-PCR) are positioned such that they abut or are within the MCS. In varying embodiments, the forward and reverse primer annealing polynucleotides (e.g., for PCR or RT-PCR) are positioned within the mini-monomer cassette, located 3' to the ribozyme catalytic core and 5' to or 3' to or within the MCS, and also 5' to the second ribozyme cleavage site. In varying embodiments, the forward and reverse primer annealing polynucleotides (e.g., for PCR or RT-PCR) are positioned within the mini-monomer cassette, located 5' to the ribozyme catalytic core and 3' to or 5' to or within the MCS, and also 3' to the first ribozyme cleavage site. In varying embodiments, one or both of the forward and reverse primer annealing polynucleotides (e.g., for PCR or RT-PCR) are positioned or embedded within loop 2 of the ribozyme catalytic core. See, e.g., FIGS. 6, 7, 16, 17 and 18.

v. Inserted Polynucleotide Suspected of Comprising a Promoter

The inserted polynucleotide suspected of comprising a promoter can be from any source, for example, a randomly generated library, a naturally occurring source (e.g., a genomic library), a chemically synthesized source, a mutagenized known promoter, random polynucleotides, restriction fragments of eukaryotic DNA or prokaryotic DNA, or randomized PCR fragments of eukaryotic DNA or prokaryotic DNA. The inserted polynucleotides suspected of containing a functional promoter within the mini-monomer cassette can be functional in eukaryotes or prokaryotes. This is distinguished from the in vitro control promoter located externally and 5' to the mini-monomer cassette, which is functional in prokaryotic cells, but not eukaryotic cells.

Generally, the polynucleotide suspected of comprising a promoter has from about 50 bp to about 2000 bp, e.g., from about 100 bp to about 1000 bp. In varying embodiments, the polynucleotide suspected of comprising a promoter contains an entire promoter or a partial promoter. Within the inserted or captured polynucleotide suspected of comprising a promoter, the promoter may be centered or located more proximal to the 3' or 5' end. The methods of employing the DNA constructs described herein identify functional promoters, e.g., promoters capable of inducing, directing or promoting transcription, regardless of whether the entire promoter or a partial promoter is captured, or the location of the promoter within the captured insert. In varying embodiments, inserted polynucleotide suspected of comprising a promoter is cloned into the MCS, so therefore is positioned within the mini-monomer cassette, located 3' to the ribozyme catalytic core and 5' to the second ribozyme cleavage site. See, e.g., FIGS. 6 and 7.

vi. Plasmid Backbone for Promoter-Screening Plasmid

In the constructs or DNA plasmids that are designed for screening and identifying functional promoter sequences, the plasmid backbone has minimal features to minimize or reduce the entire size of the plasmid. In varying embodiments, the entire size of the DNA plasmids that are designed for screening and identifying functional promoter sequences is from about 1800 bp to about 3800 bp, e.g., from about 1900 bp to about 2900 bp. Generally, the plasmid backbone comprises an origin of replication and, optionally, an expression cassette for expressing a selection gene. In varying embodiments, the expression cassette for expressing a selection gene is in the antisense orientation from the mini-monomer cassette. In varying embodiments, the expression cassette for expressing a selection gene is in the sense orientation to the mini-monomer cassette. The expression cassette for expressing a selection gene can be either in the antisense or sense orientation. If the selection is being done in eukaryotic cells, the selection gene can be any marker known in the art for selection of a host cell that has been transformed with a desired plasmid. In varying embodiments, the selection marker comprises a polynucleotide encoding a gene or protein conferring antibiotic resistance, heat tolerance, fluorescence, luminescence or rescue of auxotrophic growth for specific amino acids or nucleotides. Such selection markers are well known in the art.

vii. Optional Control Promoter

The constructs or DNA plasmids designed for the screening of promoter sequences can optionally further contain a control promoter. In varying embodiments, the control promoter is a promoter functional in a prokaryotic host cell. Such a promoter is useful as an internal control for in vitro transcription. In some embodiments, the control promoter can be added to the library by PCR. Illustrative promoters functional in a prokaryotic cell of use include without limitation bacteriophage promoters T7, T3 and SP6.

Accordingly, in varying embodiments of the constructs or DNA plasmids designed for screening of promoters a promoter functional in a prokaryotic host cell is positioned 5' of the first ribozyme cleavage site. See, e.g., FIG. 8, lower embodiment.

Transcription of the plasmid library in vitro with a RNA polymerase (e.g., a T7, T3 or SP6 RNA polymerase) followed by RT-PCR with forward and reverse RT-PCR primers and sequencing (e.g., deep sequencing) produces a processing and library bias-controlled sequenced data set for comparison with sequenced data sets derived from internal promoters (e.g., the functional promoter within the test insert polynucleotide).

b. For Identification of RNA Stability/Transcription Modifying Sequences

Generally, constructs useful for the screening and identification of RNA stability/transcription modifying sequences comprise a mini-monomer cassette in a DNA plasmid backbone having an origin of replication, and optionally, an expression cassette for a selection gene. Generally, the plasmid backbones of the constructs useful for RNA Stability/Transcription modifier screening do not have an upper size limit.

Any under or overrepresented sequence may be due to an effect at a distance on the promoter by the insert, which can be functioning as an enhancer or repressor of transcription. Enhancer and repressors can function up to 10 Kb away from a promoter either upstream or downstream. One construct design that takes the effect a potential transcription enhancer or repressor has on a promoter is illustrated in FIGS. 3, 4A-F and 11. A specific illustration and polynucleotide sequence of a DNA plasmid useful for the screening and identification of functional promoter sequences utilizes first and second mini-monomer cassettes. The first mini-monomer cassette comprises a randomized barcode polynucleotide and the second mini-monomer cassette comprises an inserted polynucleotide suspected of comprising a RNA stability/transcription modifying sequence.

In one embodiment, the construct or DNA plasmid containing a polynucleotide suspected of containing a RNA stability/transcription modifying sequence comprises:
(a) a promoter functional in a eukaryotic cell or in a prokaryotic cell;
(b) a mini-monomer cassette, comprising:
 (i) a first ribozyme cleavage site;
 (ii) a ribozyme catalytic core;
 (iii) a reverse primer annealing polynucleotide (e.g., for PCR or RT-PCR);
 (iv) a forward primer annealing polynucleotide (e.g., for PCR or RT-PCR);
 (v) an inserted polynucleotide suspected of comprising a RNA stability modifier or a transcription modifier;
 (vi) a second ribozyme cleavage site;
(c) a plasmid backbone, comprising an origin of replication. In some embodiments, the plasmid backbone further comprises an expression cassette encoding a selection marker.

In one embodiment, the construct or DNA plasmid containing a polynucleotide suspected of containing a RNA stability/transcription modifying sequence comprises:
(a) a test promoter, wherein the test promoter is functional in a eukaryotic cell or in a prokaryotic cell;

(b) a first mini-monomer cassette, comprising:
(i) a first ribozyme cleavage site;
(ii) a first ribozyme catalytic core;
(iii) a first reverse primer annealing polynucleotide (e.g., for PCR or RT-PCR);
(iv) a first forward primer annealing polynucleotide (e.g., for PCR or RT-PCR);
(v) a barcode polynucleotide
(vi) a second ribozyme cleavage site;
(c) a second mini-monomer cassette, comprising:
(i) the second ribozyme cleavage site;
(ii) a second ribozyme catalytic core;
(iii) a second reverse primer annealing polynucleotide (e.g., for PCR or RT-PCR);
(iv) a second forward primer annealing polynucleotide (e.g., for PCR or RT-PCR);
(v) an inserted polynucleotide suspected of comprising a RNA stability modifier or a transcription modifier;
(vi) a third ribozyme cleavage site;
(d) a plasmid backbone, comprising an origin of replication. In some embodiments, the plasmid backbone further comprises an expression cassette encoding a selection marker.

In the constructs or DNA plasmids designed to screen for RNA stability/transcription modifying sequences, the ribozyme catalytic cores, ribozyme cleavage sites, multiple cloning sites, and forward and reverse RT-PCT primer annealing polynucleotide sequences are as described above for the DNA plasmids designed to screen for functional promoter sequences. Distinguished from the promoter screening plasmid, constructs or DNA plasmids designed to screen for RNA stability/transcription modifying sequences have a first mini-monomer cassette containing a barcode polynucleotide, and a second mini-monomer cassette containing an inserted polynucleotide suspected of comprising a RNA stability modifier or a transcription modifier. Further, the plasmid backbone can be minimal, but need not be minimal. A schematic of the constructs or DNA plasmids designed to screen for RNA stability/transcription modifying sequences is provided in FIG. 11. Like the DNA plasmid designed for screening promoters, a 5'-RNA polymerase control promoter (e.g., a promoter functional in a prokaryotic host cell) can optionally be included in the construct to serve as an internal control for in vitro transcription.

The positioning or the ordering of the components in the first and second mini-monomer cassettes, including the MCS (with or without an inserted polynucleotide), the reverse and forward primer annealing sites and the ribozyme catalytic core, can be varied as described above for the mini-monomer cassette in the constructs used to identify promoter sequences. Illustrative variations in the arrangement or positioning of the components between the ribozyme cleavage sites in the first and second mini-monomer cassettes are depicted in FIGS. 16-18. The positioning or the ordering of the components in the first and second mini-monomer cassettes, including the MCS, the reverse and forward primer annealing sites and the ribozyme catalytic core, can be the same or different.

i. First Mini-Monomer Cassette Containing Barcode Polynucleotide

The first mini-monomer cassette is located 5' to the second mini-monomer cassette. The first mini-monomer cassette contains a barcode polynucleotide positioned 3' to a first ribozyme catalytic core and first forward and first reverse primer annealing polynucleotides and 5' to a second ribozyme cleavage site. The barcode polynucleotide comprises a random DNA sequence comprising from about 10 to about 20 N residues, e.g., 10, 11, 12, 13, 14, 15, 16, 17, 18, 19, or 20 N residues. The barcode polynucleotide serves as a unique identifier of a particular DNA plasmid comprising an inserted polynucleotide suspected of comprising a RNA stability modifier or a transcription modifier in the second mini-monomer cassette, and allows tracking of each inserted polynucleotide suspected of comprising a RNA stability modifier or a transcription modifier. The first ribozyme catalytic core in the first mini-monomer cassette is as described above, and can be the same or different as the second ribozyme catalytic core in the second mini-monomer cassette. See, e.g., FIG. 11.

To reduce the possibility of recombination between two identical ribozyme core sequences, however, two different ribozyme cores can be used. For example, in one embodiment, the first mini-monomer cassette comprises a ribozyme catalytic core from the satellite RNA of arabis mosaic virus (sArMV) and the second mini-monomer cassette comprises a ribozyme catalytic core from the satellite RNA of tobacco ringspot virus (sTRSV). Utilizing ribozyme catalytic cores having slightly different polynucleotide sequences should not only decrease recombination between the two, but will also serve as an internal control for the sequencing (e.g., deep sequencing).

ii. Second Mini-Monomer Cassette Containing Inserted Polynucleotide Suspected of Comprising a RNA Stability Modifier or a Transcription Modifier The second mini-monomer cassette is located 3' to the first mini-monomer cassette. In varying embodiments, inserted polynucleotide suspected of comprising a RNA stability modifier or a transcription modifier is cloned into the MCS of the second mini-monomer cassette, so therefore is positioned within the second mini-monomer cassette, located 3' to the second ribozyme catalytic core and 5' to the third ribozyme cleavage site. See, e.g., FIG. 11.

The inserted polynucleotide suspected of comprising a RNA stability modifier or a transcription modifier can be from any source, for example, a randomly generated library, a naturally occurring source (e.g., a genomic library), a chemically synthesized source, random nucleotides, restriction fragments of eukaryotic DNA, or randomized PCR fragments of eukaryotic DNA. Generally, the polynucleotide suspected of comprising a RNA stability modifier or a transcription modifier has from about 50 bp to about 1000 bp. In varying embodiments, the polynucleotide suspected of comprising a RNA stability modifier or a transcription modifier contains an entire modifying sequence or a partial modifying sequence. Within the inserted or captured polynucleotide suspected of comprising a modifying sequence, the modifier may be centered or located more proximal to the 3' or 5' end. The methods of employing the DNA constructs described herein identify functional modifiers, e.g., polynucleotides capable of modifying (e.g., increasing or decreasing) RNA stability and/or transcription, regardless of whether the entire modifying sequence or a partial modifying sequence is captured, or the location of the modifying sequence within the captured insert. In varying embodiments, inserted polynucleotide suspected of comprising a RNA stability modifier or a transcription modifier is cloned into the MCS, so therefore is positioned within the mini-monomer cassette, located 3' to the ribozyme catalytic core and 5' to the second ribozyme cleavage site. See, e.g., FIG. 11.

Generally, the first, second and third ribozyme cleavage sites are the same.

iii. Plasmid Backbone of Construct for RNA Stability/Transcription Modifier Screening The plasmid backbone for the constructs or DNA plasmids designed to screen for RNA stability/transcription modifying sequences can but need not be minimized. Like the plasmid backbone for the constructs or DNA plasmids designed to screen for promoters, the plasmid backbone for the constructs or DNA plasmids designed to screen for RNA stability/transcription modifying sequences have an origin of replication, and optionally, an expression cassette for expressing a selection marker, as described above. The entire size of the DNA plasmids that are designed for screening for RNA stability/transcription modifying sequences is guided by the location of the promoter functional in a eukaryotic cell in relationship to the first and third ribozyme cleavage sites. In the case where the eukaryotic promoter is 3' of the third ribozyme cleavage site, the overall plasmid size is minimized. In embodiments where the eukaryotic promoter is 5' of the first ribozyme cleavage site, there is no size limitation on the plasmid. In the case where the eukaryotic promoter is 5' of the first ribozyme cleavage site, the plasmid can also contain other features (e.g., sequences for entry into cells, e.g., left and right border sequences for Agrobacterium-mediated transfer). Viral replicating vectors can also be used. Accordingly, in varying embodiments, the promoter functional in a eukaryotic cell is located 3' of the third ribozyme cleavage site. In such embodiments, the plasmid has from about 1800 bp to about 3800 bp, e.g., from about 1900 bp to about 2900 bp. In varying embodiments, the promoter functional in a eukaryotic cell is located 5' of the first ribozyme cleavage site. In such embodiments, there is no fixed upper size limit, but the plasmid optionally can have from about 2100 bp to about 3100 bp, e.g., from about 2100 bp to about 2250 bp.

iv. Optional Control Promoter

The constructs or DNA plasmids designed for the screening of RNA stability and/or transcription modifying sequences can optionally further contain a control promoter. In varying embodiments, the control promoter is a promoter functional in a prokaryotic host cell. In some embodiments, the control promoter can be added to the library by PCR. As discussed above for the promoter screening plasmids, such a promoter is useful as an internal control for in vitro transcription. Illustrative promoters functional in a prokaryotic cell of use include without limitation bacteriophage promoters T7, T3 and SP6.

Accordingly, in varying embodiments of the constructs or DNA plasmids designed for screening of promoters a control promoter functional in a prokaryotic host cell is positioned 5' of the first ribozyme cleavage site. See, e.g., FIG. 11.

Transcription of the plasmid library in vitro with a RNA polymerase (e.g., a T7, T3 or SP6 RNA polymerase) followed by RT-PCR with forward and reverse RT-PCR primers and sequencing (e.g., deep sequencing) produces a processing and library bias-controlled sequenced data set for comparison with sequenced data sets derived from internal promoters (e.g., the functional promoter within the test insert polynucleotide).

3. Methods a. For Identification of Functional Promoter Sequences

In varying embodiments, methods for screening for promoters entail the steps of:

a) providing a population of plasmids designed for screening promoters, the plasmids in the population containing an insert suspected of containing a functional promoter sequence, as described above and herein;

b) transcribing the population of plasmids into RNA;

c) reverse transcribing into cDNA the population of circularized RNA transcripts of self-cleaved mini-monomer cassettes; and d) sequencing the inserted polynucleotides comprising a functional promoter in the population of cDNA reverse-transcripts of self-cleaved mini-monomer cassettes.

i. Initial Transcriptional Control Step

In embodiments employing a plasmid further comprising a control promoter (e.g., a promoter functional in a prokaryotic host cell), positioned 5' to the mini-monomer cassette, in vitro transcription can additional and initially be performed from this promoter as an internal control for processing (e.g., self-cleaving) efficiency. In vitro transcription is performed using methodologies known in the art, as described below and herein.

ii. Transcribing the Population of Plasmids into RNA

The step of transcribing the population of plasmids into RNA can be performed using any methodologies known in the art. Such methodologies are described, e.g., in Green and Sambrook, Molecular Cloning, A Laboratory Manual, 4th Ed., Cold Spring Harbor Press, (2012).

Figure 7:
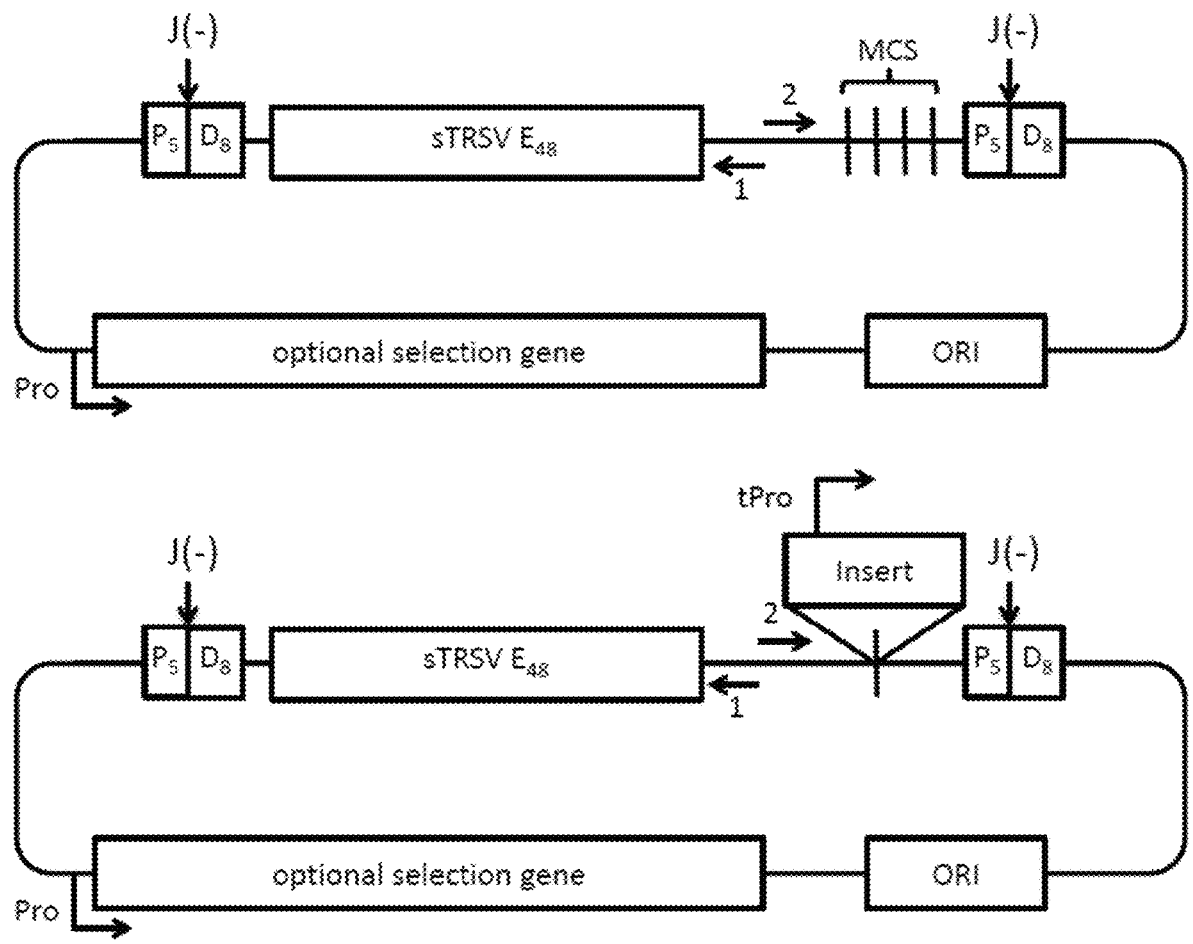
FIG. 7 illustrates cloning of the mini-monomer cassette into a plasmid backbone (e.g., pUN) followed by insertion of fragments into the mini-monomer cassette MCS. The upper construct is the plasmid backbone-ribozyme construct without potential test promoter-containing inserts (tPro). The lower construct is the same, but containing a polynucleotide suspected of encoding a test promoter-containing insert (tPro). In varying embodiments, the construct may further optionally contain an expression cassette for expression of a selection gene, in either the sense or antisense orientation in relation to the test promoter containing insert. In varying embodiments, the optional selection gene polynucleotide can be an antibiotic resistance gene (e.g., a beta-lactamase gene that confers resistance to carbenicillin or related antibiotics). The ORI refers to an origin of replication for plasmid replication.
Figure 8:
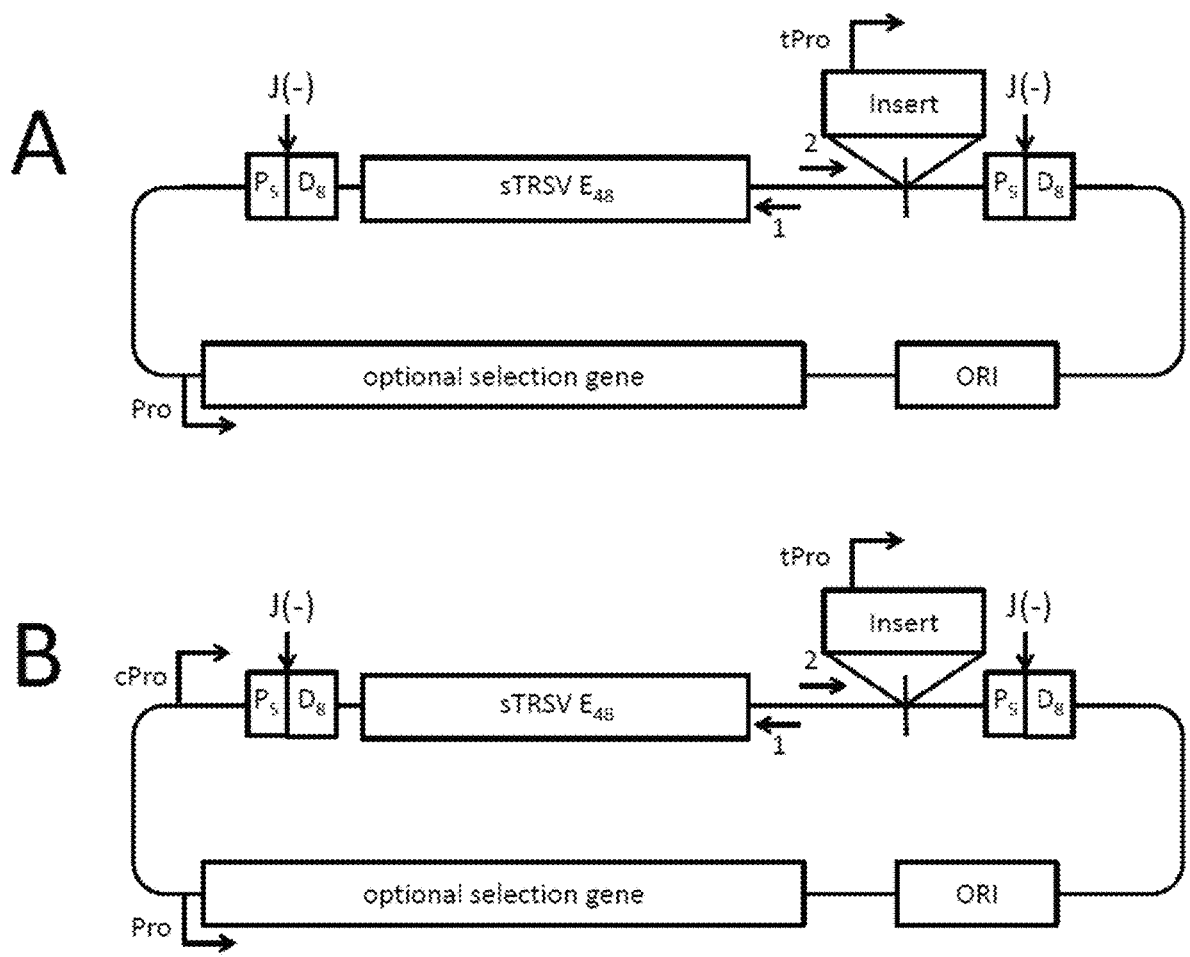
FIG. 8 illustrates a mini-monomer cassette into a plasmid backbone, with the optional addition of a control promoter (cPro), e.g., a promoter functional in a prokaryotic cell (e.g., a T7 polymerase promoter) as an internal control. Upper construct is the same as the lower construct in FIG. 7, above. Lower construct illustrates optional addition of a control promoter (cPro), e.g., a promoter functional in a prokaryotic cell (e.g., a T7 polymerase promoter). Here it is depicted 5' to the mini-monomer cassette.

As discussed above, constructs or DNA plasmids designed for screening for functional promoters have a ribozyme insert having two (-) strand ribozyme cleavage sites flanking a (-) strand ribozyme catalytic core and an inserted polynucleotide suspected of encoding a functional promoter (FIGS. 7 and 8). This ribozyme insert, inclusive of the ribozyme cleavage sites, the (-) strand ribozyme catalytic core, an inserted polynucleotide suspected of encoding a functional promoter, and forward and reverse primer annealing sequences, all between the two ribozyme cleavage sites, is referred to hereinafter as a "mini-monomer."

In varying embodiments, the step of transcribing the population of plasmids into RNA can be performed in vitro or in vivo. In vitro testing of DNA plasmids comprising a library of inserts suspected of comprising a functional promoter sequence can be achieved using nuclei preparations, nuclear extracts capable of giving in vitro transcription or purified RNA polymerases. In vivo methods entail the transformation of a suitable host cell of closed circular DNA plasmid using any method known in the art, e.g., by electroporation of protoplasts, fusion of liposomes to cell membranes, cell transfection methods using calcium ions or PEG, use of gold or tungsten microparticles coated with plasmid with the gene gun. The cells of all eukaryotic and prokaryotic organisms (plants, animals, fungi, bacteria, archaea etc.) can be used. Libraries of DNA inserts cloned into the mini-monomer cassette can be used to select promoter-containing fragments in a variety of ways. As one can only recover the PCR products after greater than full-length transcription which only occurs with the insertion of a polynucleotide encoding a functional promoter, functional promoter sequences can be readily identified from a mixed population of polynucleotide sequences with high specificity.

An insert containing a functional eukaryotic promoter is transcribed into RNA from its transcription start site. In varying embodiments, the functional promoter is functional in a eukaryotic cell or is functional in a prokaryotic cell. The primary transcript continues around the full length of the plasmid and produces the full-length mini-monomer RNA sequence containing the full insert on its second pass through that part of the plasmid backbone through to the second ribozyme cleavage site for a second time. See, e.g., FIG. 9. In the absence of a terminator, the primary transcript can be substantially longer than shown. When the inserted polynucleotide comprises a functional promoter, the first and second ribozyme cleavage site are transcribed into RNA by a RNA polymerase, and RNA transcripts comprising the mini-monomer cassette self-cleave from the transcript. A population of circularized RNA transcripts of self-cleaved mini-monomer cassettes is formed.

Figure 9:
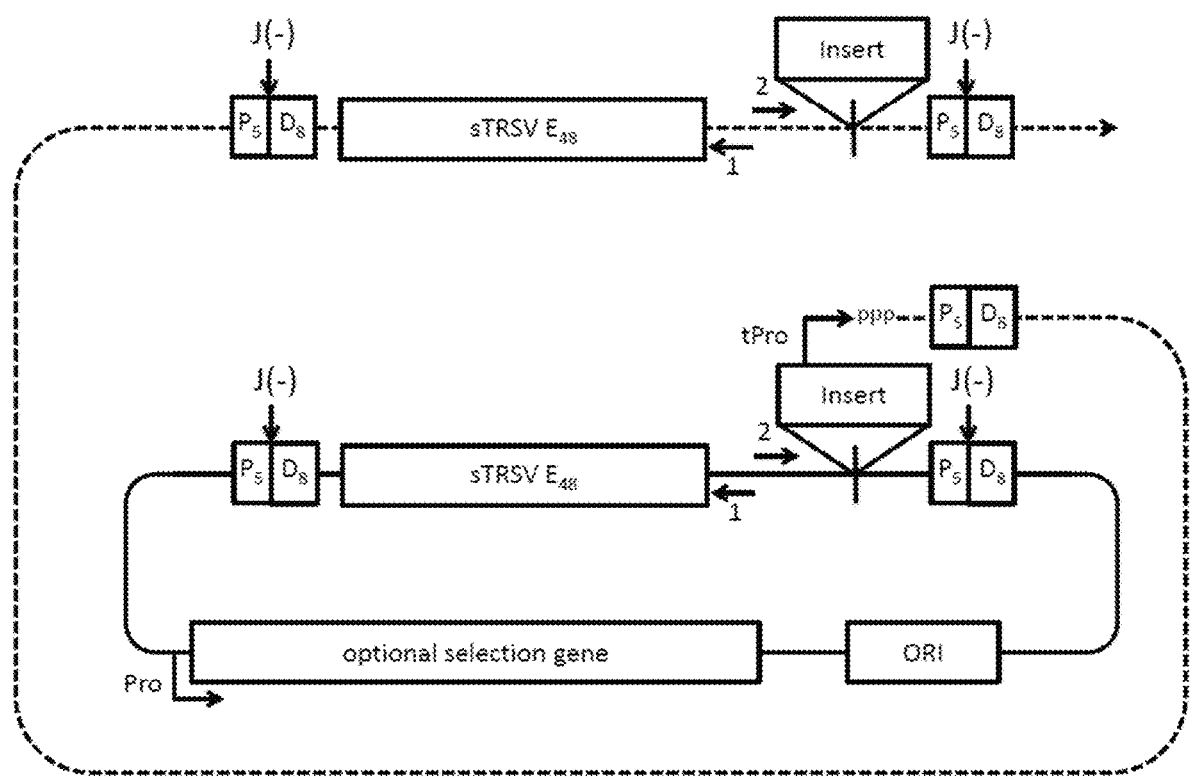
FIG. 9 illustrates a primary transcript from a plasmid comprising a mini-monomer cassette-DNA insert containing a test promoter (tPro). The dashed line represents the primary transcript. Orientation is shown by the 5' triphosphate (ppp) and the 3' hydroxyl (arrowhead at the right-hand end of the dashed line). Note that the transcript is not drawn to scale. In practice, the primary transcript is longer than depicted at the 3' end.
Figure 10:
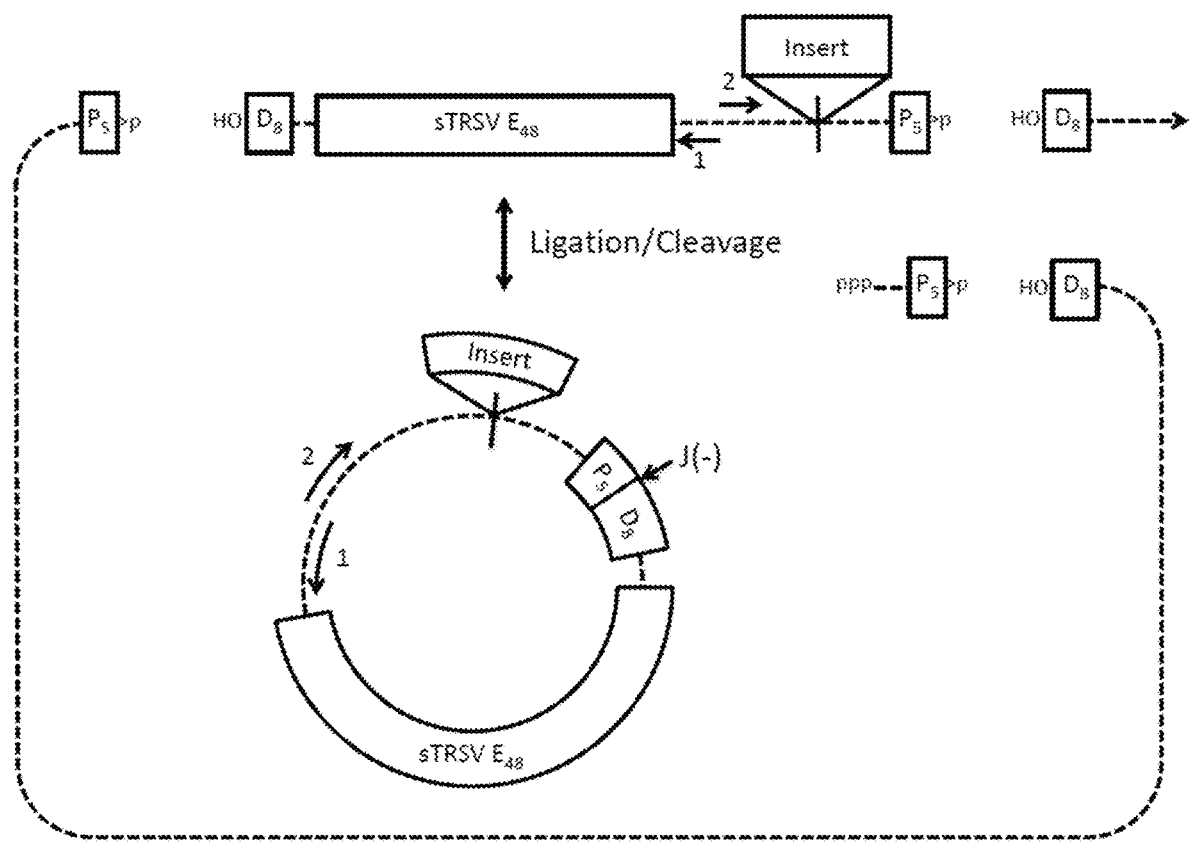
FIG. 10 illustrates complete processing products for greater than full-length RNA transcripts.

The primary transcript shown in FIG. 9 is processed (e.g., self-cleaved) to produce the excised and circularized mini-monomer cassette shown in FIG. 10. Partial processing products may also be present. Any transcript that is terminated after the ribozyme catalytic core ($E_{48}$), but before the second ribozyme cleavage site (e.g., $P_5$-$D_8$) immediately downstream of the catalytic core is processed, but is not able to form a circular mini-monomer containing the promoter-carrying insert. Any transcripts that terminate after the second ribozyme cleavage site (e.g., $P_5$-$D_8$) immediately downstream of the catalytic core is able to form a circular mini-monomer containing the promoter-carrying insert.

In varying embodiments, the methods further comprise the step of purifying or isolating the transcribed RNA from non-RNA. In varying embodiments, the methods further comprise the step of purifying or isolating the population of circularized RNA transcripts of self-cleaved mini-monomer cassettes. In varying embodiments, purifying or isolating circularized RNA transcripts of self-cleaved mini-monomer cassettes is performed by two-dimensional gel electrophoresis.

iii. Reverse-Transcribing into cDNA the Population of Circularized RNA Transcripts of Self-Cleaved Mini-Monomer Cassettes The step of reverse-transcribing the population of plasmids into cDNA can be performed using any methodologies known in the art. Such methodologies are described, e.g., in Green and Sambrook, Molecular Cloning, A Laboratory Manual, 4th Ed., Cold Spring Harbor Press, (2012). In varying embodiments, the reverse transcribing step comprises amplifying from the forward and reverse primer annealing polynucleotides (e.g., for PCR or RT-PCR).

cDNA can be synthesized from reverse transcription of the RNA of circularized and self-cleaved mini-monomer carrying a functional promoter (e.g., eukaryotic or prokaryotic) using a primer that binds at the reverse primer annealing sequence (e.g., for PCR or RT-PCR). Reverse transcription can be followed by PCR with the forward and reverse primers, thereby yielding a PCR product containing the mini-monomer sequence with the promoter-containing insert if the RNA template for reverse transcription is circular. If PCR product is amplified from residual circular plasmid DNA or on unprocessed transcripts, it will give a larger PCR product containing all of the plasmid backbone and mini-monomer cassette, which is substantially larger. Such oversized PCR product can be readily excluded, e.g., by adjusting PCR conditions or, in the case of residual DNA template, by treatment with DNase or the restriction endonuclease Dpn I. These RT PCR-derived DNAs can only be produced if a cloned DNA insert contains a functional eukaryotic promoter.

iv. Sequencing the Inserted Polynucleotides Comprising a Functional Promoter in the Population of cDNA Reverse-Transcripts of Self-Cleaved Mini-Monomer Cassettes The step of sequencing the inserted polynucleotides comprising a functional promoter in the population of cDNA reverse-transcripts of self-cleaved mini-monomer cassettes can be performed using any methodologies known in the art. Such methodologies are described, e.g., in Green and Sambrook, Molecular Cloning, A Laboratory Manual, 4th Ed., Cold Spring Harbor Press, (2012). In varying embodiments, next generation sequencing, deep sequencing or ultra deep sequencing methodologies are applied. Deep sequencing data analysis is described, e.g., in "Deep Sequencing Data Analysis (Methods in Molecular Biology)," Noam Shomron (Editor), Humana Press; 2013 edition. Next generation sequencing is described, e.g., in "Next-Generation DNA Sequencing Informatics," Stuart M. Brown (Editor), Cold Spring Harbor Laboratory Press; 1st edition (2013); "Next-generation Sequencing: Current Technologies and Applications," Jianping Xu (Editor), Caister Academic Press (2014); Wilhelm, et al., *Nature*. (2008) 453:1239-1243; Nagalakshmi, et al., *Science*. (2008) 320:1344-1349; and Mortazavi, et al., *Nat. Methods*. (2008) 5:621-628.

v. Exposure to External Influences

In varying embodiments, de novo selection and subsequent evolution of externally influenced promoters is performed. Using a library containing inserted polynucleotides suspected of comprising a functional promoter, as described above, insertion of this library into cells with or without some external factor (e.g., $Ca^{++}$ ions, salt, temperature stress, hormones, etc.), followed by analysis as described previously will allow detection of promoter sequences that are increased preferentially in the presence of the external factor. Analysis of these sequences allows determination of common features that can make the significant structural features more obvious. Reconstruction of a library of mutagenized sequences related to these initial sequences followed by reanalysis, again in the presence or absence of the external factor, will allow an evolutionary optimization of said sequences, ultimately leading to the selection of a de novo optimized promoter sequences that can be used in the construction of novel promoters or modified genes that are responsive to the external factor in question.

vi. Methods of Identifying Promoters Having Modulated Strengths or Transcription Efficiencies The methods described herein can be used to identify promoters derived from known promoters, but having increased or decreased transcription efficiencies. In varying embodiments, the insert suspected of comprising a functional promoter comprises a known promoter that has been mutated or mutagenized. The methods of promoter identification described above and herein allow one to take a known promoter sequence, mutagenize it, then run the mutagenized sequences through the promoter selection procedure, thereby generating a quasispecies of new promoters with a range of promoter strengths (ability to promote transcription). This procedure can be done iteratively or generationally (e.g., providing a population of polynucleotides comprising mutagenized promoters, selecting for promoters having increased or decreased transcription efficiency (as desired), recovering RT-PCR products, performing one or more further rounds of mutagenesis and then performing the steps of the methods again, as many iterations as necessary or desired).

In varying embodiments, methods for screening for promoters having modulated strength or transcription efficiencies entail the steps of:

a) providing a population of plasmids designed for screening promoters, the plasmids in the population containing an insert suspected of containing a functional promoter sequence, as described above and herein, wherein the promoter sequence comprises a polynucleotide from a known parent promoter that has been mutated;

b) transcribing the population of plasmids into RNA;

c) reverse transcribing into cDNA the population of circularized RNA transcripts of self-cleaved mini-monomer cassettes;

d) sequencing the inserted polynucleotides comprising a functional promoter in the population of cDNA reverse-transcripts of self-cleaved mini-monomer cassettes; and e) comparing the transcriptional strength or efficiency of the mutated promoter to the parent promoter.

Further embodiments of this method are the same as the methodologies described above and herein for identifying promoter polynucleotides.

vii. Methods of Identifying Natural Promoter Variants

The methods described herein can be used to identify genetic variation in the same promoter. Such variation may or may not correlate with a phenotypic difference (e.g., promoter strength and/or transcription efficiency). In varying embodiments, a library of inserts comprising the same known functional promoter from different individuals is created. The methods of promoter identification described above and herein allow one to take a known promoter sequence from a population of individuals to create a promoter library, and compare the promoter sequences of the different members of the library to identify sequence variation. For example, the promoter identification methods can be applied to the identification and comparison of the polynucleotide sequences of the same promoter from two or more different breeding line parents and the identification of variances in such promoter sequences, e.g., the identification of single nucleotide polymorphisms (SNPs). Natural variation can be found in regions of promoters that are not highly constrained and comparison of the polynucleotide sequences of the same promoter from two or more different individuals or a population of individuals can be used to identify SNPs and other longer regions within a promoter subject to variation. Genetic variation in a promoter may or may not correlate with variation in a phenotypic trait. This method applies the same methodologies described above for identifying promoter polynucleotides to two populations, e.g., one from each breeding line, and then comparing/aligning the promoter polynucleotide sequences found and looking for variation.

In varying embodiments, methods for identifying variation in a promoter sequence entail the steps of:

a) providing a population of plasmids designed for screening promoters, the plasmids in the population containing inserts suspected of containing functional promoter sequences, as described above and herein, wherein each population comprises the same potential promoter population from a different individual;

b) transcribing the population of plasmids into RNA;

c) reverse transcribing into cDNA the population of circularized RNA transcripts of self-cleaved mini-monomer cassettes;

d) sequencing the inserted polynucleotides comprising a functional promoter in the population of cDNA reverse-transcripts of self-cleaved mini-monomer cassettes; and e) comparing the polynucleotide sequences of the promoters from the different individuals, thereby identifying variation in the promoter sequence in the population.

Further embodiments of this method are the same as the methodologies described above and herein for identifying promoter polynucleotides.

b. For Identification of RNA Stability/Transcription Modifying Sequences

In varying embodiments, methods for screening for RNA stability/transcription modifying sequences entail the steps of:

a) providing a population of plasmids designed for screening for RNA stability/transcription modifying sequences, the plasmids in the population containing an insert suspected of having a RNA stability/transcription modifying sequence;

b) sequencing the first and second mini-monomer cassettes;

c) transcribing in vitro the population of plasmids into RNA from a control promoter (e.g., a promoter functional in a prokaryotic cell);

d) reverse transcribing into cDNA and sequencing the self-cleaved first and second mini-monomer cassettes transcribed in vitro in step c);

e) transcribing either in vitro or in a population of host cells the population of plasmids into RNA from a test promoter, wherein the test promoter is functional in a prokaryotic cell and/or in a eukaryotic cell;

f) reverse transcribing into cDNA and sequencing the self-cleaved first and second mini-monomer cassettes reverse transcribed in step e);

g) comparing the relative abundance or frequency of the self-cleaved second mini-monomer cassettes transcribed in vitro in step c) with the self-cleaved second mini-monomer cassettes transcribed in step e); and h) comparing the ratios of the relative abundance or frequency of the self-cleaved first mini-monomers to their linked self-cleaved second mini-monomers produced in step c) with those produced in step e).

Insertion of this library of DNA plasmids or constructs into cells or possibly transcriptionally active extracts and following the same basic protocol of RNA separation, isolation and/or purification, in vitro transcription, RT-PCR, and sequencing (e.g., deep sequencing) identifies RNA stabilizing or destabilizing inserts by screening for sequences that are increased or decreased in the deep sequencing population.

i. Sequencing the First and Second Mini-Monomer Cassettes

The first and second mini-monomer cassettes are sequenced using any methodologies known in the art. Such methodologies are described, e.g., in Green and Sambrook, Molecular Cloning, A Laboratory Manual, 4th Ed., Cold Spring Harbor Press, (2012). In varying embodiments, next generation sequencing, deep sequencing or ultra deep sequencing methodologies are applied, as described above.

A library of barcoded first mini-monomer/insert containing second mini-monomer is made. Construction of functional libraries begins with cloning of the barcodes into the first mini-monomer cassette, followed by sequencing (e.g., deep sequencing) to determine library extent. This first step barcoded library is then used to construct a library of inserts for functional testing. A subsequent round of sequencing (e.g., deep sequencing) of the barcode library and insert-containing library links any individual plasmid library member's barcode and insert sequence and shows the distribution of the sequences in the library (whether some more prevalent than others, for example).

ii. Transcribing In Vitro the Population of Plasmids into RNA

In vitro transcription of the first and second mini-monomers is performed, using methods known in the art, as discussed above. First and second mini-monomer cassettes that are fully transcribed into RNA, including downstream and then the upstream ribozyme cleavage sites, can self-cleave and circularize from the transcribed sequence.

Generally, transcription for this step is initiated from the control promoter (e.g., a promoter functional in a prokaryotic cell) positioned 5' to the first mini-monomer cassette as an internal control for processing efficiency. Mini-monomer cassettes that are transcribed into RNA over their full length, including the upstream and downstream ribozyme cleavage sites, self-cleave and circularize from the context of the DNA plasmid. The self-cleaved and circularized mini-monomer cassettes can be recovered.

Figure 11:
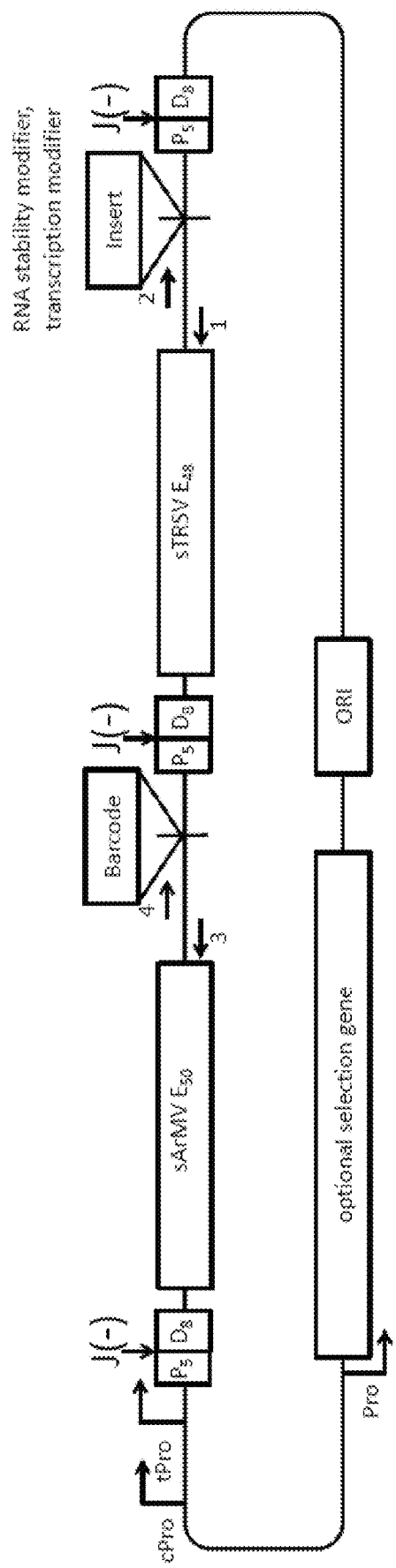
FIG. 11 illustrates an internally controlled, dimer mini-monomer construct. Notice the three P-D cleavage and ligation sites with two E ribozyme core sequences, in this embodiment, one from sArMV and one from sTRSV, between them. In some embodiments, the barcode sequence is a random DNA sequence with 15 N residues (approximately $1 \times 10^9$ different possible sequences).
Figure 12:
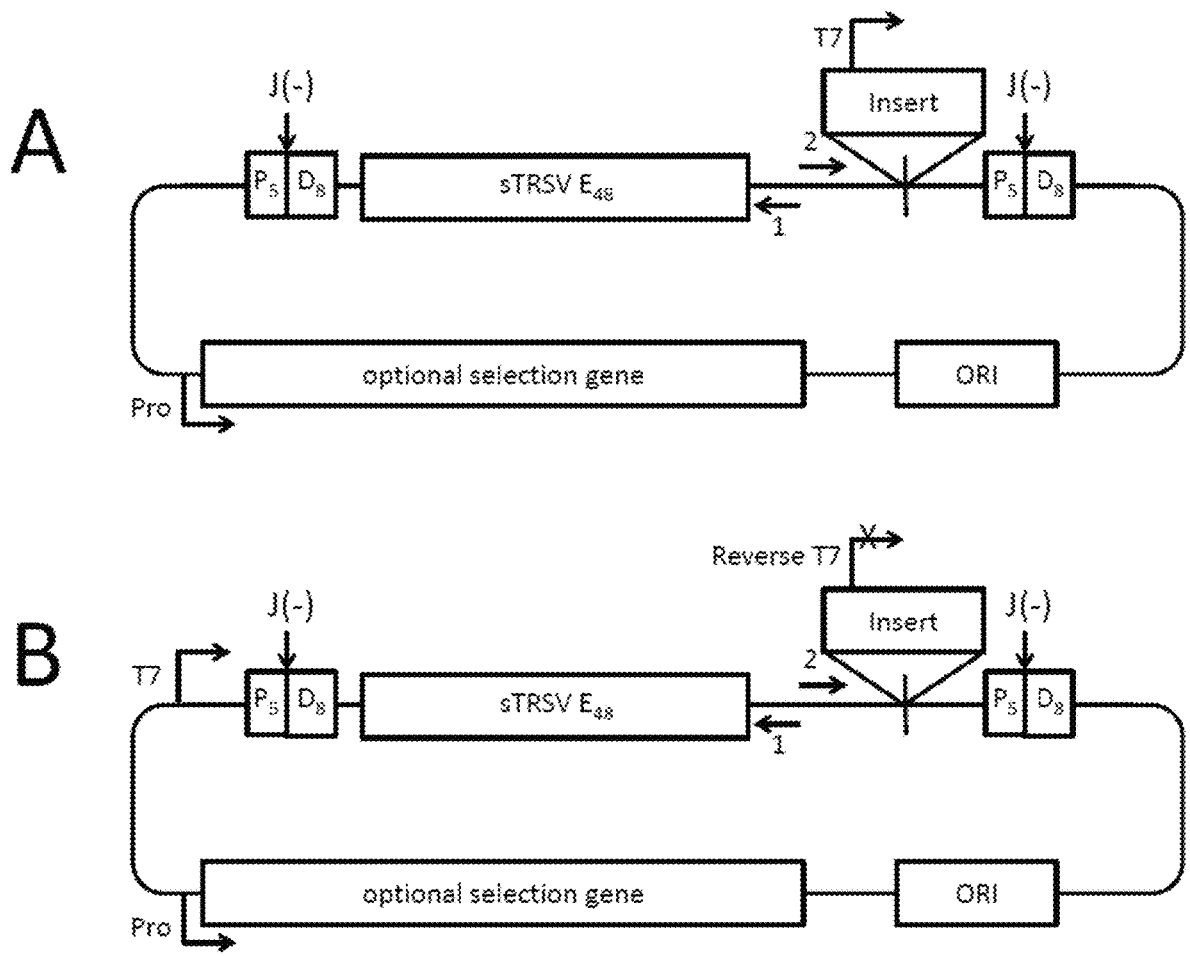
FIGS. 12A-B. (A) T7 construct containing a fully functional T7 RNA polymerase promoter as an insert. (B) reverse T7 ("7T") construct containing the reverse T7 RNA polymerase promoter (contains the T7 RNA polymerase promoter sequence written backwards) as a nonfunctional promoter as an insert.
Figure 13:
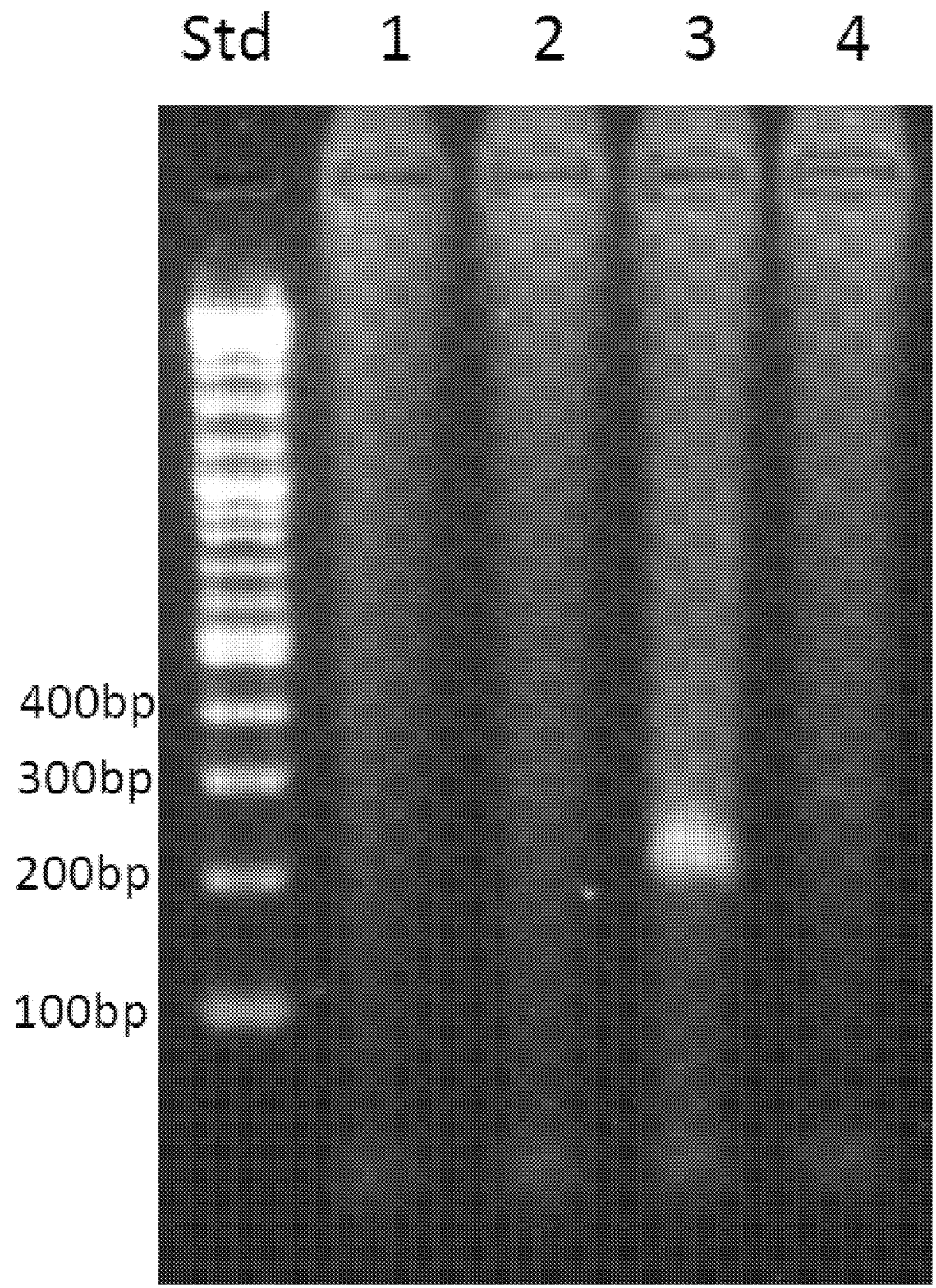
FIG. 13 illustrates T7 construct and reverse T7 construct incubated under transcription conditions with or without T7 RNA polymerase, phenol/chloroform/iso-amyl alcohol extracted, ethanol precipitated, reverse transcribed, and then subjected to 20 cycles of PCR with primers 1 and 2 (e.g., reverse and forward primer annealing polynucleotides, respectively). The appropriate sized fragment should be 221 base pairs long. This band is only seen in the T7 promoter construct incubated with T7 RNA polymerase under transcription conditions. Notice the faint band in lane 4 just below 300 base pairs. Lanes: (Std) 2-Log DNA ladder from New England Biolabs; (1) T7 promoter construct incubated without T7 RNA polymerase; (2) Reverse T7 promoter construct without T7 RNA polymerase; (3) T7 promoter construct with T7 RNA polymerase; and (4) Reverse T7 promoter construct with T7 RNA polymerase.
Figure 14:
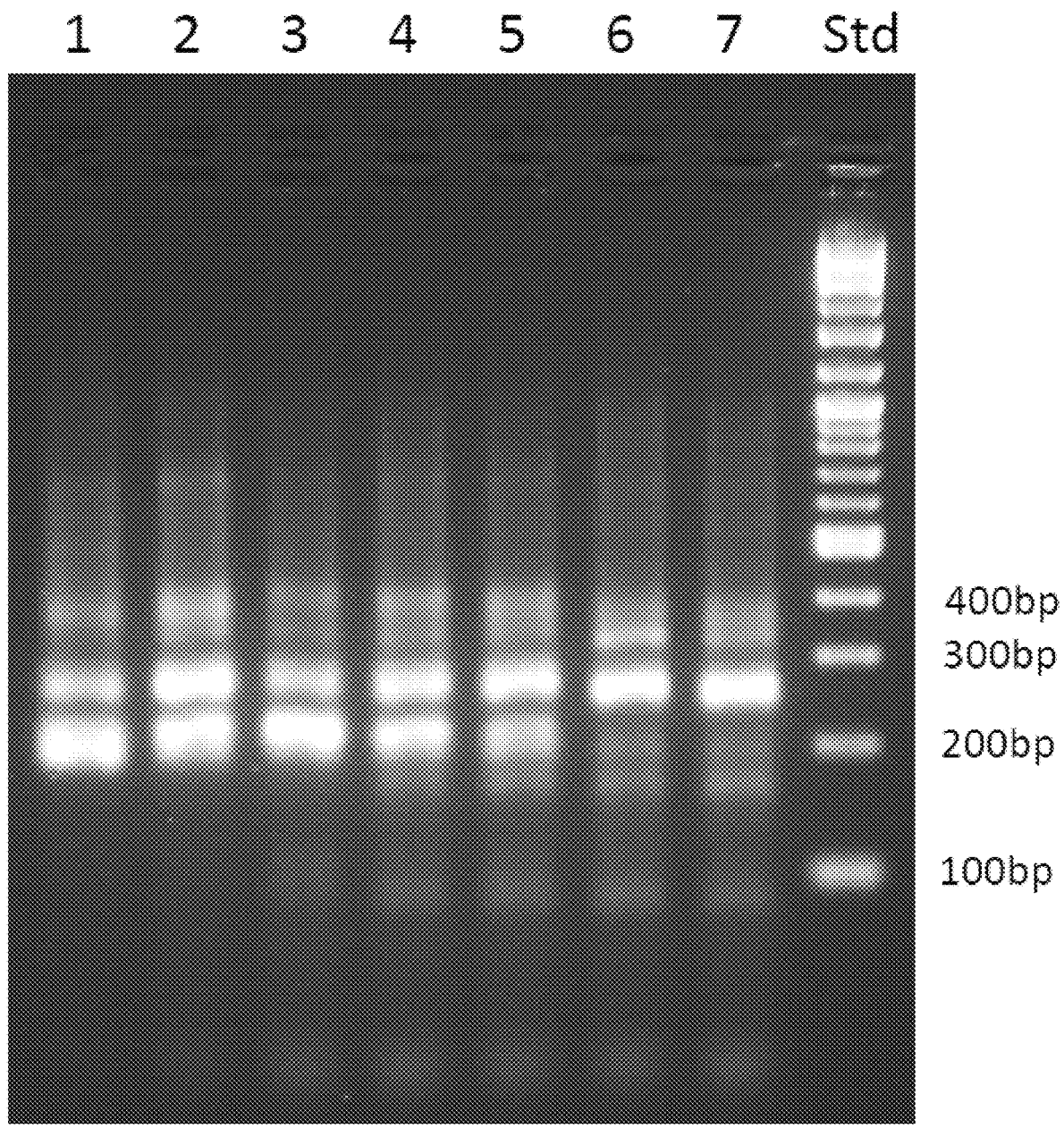
FIG. 14 illustrates a dilution series of the T7 construct mixed with a constant amount of the reverse T7 construct incubated under transcription conditions with T7 RNA polymerase, phenol/chloroform/iso-amyl alcohol extracted, ethanol precipitated, reverse transcribed, and then subjected to 35 cycles of PCR with primers 1 and 2. The appropriate sized fragment should be 221 base pairs long. This band is seen in the lane with $1:10^{-4}$ reverse T7 promoter construct: T7 promoter construct incubated with T7 RNA polymerase. Lanes: (1) 1:1 reverse T7 promoter construct:T7 promoter construct; (2) $1:10^{-1}$ reverse T7 promoter construct:T7 promoter construct; (3) $1:10^{-2}$ reverse T7 promoter construct: T7 promoter construct; (4) $1:10^{-3}$ reverse T7 promoter construct:T7 promoter construct; (5) $1:10^{-4}$ reverse T7 promoter construct:T7 promoter construct; (6) $1:10^{-5}$ reverse T7 promoter construct:T7 promoter construct; (7) reverse T7 promoter construct only; and (Std) 2-Log DNA ladder from New England Biolabs.

In varying embodiments, the methods further comprise the step of purifying or isolating the transcribed RNA from non-RNA. In varying embodiments, the methods further comprise the step of purifying or isolating the population of circularized RNA transcripts of self-cleaved mini-monomer cassettes. In varying embodiments, purifying or isolating circularized RNA transcripts of self-cleaved mini-monomer cassettes is performed by two-dimensional gel electrophoresis.

iii. Reverse Transcribing into cDNA and Sequencing the Self-Cleaved First and Second Mini-Monomer Cassettes Transcribed into RNA In Vitro The self-cleaved first and second mini-monomers that were transcribed into RNA in vitro are reverse-transcribed into cDNA and then sequenced (e.g., deep sequenced) using methods known in the art, as discussed above. Reverse transcription and sequencing (e.g., deep sequencing can be performed using any methods known in the art, as described above. Generally, reverse transcription in this step can be initiated from the first reverse primer annealing polynucleotide (e.g., for PCR or RT-PCR) for the first mini-monomer cassette and from the second reverse primer annealing polynucleotide (e.g., for PCR or RT-PCR) for the second mini-monomer cassette, wherein the location or positioning of the first and second forward and reverse primer annealing polynucleotides (e.g., for PCR or RT-PCR) is as depicted in FIG. 11. PCR is performed using the first forward and reverse primer annealing polynucleotides (e.g., for PCR or RT-PCR) for amplifying the first self-cleaved and circularized mini-monomer cassettes comprising the barcode polynucleotides and second forward and reverse primer annealing polynucleotides (e.g., for PCR or RT-PCR) for amplifying the second self-cleaved and circularized mini-monomer cassettes, comprising the insert suspected of encoding a RNA stability and/or transcriptional modifying sequence.

This step functions as an internal control for circularization efficiency within the first and second mini-monomer cassettes (barcode and insert containing RNA and/or transcription stability modifier). It is possible that particular barcodes or inserts have increased or decreased circularization when transcribed into RNA in vitro.

iv. Transcribing In Vitro or in a Population of Host Cells the Population of Plasmids into RNA The DNA plasmid library can be transcribed, in vitro or in a host cell. In varying embodiments, the DNA plasmid library is transcribed in vitro. This can be done according to methods known in the art, and described herein. In varying embodiments, the DNA plasmid library is transformed into a population of host cells, where they are transcribed into RNA, and the transcribed mini-monomers circularize and self-cleave within the host cell. Whether transcribed in vitro or in a host cell, the self-cleaved and circularized mini-monomers are recovered, reverse-transcribed into cDNA and sequenced (e.g., deep sequenced).

As discussed above, in vivo transformation of a suitable host cell with a closed circular DNA plasmid using any method known in the art, e.g., by electroporation of protoplasts, fusion of liposomes to cell membranes, cell transfection methods using calcium ions or PEG, use of gold or tungsten microparticles coated with plasmid with the gene gun. Mini-monomer cassettes that are transcribed into RNA along their full length, including the upstream and downstream ribozyme cleavage sites, can self-cleave and circularize. The self-cleaved and circularized mini-monomer cassettes can be recovered.

Accordingly, in varying embodiments, the methods further comprise the step of purifying or isolating the transcribed RNA from non-RNA. In varying embodiments, the methods further comprise the step of purifying or isolating the population of circularized RNA transcripts of self-cleaved mini-monomer cassettes. In varying embodiments, purifying or isolating circularized RNA transcripts of self-cleaved mini-monomer cassettes is performed by two-dimensional gel electrophoresis.

v. Reverse Transcribing into cDNA and Sequencing the Self-Cleaved First and Second Mini-Monomer Cassettes The self-cleaved first and second mini-monomers that were functionally transcribed into RNA either in vitro or in vivo (e.g., in a host cell) are reverse-transcribed into cDNA and then sequenced (e.g., deep sequenced) using methods known in the art, as discussed above. Reverse transcription and sequencing (e.g., deep sequencing can be performed using any methods known in the art, as described above. Generally, reverse transcription in this step can be initiated from the first reverse primer annealing polynucleotide (e.g., for PCR or RT-PCR) for the first mini-monomer cassette and from the second reverse primer annealing polynucleotide (e.g., for PCR or RT-PCR) for the second mini-monomer cassette, wherein the location or positioning of the first and second forward and reverse primer annealing polynucleotides (e.g., for PCR or RT-PCR) is as depicted in FIG. 11. PCR is performed using the first forward and reverse primer annealing polynucleotides for amplifying the first self-cleaved and circularized mini-monomer cassettes comprising the barcode polynucleotides and second forward and reverse primer annealing polynucleotides for amplifying the second self-cleaved and circularized mini-monomer cassettes, comprising the insert suspected of encoding a RNA stability and/or transcriptional modifying sequence.

vi. Comparing the Relative Abundance or Frequency of the Self-Cleaved Second Mini-Monomer Cassettes Reverse-Transcribed into cDNA In Vitro with the Self-Cleaved Second Mini-Monomer Cassettes Reverse-Transcribed into cDNA The frequency and abundance of circularized self-cleaved inserted polynucleotide sequences functionally transcribed into RNA either in vitro or in a host cell are compared with the frequency and abundance of circularized self-cleaved inserted polynucleotide sequences transcribed into RNA in the in vitro control. Any that have increased in relation to their frequency in the DNA library contain either a transcription enhancer or a RNA stabilizing sequence. Both possibilities can cause an increase in the amount of mini-monomer RNA with that sequence. Any that have decreased in relation to their frequency in the DNA library contain either a transcription decreasing sequence or a RNA destabilizing sequence. Both possibilities can cause a decrease in the amount of mini-monomer RNA with that sequence.

vii. Comparing the Ratios of the Relative Abundance or Frequency of the Self-Cleaved First Mini-Monomers to their Linked Self-Cleaved Second Mini-Monomers The ratios of the barcoded mini-monomers to their linked insert mini-monomers are compared. Reverse transcription can be performed, e.g., with the first and second reverse primers, followed by PCR with the second forward and reverse primers to measure the presence of the insert-containing mini-monomer and first forward and reverse primers to measure the presence of the barcode-containing mini-monomer. See, e.g., FIG. 11. Comparison of the ratio of the appropriate barcoded mini-monomer to its linked insert mini-monomer allows discrimination between those inserts that actually affect RNA stability and those that affect transcription. Those that affect RNA stability increase or decrease the insert mini-monomer relative to the barcode mini-monomer if they increase or decrease the RNA stability, respectively. Those that affect transcription only do not affect the ratio, instead increasing or decreasing both mini-monomers coordinately.

In the case of an increase, if the ratio is unchanged, then the sequence is a transcriptional enhancer. It causes both mini-monomers to increase the same amount. If the ratio is changed with the insert being higher, then it is a RNA stabilizing sequence. It only increases the amount of the insert mini-monomer. In the case of a decrease, if the ratio is unchanged, then the sequence is a transcriptional reducing sequence. It causes both mini-monomers to decrease the same amount. If the ratio is changed with the insert being lower, then it is a RNA destabilizing sequence. It only decreases the amount of the insert mini-monomer.

In varying embodiments, the ratio of the first bar-coded mini-monomer to the second insert-containing mini-monomer produced inside host cells can be normalized by division by the ratio of the first bar-coded mini-monomer to the second insert-containing mini-monomer produced in vitro. To provide an example, the ratio of the bar-coded mini-monomer to insert-containing mini-monomer is 0.5, e.g., due to a lower circularization efficiency of the bar-coded mini-monomer (presumably due to sequence specific effects on circularization by the bar code sequence). In the case of a transcriptional enhancer, an increase in the relative abundance of the insert-containing mini-monomer produced in the host cell is observed relative to that produced in vitro, but the ratio of the bar-coded mini-monomer to insert-containing mini-monomer produced in the host cells remains at 0.5. Likewise, in the case of a transcriptional repressor, a decrease in the relative abundance of the insert-containing mini-monomer produced in the host cell is observed relative to that produced in vitro, but the ratio of the bar-coded mini-monomer to insert-containing mini-monomer produced in the host cells remains at 0.5. In the case of a RNA stabilizing sequence, an increase in the relative abundance of the insert-containing mini-monomer produced in the host cell is observed relative to that produced in vitro, but the ratio of the bar-coded mini-monomer to insert-containing mini-monomer produced in the host cells is lower than 0.5 (more insert-containing mini-monomer relative to bar-coded mini-monomer). The ratio between the bar-coded mini-monomer and the insert-containing mini-monomer could be greater or less than 1.

viii. Exposure to External Influences

In varying embodiments, de novo selection and subsequent evolution of externally influenced transcriptional or RNA stability sequences is performed. Using a library containing inserted polynucleotides suspected of comprising a RNA stability/transcription modifying sequence, as described above, insertion of this library into cells with or without some external factor (e.g., $Ca^{++}$ ions, salt, temperature stress, hormones, etc.), followed by analysis as described previously will allow detection of sequences that are increased preferentially in the presence of the external factor. Analysis of these sequences allows determination of common features that can make the significant structural features more obvious. Reconstruction of a library of mutagenized sequences related to these initial sequences followed by reanalysis, again in the presence or absence of the external factor, will allow an evolutionary optimization of said sequences, ultimately leading to the selection of a de novo optimized transcriptional or RNA stability sequence that can be used in the construction of novel promoters or modified genes that are responsive to the external factor in question.

ix. Methods of Identifying Modulated RNA Stability/Transcription Modifying Sequences The methods described herein can be used to identify RNA stability/transcription modifying sequences derived from known RNA stability/transcription modifying sequences, but having increased or decreased RNA stability/transcription modifying efficiencies or strengths. In varying embodiments, the insert suspected of comprising a RNA stability/transcription modifying sequence comprises a known RNA stability/transcription modifying sequence that has been mutated or mutagenized. The methods of RNA stability/transcription modifying sequence identification described above and herein allow one to take a known RNA stability/transcription modifying sequence, mutagenize it, then run the mutagenized sequences through the RNA stability/transcription modifying sequences selection procedure, thereby generating a quasispecies of new RNA stability/transcription modifying sequences with a range of RNA stability/transcription modifying sequences strengths (ability to increase or decrease RNA stability and/or transcription). This procedure can be done iteratively or generationally (e.g., providing a population of polynucleotides comprising mutagenized promoters, selecting for RNA stability/transcription modifying sequences having increased or decreased transcription efficiency (as desired), recovering RT-PCR products, performing one or more further rounds of mutagenesis and then performing the steps of the methods again, as many iterations as necessary or desired).

4. Method of Identifying a Polynucleotide Sequence Bound by a Transcription Factor Further provided are methods of identifying a polynucleotide sequence bound by a transcription factor. The methods are useful to identify the polynucleotide sequence or sequences bound by any transcription factor known in the art. Sequences identified to be bound by one or more transcription factors can be mutagenized, rerun through the steps of the methods as described herein, and then used to determine stronger or weaker binding site for the transcription factor, as desired. The method entails using a inhibitory nucleic acid, e.g., an RNAi, to reduce the expression and/or activity of the transcription factor being tested. In varying embodiments, the steps of the method comprise:

a) providing a population of plasmids as described above and herein for use in identifying RNA stability/transcription modifying sequences.

b) sequencing the first and second mini-monomer cassettes; thereby linking the barcode polynucleotide to a unique inserted polynucleotide suspected of comprising a RNA stability modifier;

c) transcribing in vitro the population of plasmids into RNA from a control promoter (e.g., a promoter functional in a prokaryotic cell), wherein RNA transcripts comprising the first and second mini-monomer cassettes self-cleave from the transcript;

d) sequencing the self-cleaved first and second mini-monomer cassettes transcribed in vitro; thereby controlling for cleavage and circularization efficiency;

e) transcribing the population of plasmids into RNA from the promoter functional in a eukaryotic cell, wherein the transcribing is performed in a population of host cells and in the presence and absence of an inhibitory nucleic acid that inhibits or reduces the expression of the transcription factor, wherein RNA transcripts comprising the first and second mini-monomer cassettes self-cleave from the transcript;

f) sequencing the self-cleaved first and second mini-monomer cassettes transcribed in a host cell;

g) comparing the relative abundance or frequency of the self-cleaved second mini-monomer cassettes transcribed in the host cell in the presence of the inhibitory nucleic acid with the self-cleaved second mini-monomer cassettes transcribed in a host cell in the absence of the inhibitory nucleic acid, wherein a higher or increased relative abundance or frequency of the self-cleaved second mini-monomer cassettes transcribed in a host cell in the absence of the inhibitory nucleic acid identifies the polynucleotide sequence bound by the transcription factor. In varying embodiments, the inhibitory nucleic acid is an interfering RNA polynucleotide (RNAi). The transcription and sequencing steps can be performed as described above. Further embodiments of the method are as described above for the methods of identifying RNA stability/transcription modifying sequences.

5. Kits

Further provided are kits containing one or more of the constructs or DNA plasmids for screening for promoters or for RNA or transcriptional modifying sequences, as described herein. In varying embodiments, the kits can further comprise in one or more containers or vessels buffers, reagents, nucleotides, enzymes, control polynucleotides, and instructions for use. In varying embodiments, the kits comprise a library of DNA plasmids for use in screening for RNA or transcriptional modifying sequences, wherein in each member of the library, the first mini-monomer cassette has already been preloaded with a unique barcode polynucleotide. Accordingly, each member of the library of DNA plasmids contains a first mini-monomer cassette comprising a different barcode polynucleotide.

EXAMPLES

The following examples are offered to illustrate, but not to limit the claimed invention.

Example 1

An Illustrative Protocol for Selection of Promoters

Materials
1. A plasmid containing
   a. a selectable marker for identifying *E. coli* bacteria containing said plasmid
   b. an origin of replication for maintenance of the plasmid within the *E. coli* bacteria
   c. a mini-monomer cassette containing
      i. a ribozyme catalytic core from the negative strand of the satellite RNA of tobacco ringspot virus (sTRSV)
      ii. two ribozyme cleavage/ligation sites capable of being cleaved and ligated by the ribozyme catalytic core
      iii. binding sites for primers appropriate for reverse transcriptase-polymerase chain reaction (RT-PCR)
      iv. a multiple cloning site (MCS) containing multiple sequentially arranged, adjacent restriction endonuclease cleavage sites for cloning. See, e.g., FIGS. 1-2A-E and 6-8.
2. Random DNA fragments inserted into the MCS from any of the following sources
   a. In vivo-derived DNAs from any biological organism including, but not limited to plants, animals, fungi, protists, bacteria, or Archaea
   b. In vitro-derived DNAs from chemical or enzymatic DNA synthesis
   c. Said random DNA fragments prepared by total or partial DNA degradation by restriction endonuclease cleavage, physical fragmentation followed by ligation of DNA linkers, PCR with random nonamers attached to specific primers followed by PCR with these specific primers, or other methods of DNA fragmentation appropriate for cloning into one or more MCS restriction endonuclease cleavage sites,
3. Reagents for preparation and ligation of random DNA fragments into plasmid to create plasmid libraries
   a. Restriction endonucleases
   b. T4 DNA ligase
   c. Deoxyribonucleotide triphosphates
   d. Klenow fragment of *E. coli* DNA polymerase
4. Reagents for introduction and amplification of plasmid libraries in *E. coli*
   a. Electroporation-quality competent *E. coli* cells
   b. Bacterial growth media, both as plates and liquid
   c. Plasmid DNA preparation materials
5. A source of RNA polymerase activity, such as:
   a. Living cells
   b. Isolated nuclei
   c. Transcriptionally-active cell extracts
   d. Purified RNA polymerases
6. Buffers, salts and ribonucleotide triphosphates appropriate for RNA synthesis if done outside living cells (in vitro)
7. Material for delivery of plasmid DNA to living cells (in vivo), including, but not limited to
   a. Liposomes
   b. Microparticles for particle bombardment made of
      i. Gold, tungsten or other material
8. Reagents for:
   a. Separation, isolation and/or purification of RNA
   b. Removal of any residual DNA
9. A primer (primer 1) complementary to any mini-monomer RNA synthesized
10. A primer (primer 2) with the same sequence as any mini-monomer RNA synthesized
11. Reverse transcriptase
12. Buffers, salts and deoxyribonucleotide triphosphates appropriate for cDNA synthesis in vitro
13. Thermo-stable DNA polymerase for PCR
14. Buffers, salts and deoxyribonucleotide triphosphates appropriate for PCR in vitro
15. Materials for cloning PCR products
16. Materials for direct sequencing Method An illustrative method for producing illustrative mini-monomer RNAs containing promoter sequences
I. Construction of Plasmid Library (Listed in Materials)

Mini-monomer cassette-containing plasmid is digested at one of the restriction endonuclease cleavage sites within the MCS, an example of which would be the restriction endonuclease, Sal I, which leaves a four base palindromic 5' overhang of TCGA. Addition of dTTP, dCTP and the Klenow fragment of *E. coli* DNA polymerase will convert the four base, palindromic 5' overhang left after Sal I cleavage to a two base, non-palindromic 5' overhang. TC 5' extensions will no longer ligate to each other. This reduces the background of re-ligated plasmid during the cloning of the DNA library. The plasmid is now ready to receive the random DNA fragments.

The random DNA fragments can be produced in a variety of ways.

A desired organism's DNA must be purified by either a commercial DNA purification kit (DNAeasy) or other previously established non-commercial method (CTAB, etc.). The simplest method of producing the random DNA fragments from this purified DNA is complete digestion with a restriction endonuclease that will ultimately be compatible with the half-filled, Sal I digested mini-monomer cassette-containing plasmid, an example would be the restriction endonuclease, Sau3AI, which recognizes and cleaves the 4 base sequence GATC, leaves a 4 base palindromic 5' overhang, and should cut randomly approximately every 256 base pairs. Addition of dGTP, dATP and the Klenow fragment of E. coli DNA polymerase will convert the four base, palindromic 5' overhang left after Sau3AI cleavage to a two base, non-palindromic 5' overhang just as was done for the Sal I cleaved plasmid. The 2 base, non-palindromic 5' overhangs of the Sal I-cleaved plasmid and the Sau3AI-cleaved DNA are not compatible with themselves, but are compatible with each other. This should reduce the background of plasmid self-ligation, ligation of insert DNAs to each other and ensure that most plasmids recovered during library construction will have one and only one insert. The use of Sal I and Sau3AI is not exclusive (see Korch C. "Cross index for improving cloning selectivity by partially filling in 5'-extensions of DNA produced by type II restriction endonucleases." Nucleic Acids Res. 1987 Apr. 24; 15(8):3199-220). Many other restriction endonuclease pairs can be used in the same way and the restriction endonuclease cleavage sites in the MCS are chosen to maximize the number of possible cloning choices.

Alternative preparation methods for the purified organismal DNA include partial rather than complete digestion with the desired restriction endonuclease, PCR with primers ending with random nonamer sequences (Robi D. Mitra and George M. Church. (1999) "In situ localized amplification and contact replication of many individual DNA molecules" Nucl. Acids Res. 27 (24)) followed by size selection followed by restriction endonuclease cleavage and filling as described, or random fragmentation and size fractionation of the DNA followed by ligation of linkers with compatible overhangs for ligation to the half-filled, Sal I cleaved plasmid, (See, e.g., Zabarovsky E R, Allikmets R L. (1986) "An improved technique for the efficient construction of gene libraries by partial filling-in of cohesive ends." Gene 42(1): 119-23; Sambrook, J. and Russell, D. W. (2001) "Molecular Cloning: A Laboratory Manual." Cold Spring Harbor Laboratory Press, Cold Spring Harbor, N.Y.)

An alternative to the use of organismal DNA is the use of chemically-synthesized random DNA and selection of any functional promoters from that random DNA population. Ligation of the inserts into the mini-monomer vector makes a plasmid library.

II. Introduce the Plasmid Library (from 1 Listed in Materials) Using Materials (from 3 or 4) into an Environment Containing RNA Polymerase (from 2) Under Appropriate Conditions for RNA Synthesis Either In Vitro or In Vivo.

An In Vitro Example

Prepare a library of randomized chemically synthesized DNA sequences based on the existing bacteriophage T7 RNA polymerase promoter cloned into the mini-monomer vector. Incubate this library with purified bacteriophage T7 RNA polymerase.

An In Vivo Example

For tobacco promoters, use inserts from tobacco genomic DNA cloned into the mini-monomer vector to make a library. Prepare plasmid DNA from the complete library, coat gold or tungsten particles (from 7b) with the library plasmid DNA, then use a biolistic particle delivery system to transfer the library of plasmids into plant nuclei (Julie R. Kikkert, Jose R. Vidal, and Bruce I. Reisch "Stable Transformation of Plant Cells by Particle Bombardment/Biolistics" Methods in Molecular Biology, vol. 286: Transgenic Plants: Methods and Protocols Edited by: L. Peña © Humana Press Inc., Totowa, N.J.).

III. Purification of Total RNA and Removal of any Residual DNA Using Appropriate Reagents (from 5).

In vitro synthesized RNA is purified after removal of the plasmid DNA library by digestion with commercial RNase-free DNase (Qiagen), followed by phenol/chloroform/isoamyl alcohol (25:24:1) extraction, removal of the aqueous phase to a new tube, and ethanol precipitation of the RNA from the aqueous phase with or without glycogen or linear acrylamide carrier.

In vivo synthesized RNA is purified with either a commercial kit (Qiagen RNAeasy) or with a TRIzol extraction protocol (Chomczynski, P., and Sacchi, N. (1987) Single Step Method of RNA Isolation by Acid Guanidinium Thiocyanate-Phenol-Chloroform Extraction. Anal. Biochem. 162, 156-159) (alternative protocols are used as needed depending on the source of the RNA to be purified).

IV. cDNA Synthesis Using Reverse Transcriptase, Buffer and Primer (from 9-12)

cDNA synthesis from purified total RNA is done using SuperScript II using the manufacturer's protocol (Life Technologies). Alternatively SuperScript III or other reverse transcriptase can be used. Primer 1 (from 9) is added to the total RNA in water and deoxynucleotide triphosphates, heated to 65 degrees C. for 5 minutes followed by quick chilling on ice. The other components necessary for cDNA synthesis is added (first strand reverse transcriptase buffer, dithiothreitol (DTT), and the mixture incubated at 42 for 2 minutes. Reverse transcriptase is added and the entire mixture is incubated at 42 degrees C. for 50 minutes, followed by enzyme inactivation at 70 degrees C. for 15 minutes.

V. PCR Using the Primers, Buffers, and Thermo-Stable DNA Polymerase (from 9, 10, 13 and 14)

PCR reactions are done on the synthesized cDNA using Herculase II Fusion DNA polymerase (Agilent Genomics) using the manufacturer's protocol. Alternatively, other thermostable DNA polymerases can be substituted such as Phusion DNA polymerase (NewEnglandBiolabs).

Annealing conditions for the PCR are adjusted depending on the melting temperatures based on the specific sequences of primers 1 and 2 (from 9 and 10). Extension times should be minimized to amplify only the smaller products derived from cDNA derived from the total RNA containing the circular ribozyme-ligated RNA. The number of PCR cycles necessary should be determined empirically depending on the concentration of amplifiable cDNA present.

Newly synthesized PCR products are checked on either 1 to 2 percent TBE or TAE agarose gels or on 5% non-denaturing TBE polyacrylamide gels depending on the resolution desired for a given experiment. Purification of any individual strong bands can be achieved from either of these gel types, if desired.

VI. Cloning Newly Synthesized PCR Products (from 15) or Direct Sequencing of New Synthesized PCR Products (from 16)

Once synthesized, PCR products can either be cloned as blunt ended DNA fragments by TOPO cloning (Life Technologies) using the manufacturer's protocol, or by restriction endonuclease cleavage of the PCR products at restriction endonuclease cleavage sites incorporated into primers 1 and 2 back into the mini-monomer plasmid for subsequent analysis or further rounds of selection, or into any other plasmid containing compatible restriction endonuclease cleavage sites. These clones represent individual promoter sequences. General mutation, for example through mutagenic PCR, of these individual promoters followed by subsequent selection and analysis of the promoter strength in vitro or in vivo leads to potentially patentable material.

Direct sequencing is an essential aspect of this method and depends on the use of primer 1 and 2 (from 9 and 10) chosen to match existing deep sequencing primer sets, for example those for MiSeq or HiSeq (Illumina), including the ability to use "bar coding" to get sequences from multiple experiments in a single deep sequence run due to sequencing costs (Illumina). The selection of MiSeq, which produces fewer total sequences (10s of millions), or HiSeq, which produces more total sequences (100s of millions) are made based on the expectation of the complexity of the potential promoter population being examined and the need for getting sufficient numbers of sequences for statistical analysis.

Example 2

An Illustration of Promoter Selection

This example illustrates an embodiment of the methods for selection of polynucleotides encoding a promoter.

Figure 6:
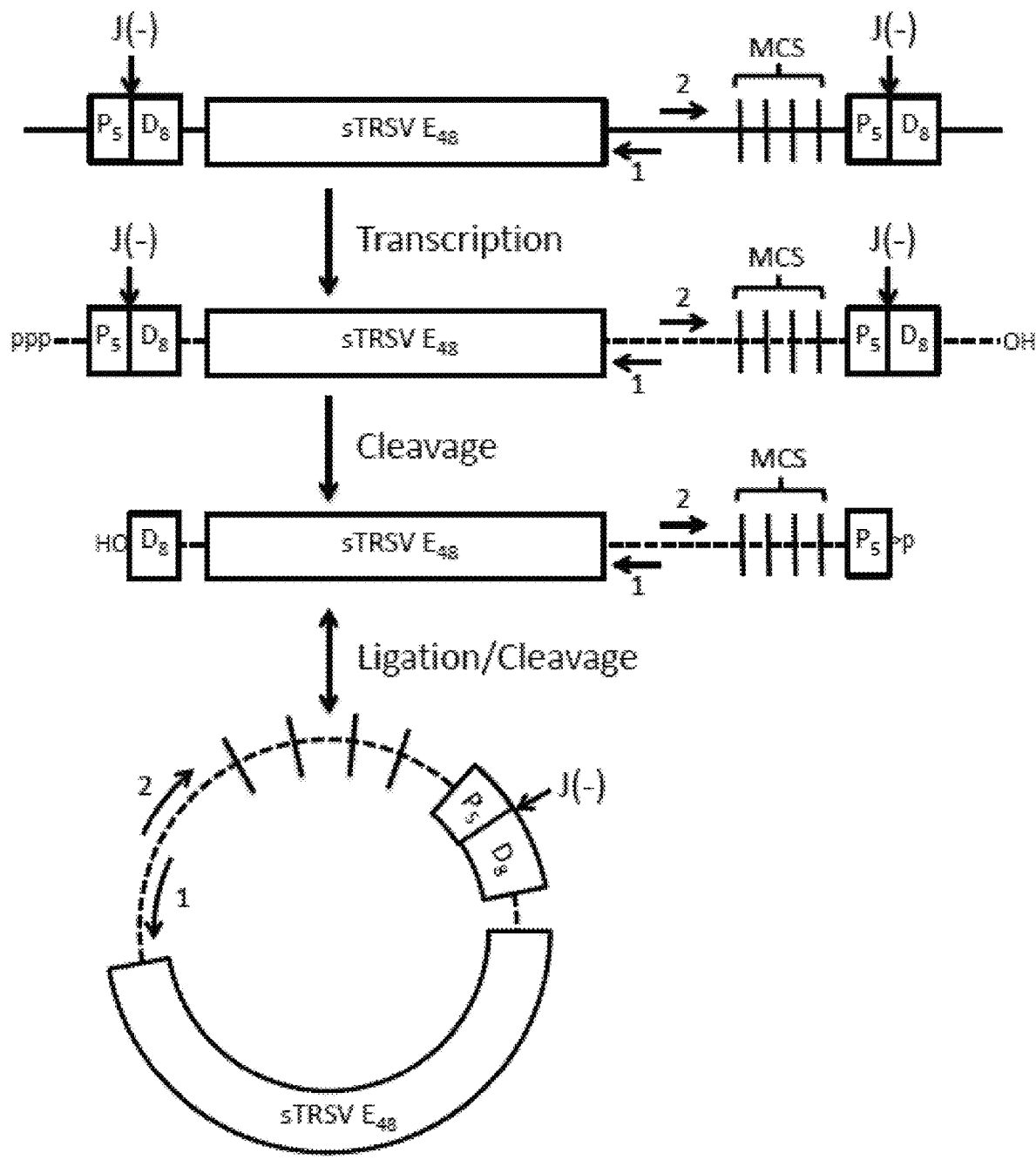
FIG. 6 illustrates a mini-monomer cassette. P and D represent the 5' and 3' sides of the (-) strand ribozyme cleavage size. E represents the (-) strand ribozyme catalytic core. The subscripted numbers represent the number of ribozyme catalytic core nucleotides present in each of these sections. The J(-) designated by the black down arrows represents the cleavage and ligation sites used by the ribozyme catalytic core. The multiple cloning site (MCS) has a number of unique restriction endonuclease cleavage sites. The black arrows labeled 1 and 2 represent primers for RT-PCR. The arrows represent the 3' end of the primers. Transcription produces a primary transcript beginning with a 5' triphosphate (ppp) and a 3' hydroxyl (OH). Ribozyme-mediated processing (e.g., self-cleaving) at the J(-) sites giving a linear mini-monomer RNA with a 5' hydroxyl (HO) and a 2':3' cyclic phosphodiester (>p). Intramolecular ligation and cleavage interconverts the linear mini-monomer RNA to a circular mini-monomer RNA.

The initial construct can have the following form. Two (-) strand ribozyme cleavage sites along with a (-) strand ribozyme catalytic core is cloned along with a multiple cloning site in the follow order (FIG. 6). This ribozyme insert is referred to as a mini-monomer.

Transcription of this insert by a promoter outside the mini-monomer insert produces a primary transcript shown in FIG. 6. Complete ribozyme-mediated cleavage of this primary transcript produces the linear mini-monomer RNA (FIG. 6). The other cleavage products as well as partial ribozyme-mediated cleavage products are not shown, but would be present. Intramolecular ligation and cleavage interconverts this product from a linear mini-monomer to a circular mini-monomer form and from a circular mini-monomer to a linear mini-monomer form respectively.

This mini-monomer cassette is cloned into a plasmid backbone. In this example pUN is used. pUN is a minimal plasmid derived from pUC18 by removal of all but the origin of replication and the selection gene (here, an antibiotic resistance gene, e.g., a beta-lactamase (bla) gene). In this example, the plasmid backbone contains two unique restriction sites, EcoRV and NotI. pUN was selected for its short length to maximize the chances of greater than full length transcripts being produced. The mini-monomer cassette is cloned directionally such that transcription from the bla gene promoter produces the antisense version of the ribozyme fragment (FIG. 7).

FIG. 7 shows the plasmid backbone with mini-monomer cassette construct (e.g, pUN1). Notice that the promoter for the beta-lactamase gene is oriented such that any transcription from it gives the antisense of the mini-monomer cassette. This lowers the possibility of accidental promoter discovery due to the beta-lactamase promoter, however it could be in either orientation. Inserts possibly containing eukaryotic promoters are cloned into the mini-monomer cassette MCS of the plasmid backbone (e.g, pUN1)-minimonomer cassette plasmid. These inserts can have a large number of sources such as fragments containing random nucleotides, restriction fragments of eukaryotic DNA, or randomized PCR fragments of eukaryotic DNA, most likely size selected. This is not an exhaustive list of possible insert DNA sources.

An insert containing a functional eukaryotic promoter is transcribed into RNA from its transcription start site. Notice that while part of the insert is found at the 5' end of the primary transcript, most, if not all, of the promoter itself is not found until later. However, as the plasmid backbone (e.g., pUN) is small and is designed not to contain a functional eukaryotic terminator, the primary transcript continues around the full length of the plasmid and the full insert on its second pass through that part of the plasmid. In the absence of a terminator, the primary transcript can be substantially longer than shown, and will produce the full-length mini-monomer RNA sequence containing the functional promoter.

Optionally, a control promoter (cPro), e.g., a promoter functional in a prokaryotic cell (e.g., a T7 RNA polymerase promoter and can be placed immediately 5' of the initial ribozyme cleavage site as shown in the lower construct FIG. 8. Transcription of the plasmid library in vitro with T7 RNA polymerase followed by RT-PCR with primers 1 and 2 and deep sequencing gives a processing and library bias-controlled deep sequencing data set for comparison with deep sequencing data sets derived from internal promoters (tPro in the lower construct in FIG. 8). This is not absolutely necessary as there are other ways of dealing with this issue. For example, one can perform PCR of the plasmid library with primers where the upstream primer has a RNA polymerase promoter (e.g., bacteriophage T3, T7 or SP6) attached.

The primary transcript from a test polynucleotide suspected of containing a functional promoter is shown in FIG. 9 and the complete processing products are shown in FIG. 10. In reality, partial processing products can also be present. Any transcript that is terminated after the ribozyme catalytic core ($E_{48}$), but before the $P_5$-$D_8$ immediately downstream of the catalytic core is processed, but are not able to form a circular mini-monomer containing the promoter-carrying insert. Any transcripts that terminate after the $P_5$-$D_8$ immediately downstream of the catalytic core can form a circular mini-monomer containing the promoter-carrying insert.

Synthesized cDNA from reverse transcription of RNA expressed from any insert carrying a functional eukaryotic promoter using primer 1, followed by PCR with primer 1 and primer 2 gives a PCR product, containing the mini-monomer sequence with the promoter-containing insert if the RNA template for reverse transcription is circular. Unprocessed transcripts are not circular. If PCR product is made on residual circular plasmid DNA, it gives a larger PCR product containing all of pUN-mini-monomer-insert DNA sequence, which is substantially larger and can be excluded by adjusting PCR conditions or, in the case of residual DNA template, by treatment with DNase or the restriction endonuclease Dpn I. These RT-PCR-derived DNAs can only be produced if a cloned DNA insert contains a functional eukaryotic promoter.

An alternative method to using total RNA involves purification of circular RNAs from all other RNAs using a two-dimensional gel system. The first dimension consists of a denaturing 7M urea, 1×TBE polyacrylamide gel of 5 to 6.5% total acrylamide concentration with 39:1 acrylamide: bis-acrylamide ratio. The second dimension consists of a denaturing 7M urea, 1×TBE polyacrylamide gel of the same total acrylamide concentration with 38:2 acrylamide:bis-acrylamide ratio. The two dimensions are cast together, the extracted total RNA is run first in the first dimension, which is then removed from the gel apparatus, rotated 90 degrees then put back on the gel apparatus and run in the second dimension. In a typical two-dimensional gel, two diagonals are seen—one for the linear RNAs and one for the circular RNAs. The circular RNAs are well separated from the linear RNAs. Due to the greater electrophoretic mobility of the linear RNAs in both the first and second dimensions compared to the circular RNAs, which are preferentially retarded in the second dimension gel compared to the linear RNAs, one also sees that the linear RNAs are not only on the linear diagonal, but also are farther down the linear diagonal than the circular RNAs are down the circular diagonal. Circular RNA size standards can be made without the primer binding sites to more easily delineate the diagonal of circles.

Using purified circular RNAs should give a much cleaner result. It also allows for a different approach to the reverse transcription as well. The primer binding sites can be positioned or located on opposite sides of the DNA insert with primer 1 being moved towards the 3' side of the insert. This change is not required, but is possible.

Example 3

An Illustration of RNA Stability/Transcription Modifier Selection

This example illustrates an embodiment of the methods for selection of polynucleotides encoding a RNA stability modifier or a transcription modifier.

In one embodiment, a promoter functional in a prokaryotic cell (e.g., a T7 RNA polymerase promoter) is retained for generating the same control described in Example 1, above. Adjacent to the control promoter (cPro, e.g., T7 RNA polymerase promoter) is a test promoter (tPro in FIG. 11) from the organism whose RNA stability and transcription modifying sequences are being sought. One difference between this construct and the one above is that the plasmid backbone itself need not be a minimal plasmid as transcription all the way around is not necessary. The use of a larger plasmid has the advantage of minimizing the chance of generating any competing PCR products all the way around the plasmid DNA.

As before an in vitro transcription with a control promoter (e.g., T7 RNA polymerase promoter) serves as an internal control as described above. As before, the library can be derived from natural sequences from an organism's DNA or can be randomized DNA (25 or 50 N residues, for example). Insertion of this plasmid library into cells or possibly transcriptionally active extracts followed by the same basic protocol of RT-PCR then deep sequencing gives RNA stabilizing or destabilizing inserts by looking for sequences that are increased or decreased in the deep sequenced population.

One possibility that must be considered is that any under or overrepresented sequence is due to a distance effect on the promoter by the insert, which is functioning as an enhancer or repressor of transcription. These can function up to 10 kilobases away from a promoter either upstream or downstream. To overcome to this problem, a construct as depicted in FIG. 11 can be used.

To reduce the possibility of recombination between two identical ribozyme core sequences, two related ribozyme cores can be used—for example, one from the satellite RNA of tobacco ringspot virus (sTRSV) as in the constructs described in Examples 1 and 2, and one from the satellite RNA of arabis mosaic virus (sArMV). The slightly different sequences not only decrease recombination between the two ribozyme cores, but also serve as an internal control for the deep sequencing. Construction of functional libraries begins with cloning of the barcodes into the first (e.g., sArMV) mini-monomer construct, followed by deep sequencing to determine library extent. This first step barcoded library is then used to construct a library of inserts for functional testing. Deep sequencing of this insert-containing library links any individual plasmid library member's barcode and insert sequence. Experimentation is performed as described previously with the variation of reverse transcription with primers 1 and 3, followed by PCR with primer sets 1 and 2 to measure the presence of the insert-containing mini-monomer and 3 and 4 to measure the presence of the barcode-containing mini-monomer. Comparison of the ratio of the appropriate barcoded mini-monomer to its linked insert mini-monomer allows discrimination between those inserts that actually affect RNA stability and those that affect transcription. Those that affect RNA stability increase or decrease the insert mini-monomer relative to the barcode mini-monomer if they increase or decrease the RNA stability respectively. Those that affect transcription only do not affect the ratio, instead increasing or decreasing both mini-monomers coordinately.

One attractive application of this approach is the de novo selection and subsequent evolution of externally influenced transcriptional or RNA stability sequences. Using a library containing random DNA fragments as insert sequences, insertion of this library into cells with or without some external factor (e.g., $Ca^{2+}$ ions, salt, temperature stress, hormones, etc.), followed by analysis as described previously allows detection of sequences that are increased preferentially in the presence of the external factor. Analysis of these sequences allows determination of common features that can make the significant structural features more obvious. Reconstruction of a library of mutagenized sequences related to these initial sequences followed by reanalysis, again in the presence or absence of the external factor, allows an evolutionary optimization of said sequences, ultimately leading to the selection of a de novo optimized transcriptional or RNA stability sequence that can be used in the construction of novel promoters or modified genes that are responsive to the external factor in question.

Example 4

Illustrative Selection of Functional Mutant T7 RNA Polymerase Promoters

Randomized oligonucleotides with 75% correct T7 RNA polymerase nucleotides at each of 17 positions were cloned into a mini-monomer cassette-containing plasmid forming a library containing approximately 500,000 unique sequences. Transcription with T7 RNA polymerase, phenol/chloroform/iso-amyl alcohol extraction, ethanol precipitation, and reverse transcription were performed as described for Examples 1 and 2, above. PCR was done of the resulting cDNA with primers that added appropriate indexed sequences for Illumina deep sequencing, as described above and herein. PCR was also done directly on the library plasmid, again adding the appropriate sequences for Illumina deep sequencing, but with a different index. The appropriately sized PCR products from the cDNA and from the plasmid library were gel purified. An equal mass amount of the two products were mixed and submitted for Illumina MiSeq deep sequencing. Approximately 5 million sequences were generated for each of the cDNA and plasmid library after separation based on the primer indices. For both cDNA and library PCR products, non-promoter sequences were trimmed, promoter sequences were separated based on the number of mutations present in each sequence, and the number of times any given sequence was present was determined. Comparing the ratio of the fraction of wildtype T7 RNA polymerase promoter present in the cDNA PCR products with the fraction of wildtype T7 RNA polymerase promoter present in the plasmid library PCR products with that for any given mutant provides an indication of the relative strength, defined as the promoter's ability to produce RNA, of the particular mutant promoter and the wildtype promoter. 73464 functional mutant T7 RNA polymerase promoters were selected in this manner. See, SEQ ID NOs: 10-73473 listed in the text-formatted computer readable sequence listing filed herewith, and incorporated herein by reference. They represent almost all possible double mutants, roughly half of the possible triple mutants and a smaller fraction of the possible quadruple and quintuple mutants. Sequences containing 6 or more mutations were not considered due to their low prevalence in the plasmid library. Only those mutants that were recovered as a cDNA and whose sequence was present in the initial plasmid library were included. Also, a few known double mutant promoters from an earlier T7 promoter paper were removed. The identified mutant T7 RNA polymerase promoters of SEQ ID NOs: 10-73473 find use to express coding and non-coding RNA molecules of interest, e.g., using methods well-known in the art.

Example 5

Illustrative Selection of Functional Mutant T7 RNA Polymerase Promoters In Vivo

The random library of approximately 500,000 unique T7 RNA polymerase promoters from Example 4 was inserted by electroporation into *E. coli* Shuffle T7 (New England Biolabs) cells, which contains an inducible T7 RNA polymerase gene. A small fraction of the cells was plated to determine that the entire library of 500,000 variants was represented. 2,000,000 transformants were made ensuring reasonable representation of the original library's complexity. The remaining cells were grown overnight at 37° C. to stationary phase. A fresh culture of the library was started and expression of the T7 RNA polymerase in vivo was induced by the addition of the inducer isopropyl β-D-1 thiogalactopyranoside (IPTG). After two hours, total RNA was purified from the cells (SigmaAldritch GenElute Universal Total RNA purification kit). Reverse transcription were performed as described for Examples 1 and 2, above. PCR was done of the resulting cDNA with primers that added appropriate indexed sequences for Illumina deep sequencing, as described above and herein. PCR was also done directly on the library plasmid prepared from a separate fraction of the same cells used for the total RNA purification at the same time point (2 hours after IPTG induction), again adding the appropriate sequences for Illumina deep sequencing, but with a different index. The appropriately sized PCR products from the cDNA and from the plasmid library were gel purified. An equal mass amount of the two products were mixed and submitted for Illumina MiSeq deep sequencing. Approximately 8 and 10 million sequences were generated respectively for the cDNA and plasmid library after separation based on the primer indices. For both cDNA and library PCR products, non-promoter sequences were trimmed, promoter sequences were separated based on the number of mutations present in each sequence, and the number of times any given sequence was present was determined. Comparing the ratio of the fraction of wildtype T7 RNA polymerase promoter present in the cDNA PCR products with the fraction of wildtype T7 RNA polymerase promoter present in the plasmid library PCR products with that for any given mutant provides an indication of the relative strength, defined as the promoter's ability to produce RNA, of the particular mutant promoter and the wildtype promoter. In this case, analysis was limited to single, double and triple mutants. We were able to analyze all possible single mutants, 99.9% of all possible double mutants, and 94.1% of all possible triple mutants. A smaller number of quadruple mutants were analyzed, but not beyond measuring their relative activity to wildtype. Five examples of mutant T7 RNA polymerase promoters with higher than wildtype activity were selected and inserted into plasmids with the coding sequence for the GFP protein. Increased in vivo expression of this gene was found after immunoblot with anti-GFP antibody.

Example 6

Illustrative Recovery of a Known Yeast Promoter Sequence after In Vivo Expression A yeast 2 micron plasmid containing a mini-monomer cassette was constructed beginning by doing PCR of the yeast 2 micron plasmid, pYES2 to delete gal promoters and leave a BglII, NotI and XbaI sites. The mini-monomer cassette was inserted into this as a BglII-XbaI fragment to give the desired construct. The TEF promoter construct was made by amplifying the TEF promoter by PCR as a BamHI-SalI fragment from the plasmid p427-TEF and cloned into the yeast 2 micron plasmid with the mini-monomer cassette as a BamHI-SalI fragment. The control construct (used the EGFP coding sequence in the antisense orientation) was made by moving the GFP coding sequence as a BglII-SalI fragment into the BamHI-SalI sites of the yeast 2 micron plasmid with the mini-monomer cassette. These plasmids were constructed and amplified using *E. coli* NEB5alpha. Plasmids were purified from carbenicillin resistant *E. coli* using Zymoresearch Zyppy™ Plasmid Miniprep Kit. The *Saccharomyces cerevisiae* yeast strain, INVSc1, was made competent and transformed using Zymoresearch Frozen-EZ Yeast Transformation II Kit™. Transformed yeast was selected and maintained on synthetic defined media lacking uracil. Selected yeast colonies were scraped from plates, crushed with sand in a morter and pestle in ice cold RLT Buffer and RNA isolated using a Qiagen RNeasy kit. Reverse transcription and PCR were as described in Example 1 and 2.

Example 7

Illustrative Recovery of Known Cytomegalovirus Core Promoter and Enhancer Sequences after In Vivo Expression The Cytomegalovirus (CMV) enhancer (Enh) was cloned upstream of a mini-monomer cassette. Into the multiple cloning site (MCS) was cloned the CMV core promoter (Pro). A second construction was made with the CMV Pro downstream of a mini-monomer cassette. Into the MCS of this second construct was cloned the CMV Enh. These plasmids were amplified in *E. coli* DH5alpha. Mirus CHO cell Transfection reagent was used to transfect CHO cells with each construct. A control with the transfection reagent but no plasmid DNA was done in parallel. Total RNA extracts were prepared after 24 hours using the SigmaAldrich GenElute Universal RNA extraction kit either with or without DNase treatment on the column. Reverse transcription and PCR were as described in Example 1 and 2.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

| INFORMAL SEQUENCE LISTING |
|---|
| Sequence ID No: 1-Nucleic acid sequence of Plasmid for Screening Promoters
AGATCTGACCGTCCTGTCCGTATGACAGAGAAGTCAACCAGAGAAACACACGTTGTGGTATA
TTACCTGGTGGCGCGCCGAATTCTGGAATTCTCGGGTGCCAAGGGTTCAGAGTTCTACAGTC
CGACGATCGCGGCCGCGTCGACGGATCCAAGCTTCCTGCAGGTGACCGTCCTGTCTCTAGAC
GCGTTGCTGGCGTTTTTCCATAGGCTCCGCCCCCCTGACGAGCATCACAAAAATCGACGCTC
AAGTCAGAGGTGGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGTAGGTCGT
TCGCTCCAAGCTGGGCTGTGTGCACGAACCCCCCGTTCAGCCCGACCGCTGCGCCTTATCCG
GTAACTATCGTCTTGAGTCCAACCCGGTAAGACACGACTTATCGCCACTGGCAGCAGCCACT
GGTAACAGGATTAGCAGAGCGAGGTATGTAGGCGGTGCTACAGAGTTCTTGAAGTGGTGGCC
TAACTACGGCTACACTAGAAGAACAGTATTTGGTATCTGCGCTCTGCTGAAGCCAGTTACCT
TCGGAAAAAGAGTTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGAT
TATCAAAAAGGATCTTCACCTAGATCCTTTTAAATTAAAAATGAAGTTTTAAATCAATCTAA
AGTATATATGAGTAAACTTGGTCTGACAGTTACCAATGCTTAATCAGTGAGGCACCTATCTC
AGCGATCTGTCTATTTCGTTCATCCATAGTTGCCTGACTCCCCGTCGTGTAGATAACTACGA
TACGGGAGGGCTTACCATCTGGCCCCAGTGCTGCAATGATACCGCGAGACCCACGCTCACCG
GCTCCAGATTTATCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAGTAAGTAGTTCGC
CAGTTAATAGTTTGCGCAACGTTGTTGCCATTGCTACAGGCATCGTGGTGTCACGCTCGTCG
TTTGGTATGGCTTCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAAGTAAGTTGGCCG
CAGTGTTATCACTCATGGTTATGGCAGCACTGCATAATTCTCTTACTGTCATGCCATCCGTA
AGATGCTTTTCTGTGACTGGTGAGTACTCAACCAAGTCATTCTGAGAATAGTGTATGCGGCG
ACCGAGTTGCTCTTGCCCGGCGTCAATACGGGATAATACCGCGCCACATAGCAGAACTTTAA
AAGTGCTCATCATTGGAAAACGTTCTTCGGGGCGAAAACTCTCAAGGATCTTACCGCTGTTG
AGATCCAGTTCGATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGGGAATAAGGGCGA
CACGGAAATGTTGAATACTCATACTCTTCCTTTTTCAATATTATTGAAGCATTTATCAGGGT
TATTGTCTCATGAGCGGATACATATTTGAATGTATTTAGAAAAATAAACAAATAGGGGTTCC
GCG |

SEQ ID NO: 1-Feature list

| Name | Location |
|---|---|
| ampR | rev: 960 . . . 1820 |
| rep (pMB1) | rev: 186 . . . 800 |
| ampr promoter | rev: 1821 . . . 1925 |
| seq1 | 1827 . . . 1856 |
| seq2 | rev: 237 . . . 260 |
| P5 | 6 . . . 10 |
| D8 | 11 . . . 18 |
| E48 | 24 . . . 71 |
| Multiple cloning site (MCS) | 72 . . . 85 |
| Reverse transcriptase primer 1 | 86 . . . 106 |
| Primer 2 | 107 . . . 132 |
| Multiple cloning site (MCS) | 133 . . . 166 |
| second P5 | 167 . . . 171 |
| second D8 | 172 . . . 179 |

Sequence ID No: 2-Nucleic acid sequence of Plasmid for Screening RNA Stability and/or transcription modifiers
AGATCTGACAGTACTGTCCGTATGACAGCGAAGTCAAACGGCGAAACACACCTTGTGGTA
TATTACCCGTTCCTAGGGTCTCGTGGGCTCGGTCGTCGGCAGCGTCGGTACCACTAGTTGAC
CGTCCTGTCCGTATGACAGAGAAGTCAACCAGAGAAACACACGTTGTGGTATATTACCTGGT
GGCGCGCCGAATTCTGGAATTCTCGGGTGCCAAGGGTTCAGAGTTCTACAGTCCGACGATCG
CGGCCGCGTCGACGGATCCAAGCTTCCTGCAGGTGACCGTCCTGTCTCTAGACGCGTTGCTG
GCGTTTTTCCATAGGCTCCGCCCCCCTGACGAGCATCACAAAAATCGACGCTCAAGTCAGAG
GTGGCGAAACCCGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCCCTTCGGGAAGC
GTGGCGCTTTCTCATAGCTCACGCTGTAGGTATCTCAGTTCGGTGTAGGTCGTTCGCTCCAA
GCTGGGCTGTGTGCACGAACCCCCCGTTCAGCCCGACCGCTGCGCCTTATCCGGTAACTATC
GTCTTGAGTCCAACCCGGTAAGACACGACTTATCGCCACTGGCAGCAGCCACTGGTAACAGG

INFORMAL SEQUENCE LISTING

```
ATTAGCAGAGCGAGGTATGTAGGCGGTGCTACAGAGTTCTTGAAGTGGTGGCCTAACTACGG
CTACACTAGAAGAACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTTTGC
AAGCAGCAGATTACGCGCAGAAAAAAAGGATCTCAAGAAGATCCTTTGATCTTTTCTACGGG
GTCTGACGCTCAGTGGAACGAAAACTCACGTTAAGGGATTTTGGTCATGAGATTATCAAAAA
GGATCTTCACCTAGATCCTTTTAAATTAAAAATGAAGTTTTAAATCAATCTAAAGTATATAT
GAGTAAACTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATACGGGAGG
GCTTACCATCTGGCCCCAGTGCTGCAATGATACCGCGAGACCCACGCTCACCGGCTCCAGAT
TTATCAGCAATAAACCAGCCAGCCGGAAGGGCCGAGCGCAGAAGTGGTCCTGCAACTTTATC
CGCCTCCATCCAGTCTATTAATTGTTGCCGGGAAGCTAGAGTAAGTAGTTCGCCAGTTAATA
GTTTGCGCAACGTTGTTGCCATTGCTACAGGCATCGTGGTGTCACGCTCGTCGTTTGGTATG
GCTTCATTCAGCTCCGGTTCCCAACGATCAAGGCGAGTTACATGATCCCCCATGTTGTGCAA
AAAAGCGGTTAGCTCCTTCGGTCCTCCGATCGTTGTCAGAAGTAAGTTGGCCGCAGTGTTAT
CACTCATGGTTATGGCAGCACTGCATAATTCTCTTACTGTCATGCCATCCGTAAGATGCTTT
TCTGTGACTGGTGAGTACTCAACCAAGTCATTCTGAGAATAGTGTATGCGGCGACCGAGTTG
CTCTTGCCCGGCGTCAATACGGGATAATACCGCGCCACATAGCAGAACTTTAAAAGTGCTCA
TCATTGGAAAACGTTCTTCGGGGCGAAAACTCTCAAGGATCTTACCGCTGTTGAGATCCAGT
TCGATGTAACCCACTCGTGCACCCAACTGATCTTCAGCATCTTTTACTTTCACCAGCGTTTC
TGGGTGAGCAAAAACAGGAAGGCAAATGCCGCAAAAAAGGGAATAAGGGCGACACGGAAAT
GTTGAATACTCATACTCTTCCTTTTTCAATATTATTGAAGCATTTATCAGGGTTATTGTCTC
ATGAGCGGATACATATTTGAATGTATTTAGAAAAATAAACAAATAGGGGTTCCGCG
```

SEQ ID NO: 2-Feature list

| Name | Location |
|---|---|
| ampR | rev: 1075 . . . 1935 |
| rep (pMB1) | rev: 301 . . . 915 |
| ampr promoter | rev: 1936 . . . 2040 |
| seq1 | 1942 . . . 1971 |
| seq2 | rev: 352 . . . 375 |
| P5 | 6 . . . 10 |
| D8 | 11 . . . 18 |
| sArMV E50 | 24 . . . 73 |
| Reverse transcriptase primer 3 | 80 . . . 94 |
| Primer 4 | 95 . . . 108 |
| Barcode insertion site | 115 . . . 120 |
| second P5 | 121 . . . 125 |
| second D8 | 126 . . . 133 |
| sTRSV E48 | 139 . . . 186 |
| Multiple cloning site (MCS) | 187 . . . 200 |
| Multiple cloning site (MCS) | 248 . . . 281 |
| Reverse transcriptase primer 1 | 201 . . . 221 |
| Primer 2 | 222 . . . 247 |
| third P5 | 282 . . . 286 |
| third D8 | 287 . . . 294 |

Sequence ID No: 3-negative strand self-cleavage domain of the satellite RNA of tobacco ringspot virus (sTRSV)
GACAGAGAAGTCAACCAGAGAAACACACGTTGTGGTATATTACCTGGT Sequence ID No: 4-negative strand self-cleavage domain of the satellite RNA of arabis mosaic virus (sArMV)
GACAGCGAAGTCAAACGGCGAAACACACCTTGTGTGGTATATTACCCGTT Sequence ID No: 5-negative strand self-cleavage domain of the satellite RNA of the satellite RNA of chicory yellow mottle virus (sCYMV)
GACAGCGAAGTCAGCCAGGGAAACACACCATGTGTGGTATATTATCTGGC Sequence ID No: 6-ribozyme cleavage site
TGACCGTCCTGTC Sequence ID No: 7-Generalized ribozyme cleavage site
$N_{S1}N_{S2}N_{S3}N_{S4}NGUCN_{S5}N_{S6}N_{S7}N_{S8}N_{S9}$
Wherein N = Any nucleotide (For RNA, A, C, G or U)

SEQ ID NO: 8 -generalized negative strand self-cleavage domain
$N_{E9}N_{E8}N_{E7}N_{E6}N_{E5}$(A/C)
$GAAN_{E4}N_{E3}N_{E2}N_{E1}N_{E10}N_{E11}N_{E12}N_{E13}N_{E14}AGAAACAN_{E20}N_{E21}N_{E22}N_{L6}$
$N_{L7}N_{L8}N_{L9}N_{L10}N_{E22'}N_{E21'}N_{E20'}GUAUAUUACN_{E14'}N_{E13'}N_{E12'}N_{E11'}N_{E10'}$ Wherein N = Any nucleotide (For RNA, A, C, G or U)

-continued

INFORMAL SEQUENCE LISTING

Interactions between the generalized ribozyme cleavage site (SEQ ID NO: 7) and the generalized negative strand self-cleavage domain (SEQ ID NO: 8) are via hydrogen bonds forming two stems-1 and 2

Stem 1 is formed by hydrogen bonds between $N_{S1}$ and $N_{E1}$, $N_{S2}$ and $N_{E2}$, $N_{S3}$ and $N_{E3}$, $N_{S4}$ and $N_{E4}$.

Stem 2 is formed by hydrogen bonds between $N_{S5}$ and $N_{E5}$, $N_{S6}$ and $N_{E6}$, $N_{S7}$ and $N_{E7}$, $N_{S8}$ and $N_{E8}$, $N_{S9}$ and $N_{E9}$.

Interactions within the generalized negative strand self-cleavage domain form 2 stems-3 and 4.

Stem 3 is formed by hydrogen bonds between $N_{E10}$ and $N_{E10'}$, $N_{E11}$ and $N_{E11'}$, $N_{E12}$ and $N_{E12'}$, $N_{E13}$ and $N_{E13'}$, $N_{E14}$ and $N_{E14'}$, Stem 4 is formed by hydrogen bonds between $N_{E20}$ and $N_{E20'}$, $N_{E21}$ and $N_{E21'}$, and $N_{E22}$ and $N_{E22'}$.

Stem 1 is essentially universally 4 base pairs long
Stem 2 can be as short as 4 base pairs, but can be longer
Stem 3 is essentially universally 5 base pairs long
Stem 4 is from 2 to 4 base pairs long depending on the source Loop 1 can be as small as 4 nucleotides, if it is a special sequence called a tetra-loop, but can be longer, e.g., 100's of nucleotides up to 1000 nucleotides
Loop 2 varies from 4 to 6 bases long in natural sequences Sequence ID No: 9-intentionally left blank Sequence ID Nos: 10-73473-listed in the text-formatted computer readable sequence listing filed herewith, and incorporated herein by reference.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10738302B2). An electronic copy of the "Sequence Listing" will also be available from the USPTO upon request and payment of the fee set forth in 37 CFR 1.19(b)(3).

What is claimed is:

1. A method of identifying functional promoter sequences, comprising:
   a) providing a population of plasmids comprising operably linked polynucleotides encoding:
      (i) a mini-monomer cassette, comprising a first ribozyme cleavage site and a second ribozyme cleavage site, and comprising between the first ribozyme cleavage site and the second ribozyme cleavage site:
         (1) a ribozyme catalytic core;
         (2) a reverse primer annealing polynucleotide;
         (3) a forward primer annealing polynucleotide; and
         (4) an inserted polynucleotide suspected of comprising a promoter; and
      (ii) a plasmid backbone, comprising an origin of replication;
   b) transcribing the population of plasmids into RNA; wherein the second ribozyme cleavage site is transcribed by an RNA polymerase when the inserted polynucleotide comprises a functional promoter; wherein RNA transcripts comprising the mini-monomer cassette self-cleave from the transcript, thereby forming a population of circularized RNA transcripts of self-cleaved mini-monomer cassettes;
   c) reverse transcribing into cDNA the population of circularized RNA transcripts of self-cleaved mini-monomer cassettes, thereby forming a population of cDNA reverse-transcripts of self-cleaved mini-monomer cassettes; and
   d) sequencing the inserted polynucleotides comprising a functional promoter in the population of cDNA reverse-transcripts of self-cleaved mini-monomer cassettes, whereby functional promoter sequences are identified.

2. The method of claim 1, further comprising after step b), the step of purifying or isolating the population of circularized RNA transcripts of self-cleaved mini-monomer cassettes.

3. The method of claim 1, wherein the reverse transcribing step comprises amplifying from the forward and reverse primer annealing polynucleotides.

4. The method of claim 1, wherein the step of transcribing the population of plasmids into RNA is performed in the presence and absence of an adjusted external factor, selected from the group consisting of temperature, pH, ion concentrations, ionic strength, salt concentration, calcium concentration, endoplasmic reticulum stress, hormones and ligands, heavy metals, toxins, glucose, the presence of virus, fungi, bacteria or other pathogens.

5. A method of identifying RNA stability modifying and/or transcription modifying sequences, comprising:
   a) providing a population of plasmids comprising operably linked polynucleotides encoding:
      i) a test promoter, wherein the test promoter is functional in a eukaryotic cell or in a prokaryotic cell;
      ii) a first mini-monomer cassette, comprising:
         (1) a first ribozyme cleavage site;
         (2) a first ribozyme catalytic core;
         (3) a first reverse primer annealing polynucleotide;
         (4) a first forward primer annealing polynucleotide;
         (5) a barcode polynucleotide
         (6) a second ribozyme cleavage site;
      iii) a second mini-monomer cassette, comprising:
         (1) the second ribozyme cleavage site;
         (2) a second ribozyme catalytic core;
         (3) a second reverse primer annealing polynucleotide;
         (4) a second forward primer annealing polynucleotide;
         (5) an inserted polynucleotide suspected of comprising an RNA stability modifier or a transcription modifier;
         (6) a third ribozyme cleavage site; and
      iv) a plasmid backbone, comprising an origin of replication;
   b) sequencing the first and second mini-monomer cassettes; thereby linking the barcode polynucleotide to a unique inserted polynucleotide suspected of comprising a RNA stability modifier;
   c) transcribing in vitro the population of plasmids into RNA from a control promoter functional in a prokaryotic cell, wherein RNA transcripts comprising the first and second mini-monomer cassettes self-cleave from the transcript;
   d) sequencing the self-cleaved first and second mini-monomer cassettes transcribed in vitro in step c); thereby controlling for cleavage and circularization efficiency;
   e) transcribing either in vitro or in a population of host cells the population of plasmids into RNA from a test promoter, wherein the test promoter functional in a eukaryotic cell or in a prokaryotic cell, wherein RNA transcripts comprising the first and second mini-monomer cassettes self-cleave from the transcript;
   f) sequencing the self-cleaved first and second mini-monomer cassettes transcribed in step e);
   g) comparing the relative abundance or frequency of the self-cleaved second mini-monomer cassettes transcribed in vitro in step c) with the self-cleaved second mini-monomer cassettes transcribed in step e), wherein a higher or increased relative abundance or frequency of the self-cleaved second mini-monomer cassettes transcribed in step e) identifies RNA stabilizing sequences or transcription enhancer sequences in the second mini-monomer cassette, and wherein a lower or decreased relative abundance or frequency of the self-cleaved second mini-monomer cassettes transcribed in step e) identifies RNA destabilizing sequences or transcription reduction sequences in the second mini-monomer cassette; and
   h) comparing the ratios of the relative abundance or frequency of the self-cleaved first mini-monomers to their linked self-cleaved second mini-monomers produced in vitro in step c) with those produced in step e),
   wherein a substantially unchanged and/or a substantially 1:1 ratio, and an increased relative abundance or frequency of the self-cleaved second mini-monomer cassettes transcribed in step e) identifies a transcriptional enhancer;
   wherein a ratio showing a higher relative abundance of the self-cleaved second mini-monomer, and an increased relative abundance or frequency of the self-cleaved second mini-monomer cassettes transcribed in step e) identifies a RNA stabilizing sequence;
   wherein a substantially unchanged and/or a substantially 1:1 ratio, and a decreased relative abundance or frequency of the self-cleaved second mini-monomer cassettes transcribed in step e) identifies a transcriptional reducing sequence; and
   wherein a ratio showing a lower relative abundance of the self-cleaved second mini-monomer, and a decreased relative abundance or frequency of the self-cleaved second mini-monomer cassettes transcribed in a host cell in step g) identifies a RNA destabilizing sequence.

6. A method of identifying a polynucleotide sequence bound by a transcription factor, comprising:
   a) providing a population of plasmids comprising operably linked polynucleotides encoding:
      i) a test promoter, wherein the test promoter is functional in a eukaryotic cell or in a prokaryotic cell;
      ii) a first mini-monomer cassette, comprising:
         (1) a first ribozyme cleavage site;
         (2) a first ribozyme catalytic core;
         (3) a first reverse primer annealing polynucleotide;
         (4) a first forward primer annealing polynucleotide;
         (5) a barcode polynucleotide
         (6) a second ribozyme cleavage site;
      iii) a second mini-monomer cassette, comprising:
         (1) the second ribozyme cleavage site;
         (2) a second ribozyme catalytic core;
         (3) a second reverse primer annealing polynucleotide;
         (4) a second forward primer annealing polynucleotide;
         (5) an inserted polynucleotide suspected of comprising an RNA stability modifier or a transcription modifier;
         (6) a third ribozyme cleavage site; and
      iv) a plasmid backbone, comprising an origin of replication;
   b) sequencing the first and second mini-monomer cassettes; thereby linking the barcode polynucleotide to a unique inserted polynucleotide suspected of comprising a RNA stability modifier;
   c) transcribing in vitro the population of plasmids into RNA from the promoter functional in a prokaryotic cell, wherein RNA transcripts comprising the first and second mini-monomer cassettes self-cleave from the transcript;
   d) sequencing the self-cleaved first and second mini-monomer cassettes transcribed in vitro; thereby controlling for cleavage and circularization efficiency;
   e) transcribing the population of plasmids into RNA from the promoter functional in a eukaryotic cell, wherein the transcribing is performed in a population of host cells and in the presence and absence of an inhibitory nucleic acid that inhibits or reduces the expression of the transcription factor, wherein RNA transcripts comprising the first and second mini-monomer cassettes self-cleave from the transcript;

f) sequencing the self-cleaved first and second mini-monomer cassettes transcribed in a host cell; and g) comparing the relative abundance or frequency of the self-cleaved second mini-monomer cassettes transcribed in the host cell in the presence of the inhibitory nucleic acid with the self-cleaved second mini-monomer cassettes transcribed in a host cell in the absence of the inhibitory nucleic acid, wherein a higher or increased relative abundance or frequency of the self-cleaved second mini-monomer cassettes transcribed in a host cell in the absence of the inhibitory nucleic acid identifies the polynucleotide sequence bound by the transcription factor.

7. The method of claim 6, wherein the inhibitory nucleic acid is an interfering RNA polynucleotide (RNAi).

8. The method of claim 5, wherein the step of transcribing the population of plasm ids into RNA is performed in the presence and absence of an adjusted external factor selected from the group consisting of temperature, pH, ion concentrations, ionic strength, salt concentration, calcium concentration, endoplasmic reticulum stress, hormones and ligands, heavy metals, toxins, glucose, the presence of virus, fungi, bacteria or other pathogens.

9. The method of claim 5, further comprising after step c), the step of purifying or isolating RNA from non-RNA.

10. The method of claim 5, wherein statistical analyses of a population of RT-PCR products are performed and the identified RNA stability modifying and/or transcription modifying sequences are ordered by strength.

11. The method of claim 5, wherein said polynucleotide comprises one or more promoters selected from the group consisting of SEQ ID NOs: 10-73473.

* * * * *